United States Patent
Alsareii et al.

(10) Patent No.: US 12,239,760 B1
(45) Date of Patent: Mar. 4, 2025

(54) ANTIBACTERIAL CONDUCTIVE SELF-HEALING HYDROGEL

(71) Applicants: NAJRAN UNIVERSITY, Najran (SA); XI'AN JIAOTONG UNIVERSITY, Xi'an (CN)

(72) Inventors: Saeed A. Alsareii, Najran (SA); Baolin Guo, Xi'an (CN); Lipeng Qiao, Xi'an (CN); Abdulrahman Manaa Alamri, Najran (SA); Farid A. Harraz, Najran (SA)

(73) Assignees: NAJRAN UNIVERSITY, Najran (SA); XI'AN JIAOTONG UNIVERSITY, Xi'an (CN)

( * ) Notice: Subject to any disclaimer, the term of this patent is extended or adjusted under 35 U.S.C. 154(b) by 0 days.

(21) Appl. No.: 18/898,561

(22) Filed: Sep. 26, 2024

Related U.S. Application Data

(60) Provisional application No. 63/676,675, filed on Jul. 29, 2024.

(51) Int. Cl.
 A61L 26/00 (2006.01)
 A61K 41/00 (2020.01)
 A61L 15/40 (2006.01)

(52) U.S. Cl.
 CPC ........ *A61L 26/008* (2013.01); *A61K 41/0052* (2013.01); *A61L 15/40* (2013.01); *A61L 26/0004* (2013.01); *A61L 26/0095* (2013.01); *A61L 2300/102* (2013.01); *A61L 2300/404* (2013.01)

(58) Field of Classification Search
 CPC .................. A61L 26/008; A61K 41/0052
 See application file for complete search history.

(56) References Cited

FOREIGN PATENT DOCUMENTS

| CN | 116421768 A | 7/2023 |
| CN | 116650710 A | 8/2023 |
| CN | 117797307 A | 4/2024 |

OTHER PUBLICATIONS

Geng, Y. et al., "Recent advances in carboxymethyl chitosan-based materials for biomedical applications", Carbohydrate Polymers, 305 (2023) 120555. (Year: 2023).*

Chi, J. et al., "Novel dopamine-modified oxidized sodium alginate hydrogels promote angiogenesis, and accelerate healing of chronic diabetic wounds", Int'l J of Biological Macromolecules, 203, 2022, 492-504. (Year: 2022).*

Yongliang Ouyang, et al., "Mussel-inspired "all-in-one" sodium alginate/carboxymethyl chitosan hydrogel patch promotes healing of infected wound", International Journal of Biological Macromolecules, vol. 261, Part 2, Mar. 2024, 129828, 8 pages.

(Continued)

*Primary Examiner* — Gina C Justice
(74) *Attorney, Agent, or Firm* — Oblon, McClelland, Maier & Neustadt, L.L.P.

(57) ABSTRACT

A hydrogel includes a polysaccharide including aldehyde groups and carboxy groups, a functionalized chitosan, and iron (III) ions. The hydrogel further includes particles including a core including a carboxy-functionalized polythiophene and a shell including polydopamine. A wound dressing includes the hydrogel and a base layer selected from the group consisting of a gauze, lint, plaster, bandage and cotton wool. The hydrogel is attached or adhered to the base layer.

20 Claims, 51 Drawing Sheets

(56) References Cited

OTHER PUBLICATIONS

Zhongpeng Yu, et al., "Skin-permissible NIR-actuated hyperthermia using a photothermally responsive hydrogel membrane for the effective treatment of antibiotic-resistant bacterial infection", Biomaterials Science, vol. 10, Issue 4, 2022, pp. 960-969, 5 pages.
Oscar Castano, et al., "Instructive microenvironments in skin wound healing: Biomaterials as signal releasing platforms", Advanced Drug Delivery Reviews, vol. 129, Apr. 5, 2018, pp. 95-117.
Min Wang, et al., "Artificial Skin Perception", Advanced Materials, vol. 33, 2021, 2003014, 20 pages.
Xin Zhao, et al., "Physical Double-Network Hydrogel Adhesives with Rapid Shape Adaptability, Fast Self-Healing, Antioxidant and NIR/pH Stimulus-Responsiveness for Multidrug-Resistant Bacterial Infection and Removable Wound Dressing", Advanced Functional Materials, vol. 30, 2030, 1910748, 18 pages.
Angelina D. Schoenenberger, et al., "Macromechanics and polycaprolactone fiber organization drive macrophase polarization and regulate inflammatory activation of tendon in vitro and in vivo", Biomaterials, vol. 249, Apr. 11, 2020, 120034, 14 pages.
Xiaohui Wei, et al., "Polysaccharides-modified chitosan as improved and rapid hemostasis foam sponges", Carbohydrate Polymers, vol. 264, Apr. 3, 2021, 118028, 10 pages.
Mariana F.P. Graca, et al., "Hyaluronic-acid-Based wound dressings: A review", Carbohydrate Polymers, vol. 241, Apr. 27, 2020, 116364, 17 pages.
Moien Alizadehgiashi, et al., "Multifunctional 3D-Printed Wound Dressings", ACS Nano, vol. 15, Jun. 16, 2021, pp. 12375-12387.
Sepehr Talebian, et al., "Self-Healing Hydrogens: The Next Paradigm Shift in Tissue Engineering?" Advanced Science, vol. 6, 2019, 1801664, 47 pages.
Ying Yang, et al., "Self-healing polymeric materials", Chem. Soc. Rev., vol. 42, 2013, pp. 7446-7467.
Yiran Li, et al., "Single-Molecule Mechanics of Catechol-Iron Coordination Bonds", ACS Biomaterials Science & Engineering, vol. 3, May 11, 2017, pp. 979-989.
Xueyu Dou, et al., "Clustering-Triggered Emission and Persistent Room Temperature Phosphorescence of Sodium Alginate", Biomacromolecules, vol. 19, Mar. 20, 2018, pp. 2014-2022.
Wen Yang, et al., "A fluorescent, self-healing and pH sensitive hydrogel rapidly fabricated from HPAMAM and oxidized alginate with injectability", RSC Adv., vol. 6, Mar. 28, 2016, pp. 34254-34260.
Hualjuan Zhou, et al., Microplastic Removal and Degradation by Mussel-Inspired Adhesive Magnetic/Enzymatic Microrobots, Small Methods, vol. 5, 2021, 2100230, 9 pages.
Yongping Liang, et al., "Adhesive Hemostatic Conducting Injectable Composite Hydrogels with Sustained Drug Release and Photothermal Antibacterial Activity to Promote Full-Thickness Skin Regeneration During Wound Healing", Small Journal, vol. 15, 2019, 1900046, 17 pages.
Max Linhorst, et al., "Chitin Deacetylase as a Biocatalyst for the Selective N-Acylation of Chitosan Oligo- and Polymers", ACS Catal., vol. 11, 2021, pp. 14456-14466.
Wenjie Wang, et al., "Chitosan: Structural modification, biological activity and application", International Journal of Biological Macromolecules, vol. 164, Sep. 14, 2020, pp. 4532-4546.
Peggy Chan, et al., "Synthesis and characterization of chitosan-g-poly(ethylene glycol)-folate as a non-viral carrier for tumor-targeted gene delivery", Biomaterials, vol. 28, Sep. 25, 2006, pp. 540-549.
Xue Zhang, et al., "Polymerization and coordination synergistically constructed photothermal agents for macrophages-mediated tumor targeting diagnosis and therapy", Biomaterials, vol. 264, Sep. 12, 2020, 120382, 13 pages.
Jianyu Wang, et al., "Multifunctional Antibacterial Materials for the Control of Hazardous Microbes and Chemicals: A Review", ACS EST Water, vol. 1, Feb. 22, 2021, pp. 479-497.

Pooyan Makvandi, et al., "Metal-Based Nanomaterials in Biomedical Applications: Antimicrobial Activity and Cytotoxicity Aspects", Advanced Functional Materials, vol. 30, 2020, 1910021, 40 pages.
Debjani Banerjee, et al., "A Review on Basic Biology of Bacterial Biofilm Infections and Their Treatments by Nanotechnology-Based Approaches", Proc. Natl. Acad. Sci., India, Section B Biol. Sci. (Apr.-Jun. 2020), vol. 90, No. 2, pp. 243-259.
Yu-Qing Zhao, et al., "Well-Defined Gold Nanorod/Polymer Hybrid Coating with Inherent Antifouling and Photothermal Bactericidal Properties for Treating an Infected Hernia", ACS Nano, vol. 14, Feb. 4, 2020, pp. 2265-2275.
Dong Li, et al., "An Amperometric Biosensor Based on Covalent Immobilization of Ascorbate Oxidase on Biocompatible and Low-Toxic Poly(Thiophene-3-Acetic Acid) Matrix", Chinese Journal of Polymer Science, vol. 30, No. 5, Mar. 12, 2012, pp. 705-718.
Boguang Yang, et al., "Development of Electrically Conductive Double-Network Hydrogels via One-Step Facile Strategy for Cardiac Tissue Engineering", Adv. Healthcare Mater., vol. 5, 2016, pp. 474-488.
Rui Yu, et al., "Conductive Biomaterials as Bioactive Wound Dressing for Wound Healing and Skin Tissue Engineering", Nano-Micro Letters, vol. 14, No. 1, Dec. 2, 2021, 46 pages.
Tippabattini Jayaramudu, et al., "Swelling Behavior of Polyacrylamide-Cellulose Nanocrystal Hydrogels: Swelling Kinetics, Temperature and pH Effects", Materials, vol. 12, Jun. 28, 2019, 14 pages.
Sha Liu, et al., "Absorbable Thioether Grafted Hyaluronic Acid Nanofibrous Hydrogel for Synergistic Modulation o f Inflammation Microenvironment to Accelerate Chronic Diabetic Wound Healing", Advanced Healthcare Materials, vol. 9, 2020, 2000198, 11 pages.
Khurram S. Munir, et al., "Carbon Nanotubes and Graphene as Nanoreinforcements in Metallic Biomaterials: A Review", Advanced Biosystems, vol. 3, 2019, 1800212, 24 pages.
Mingmao Chen, et al., "Dynamic covalent constructed self-healing hydrogel for sequential delivery of antibacterial agent and growth factor in wound healing", Chemical Engineering Journal, vol. 373, May 8, 2019, pp. 413-424.
Jiaoyu Ren, et al., "Double network self-healing film based on metal chelation and Schiff-base interaction and its biological activities", Applied Surface Science, vol. 448, Apr. 12, 2018, pp. 609-617.
Heyuan Huang, et al., "High-strength hydrogels: Fabrication, reinforcement mechanisms, and applications", Nano Research, vol. 16, No. 2, Sep. 29, 2022, pp. 3475-3515.
Ying Huang, et al., "High-strength anti-bacterial composite cryogel for lethal noncompressible hemorrhage hemostasis: Synergistic physical hemostasis and chemical hemostasis", Chemical Engineering Journal, vol. 427, Aug. 24, 2021, 131977, 13 pages.
Zejun Xu, et al., "Advances and Impact of Antioxidant Hydrogel in Chronic Wound Healing", Advanced Healthcare Materials, vol. 9, 2020, 1901502, 11 pages.
D. Gopinath, et al., "Dermal wound healing processes with curcumin incorporated collagen films", Biomaterials, vol. 25, Jul. 14, 2003, pp. 1911-1917.
Meng Li, et al., "Injectable stretchable self-healing dual dynamic network hydrogel as adhesive anti-oxidant wound dressing for photothermal clearance of bacteria and promoting wound healing of MRSA infected motion wounds", Chemical Engineering Journal, vol. 427, Aug. 267, 2021, 132039, 16 pages.
Nurettin Sahiner, et al., "Polydopamine particles as nontoxic, blood compatible, antioxidant and drug delivery materials", Colloids and Surfaces B: Biointerfaces, vol. 172, Sep. 11, 2018, pp. 618-626.
Wei Zhang, et al., "Catechol-functionalized hydrogels: biomimetic design, adhesion mechanism, and biomedical applications", Chem. Soc. Rev., vol. 49, 2020, pp. 433-464.
Huilong Guo, et al., "Injectable Adhesive Self-Healing Multiple-Dynamic-Bond Crosslinked Hydrogel with Photothermal Antibacterial Activity for Infected Wound Healing", Chemistry of Materials, vol. 34, Mar. 10, 2022, pp. 2655-2671.
Chunyan Cui, et al., "Recent advances in wet adhesives: Adhesion mechanism, design principle and applications", Progress in Polymer Science, vol. 116, Mar. 10, 2021, 101388, 34 pages.

(56) References Cited

OTHER PUBLICATIONS

Xianmou Fan, et al., "Mussel foot protein inspired tough tissue-selective underwater adhesive hydrogel", Materials Horizons, vol. 8, 2021, pp. 997-1007.

Chenyang Zhang, et al., "Highly adhesive and self-healing γ-PGA/PEDOT:PSS conductive hydrogels enable by multiple hydrogen bonding for wearable electronics", Nano Energy, vol. 95, Jan. 29, 2022, 106991, 9 pages.

Yongpin Liang, et al., "Functional Hydrogels as Wound Dressing to Enhance Wound Healing", ACS Nano, vol. 15, Aug. 10, 2021, pp. 12687-12722.

Xin Zhao, et al., "Antibacterial anti-oxidant electroactive injectable hydrogel as self-healing wound dressing with hemostasis and adhesiveness for cutaneous wound healing", Biomaterials, vol. 122, Jan. 11, 2017, pp. 34-47.

Jing Chen, et al., "Tailored Hydrogel Delivering Niobium Carbide Boosts ROS-Scavenging and Antimicrobial Activities for Diabetic Wound Healing", Small Journal, vol. 18, 2022, 2201300, 15 pages.

Xin Zhao, et al., "Biomimetic, highly elastic conductive and hemostatic gelatin-rGO-based nanocomposite cryogel to improve 3D myogenic differentiation and guide in vivo skeletal muscle regeneration", Applied Materials Today, vol. 26, Feb. 2, 2022, 101365, 16 pages.

Zhaoyuan Guo, et al., "A Mg2+/polydopamine composite hydrogel for the acceleration of infected wound healing", Bioactive Materials, vol. 15, 2022, pp. 203-213.

Peng Zhao, et al., "Versatile Hydrogel Dressing with Skin Adaptiveness and Mild Photothermal Antibacterial Activity for Methicillin-Resistant Staphylococcus Aureus-Infected Dynamic Wound Healing", Advanced Science, vol. 10, 2023, 2206585, 16 pages.

Xiangyi Yin, et al., "Bio-Multifunctional Hydrogel Patches for Repairing Full-Thickness Abdominal Wall Defects", Advanced Functional Materials, vol. 31, 2021, 2105614, 13 pages.

Lei Wang, et al., "A Novel Double-Crosslinking-Double-Network Design for Injectable Hydrogels with Enhanced Tissue Adhesion and Antibacterial Capability for Wound Treatment", Advanced Functional Materials, vol. 30, 2020, 1904156, 14 pages.

Bahram Saleh, et al., "Local Immunomodulation Using an Adhesive Hydrogel Loaded with miRNA-Laden Nanoparticles Promotes Wound Healing", Small Journal, vol. 15, 2019, 1902232, 15 pages.

Napoleone Ferrara, "VEGF and the quest for tumour angiogenesis factors", Nature Reviews, vol. 2, Oct. 2002, pp. 795-803.

Yuqing Liang, et al., "Dual-Dynamic-Bond Cross-Linked Antibacterial Adhesive Hydrogel Sealants with On-Demand Removability for Post-Wound-Closure and Infected Wound Healing", ACS Nano, vol. 15, Mar. 25, 2021, pp. 7078-7093.

Jin Qu, et al., "Antibacterial adhesive injectable hydrogels with rapid self-healing, extensibility and compressibility as wound dressing for joints skin wound healing", Biomaterials, vol. 183, Aug. 24, 2018, pp. 185-199.

Nadine Wong Shi Kam, et al., "Carbon nanotubes as multifunctional biological transporters and near-infrared agents for selective cancer cell destruction", PNAS, vol. 102, No. 33, Aug. 16, 2005, pp. 11600-11605.

\* cited by examiner

OSD/CMC/Fe/PA1

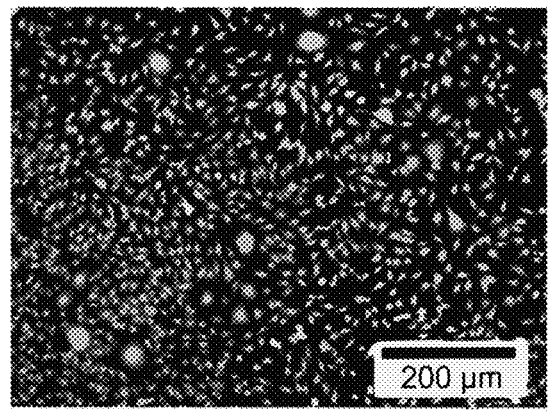
OSD/CMC
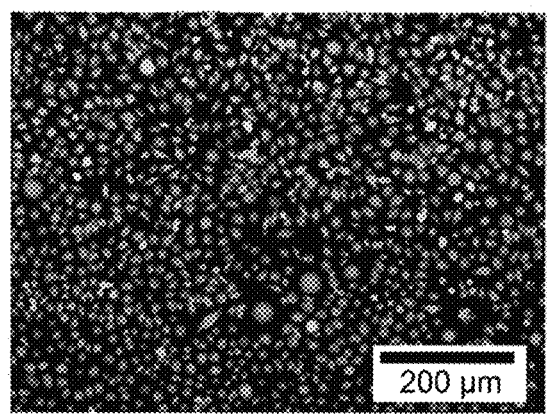
OSD/CMC/Fe
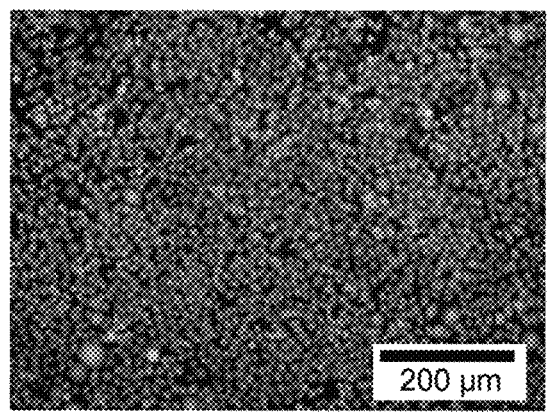
OSD/CMC/Fe/PA3
FIG. 7K-1

OSD/CMC/Fe/PA5

TCP

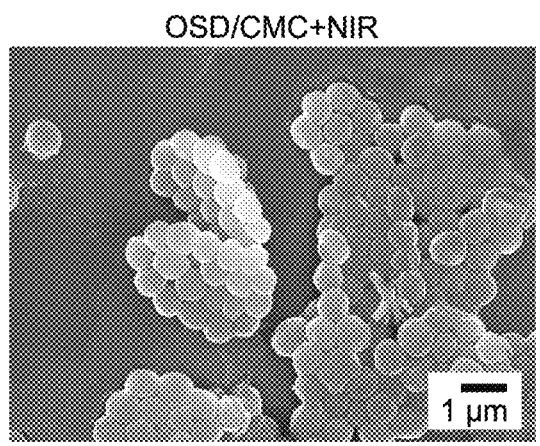
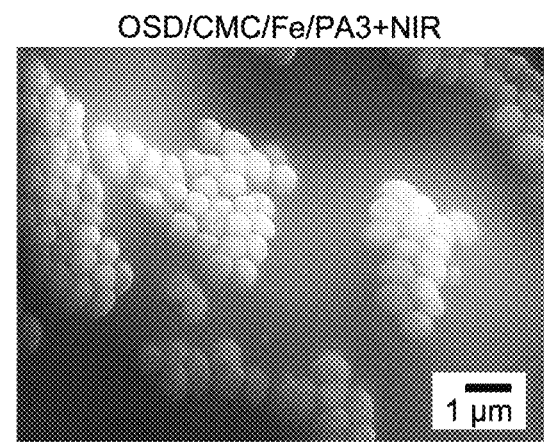
FIG. 10A    FIG. 10B
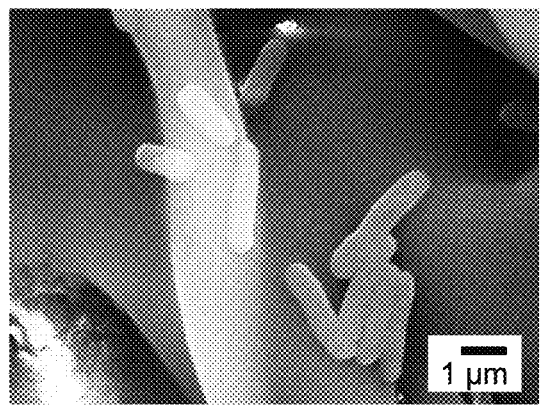
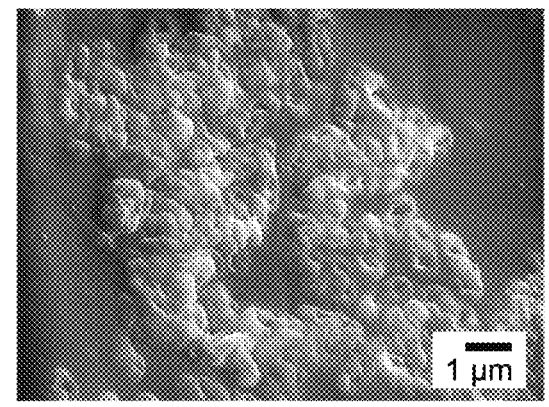
FIG. 10C    FIG. 10D

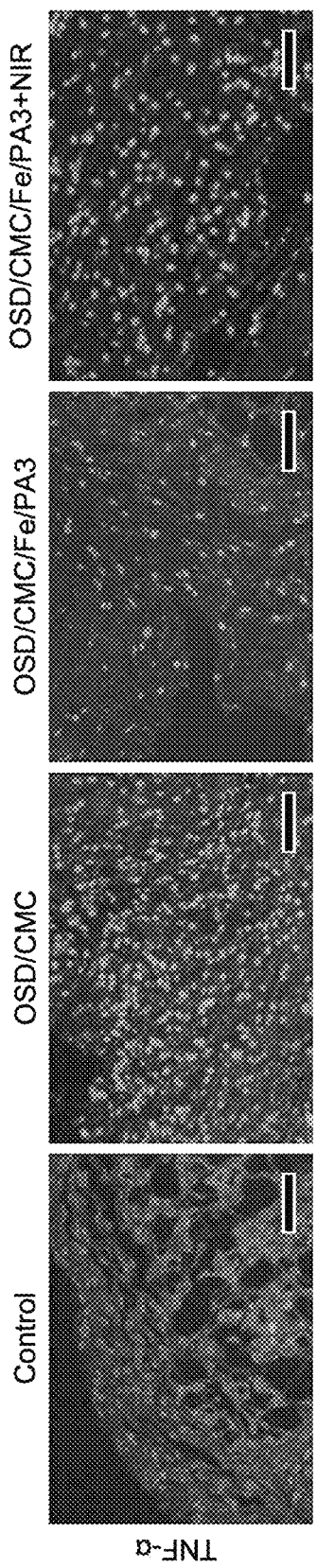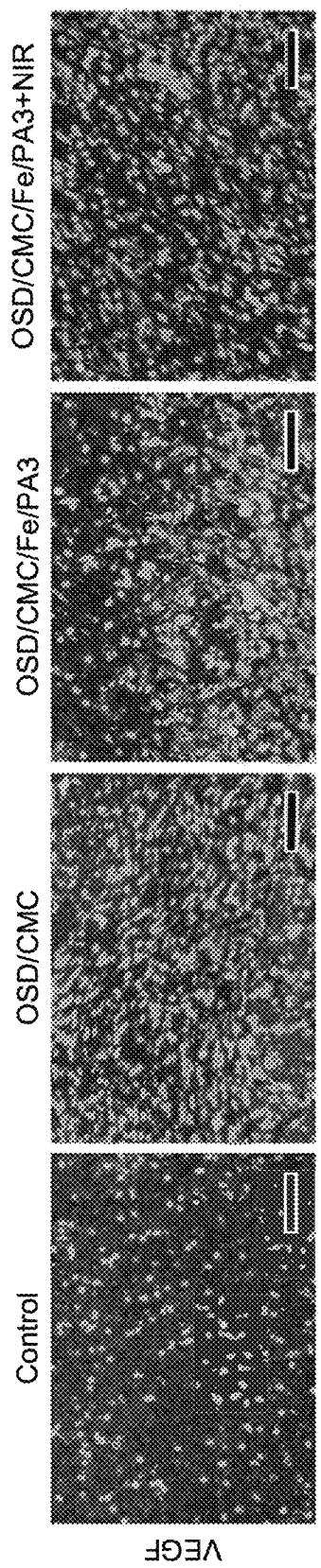
FIG. 13A
FIG. 13B

ANTIBACTERIAL CONDUCTIVE SELF-HEALING HYDROGEL

CROSS REFERENCE TO RELATED APPLICATIONS

The present disclosure claims the benefit of U.S. Provisional Application No. 63/676,675, filed on Jul. 29, 2024, which is incorporated herein by reference in its entirety.

STATEMENT OF PRIOR DISCLOSURE BY AN INVENTOR

Aspects of the present disclosure are described in "Antibacterial conductive self-healing hydrogel wound dressing with dual dynamic bonds promotes infected wound healing" Bioactive Materials 30 (2023) 129-141, which is incorporated herein by reference in its entirety.

BACKGROUND

Technical Field

The present disclosure is directed towards wound dressing solutions, and more particularly, directed towards a hydrogel having antibacterial conductive self-healing properties.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Skin is an essential part of the human body, which is responsible for protecting humans from external aggressors, regulating body temperature, sensing external stimuli and a plurality of other functions. However, since skin is exposed to the outside world, it is vulnerable to various external factors, adversely affecting the skin. In particular, if the skin is damaged, the healing of the skin requires a complex and lengthy process that involves hemostasis, inflammation, hyperplasia and wound remodeling with the formation of scar tissue. In order to promote wound healing, various biomaterials have been developed, such as electrospun fibers, foams and sponges, films, hydrogels, and the like (A. D. Schoenenberger, H. Tempfer, C. Lehner, J. Egloff, M. Mauracher, A. Bird, J. Widmer, K. Maniura-Weber, S. F. Fucentese, A. Traweger, U. Silvan, J. G. Snedeker, *Macromechanics and polycaprolactone fiber organization drive macrophage polarization and regulate inflammatory activation of tendon in vitro and in vivo*, Biomaterials 249 (2020), 120034; X. Wei, S. Ding, S. Liu, K. Yang, J. Cai, F. Li, C. Wang, S. Lin, F. Tian, *Polysaccharides-modified chitosan as improved and rapid hemostasis foam sponges*, Carbohydr. Polym; and M. F. P. Graga, S. P. Miguel, C. S. D. Cabral, I. J. Correia, *Hyaluronic acid-based wound dressings: a review*, Carbohydr. Poly, 264 (2021), 118028). In particular, hydrogel has a three-dimensional network structure, with wound exudate absorption performance, moisturizing ability and oxygen permeability, and has a wide range of promising applications in the area of wound dressing. Further, movement of the wound site may cause tearing or even damage to the dressing, which requires good self-healing properties of the dressing. However, existing hydrogel dressings are difficult to meet such demands. Hence, there is a need to design a hydrogel wound dressing with good self-healing properties. In general, hydrogels with self-healing properties are constructed through dynamic chemical bonds. Schiff base bonds are most widely used to build dynamic networks, which are stronger than disulfide bonds and acylhydrazone (S. Talebian, M. Mehrali, N. Taebnia, C. P. Pennisi, F. B. Kadumudi, J. Foroughi, M. Hasany, M. Nikkhah, M. Akbari, G. Orive, A. Dolatshahi-Pirouz, *Self-healing hydrogels: the next paradigm shift in tissue engineering*, Adv. Sci. 6 (16) (2019), 1801664). Further, Schiff base bonds have the advantages of mild reaction conditions, fast reaction rate, and suitability for biological materials. Furthermore, metal coordination bonds are another commonly used dynamic chemical bond, among which $Fe^{3+}$ and catechol are a relatively common metal coordination system (Y. Yang, M. W. Urban, *Self-healing polymeric materials*, Chem. Soc. Rev. 42 (17) (2013) 7446-7467). The metal coordination bond between catechol and $Fe^{3+}$ may effectively dissipate mechanical energy and is considered a sacrificial bond for load dispersion and impact absorption.

In addition, bacterial infection is another problem in wound repair that may lead to the formation of chronic wounds, and the effectiveness of commonly used antibiotics is greatly reduced by the presence of drug-resistant bacteria. To address this problem, it is vital to design hydrogel dressings with good antibacterial properties. A robust antibacterial strategy must be selected to construct an effective antibacterial hydrogel. Therefore, a need arises for a self-healing hydrogel with good anti-bacterial properties. Accordingly, one object of the present disclosure is to provide a self-healing hydrogel that may circumvent the above-stated drawbacks, such as poor antibacterial activity and poor self-healing characteristics.

SUMMARY

In an exemplary embodiment, a hydrogel is described. The hydrogel includes a polysaccharide including aldehyde groups and carboxy groups, a functionalized chitosan, and iron (III) ions. The hydrogel further includes a core including a carboxy-functionalized polythiophene and a shell including polydopamine.

In some embodiments, the polysaccharide is oxidized sodium alginate having grafted dopamine, the functionalized chitosan is carboxymethyl chitosan, and the carboxy-functionalized polythiophene is poly(thiophene-3-acetic acid).

In some embodiments, the hydrogel includes, based on a total weight of the hydrogel 3 weight percentage (wt. %) to 10 wt. % of the oxidized sodium alginate, 1 wt. % to 5 wt. % of the carboxymethyl chitosan, 0.05 wt. % to 1 wt. % of the iron (III) ions, and 0.25 wt. % to 10 wt. % of the particles.

In some embodiments, the hydrogel includes, based on a total weight of the hydrogel 6 wt. % of the oxidized sodium alginate, 2.7 wt. % of the carboxymethyl chitosan, 0.2 wt. % of the iron (III) ions, and 1 wt. % to 5 wt. % of the particles.

In some embodiments, a storage modulus of the hydrogel is 22% to 56% higher than that of a comparative hydrogel that is the same but does not include the particles, a swelling ratio of the hydrogel is 8% to 20% lower than that of the comparative hydrogel, an electrical conductivity and an adhesive strength of the hydrogel is 46% to 110% higher than that of the comparative hydrogel, and an adhesive strength of the hydrogel to mammalian skin is 43% to 143% higher than that of the comparative hydrogel.

In some embodiments, the hydrogel includes a crosslinked network formed by Schiff bases between the oxidized sodium alginate and the carboxymethyl chitosan and coordination between the iron (III) ions and carboxy groups of the carboxymethyl chitosan and catechol groups of the grafted dopamine, and the particles are dispersed in the crosslinked network.

In some embodiments, the crosslinked network is dynamic in that the hydrogel is configured to self-heal into one piece after being severed into two pieces.

In some embodiments, a number average molecular weight of the oxidized sodium alginate is 4,000 grams per mole (g/mol) to 10,000 g/mol, and a number average molecular weight of the carboxy-functionalized polythiophene is 600 g/mol to 2,000 g/mol.

In some embodiments, the hydrogel has a storage modulus of 50 Pascals (Pa) to 200 Pa, a swelling ratio of 200% to 375%, an electrical conductivity of $1.5 \times 10^{-4}$ to $10 \times 10^{-4}$ $Sm^{-1}$, and an adhesive strength of 2 kPa to 17.5 kPa to mammalian skin.

In some embodiments, the hydrogel has a storage modulus of 94.8 Pa to 120.9 Pa, a swelling ratio of 240% to 266%, an electrical conductivity of $5.0 \times 10^{-4}$ to $7.2 \times 10^{-4}$ $Sm^{-1}$, and an adhesive strength of 5.0 to 8.5 kPa to mammalian skin.

In some embodiments, the hydrogel does not include D-(+)-glucono delta-lactone, polyvinylpyrrolidone, tannic acid, gallic acid or a nanofiber film including fibers of polycaprolactone and polylactic acid on which the hydrogel is disposed.

In some embodiments, the iron (III) ions are in the form of ferric chloride.

In another exemplary embodiment, a method of treating a wound is described. The method includes applying to the wound, a dressing including the hydrogel as mentioned above.

In some embodiments, the dressing further includes a base layer selected from the group consisting of a gauze, lint, plaster, bandage and cotton wool, and the hydrogel is attached or adhered to the base layer.

In some embodiments, the method further includes irradiating the dressing with near-infrared light having a wavelength of 780 nanometers (nm) to 2500 nm for 0.5 minute to 30 minutes.

In some embodiments, the method further includes irradiating the dressing with near-infrared light having a wavelength of 808 nm for 3 minutes to 10 minutes.

In yet another exemplary embodiment, a method of preparing the hydrogel is described. The method includes adding a carboxymethyl chitosan solution, a ferric chloride solution, deionized water and a dispersion of particles to an oxidized sodium alginate solution to form a mixture. The particles include a core including a carboxy-functionalized polythiophene and a shell including polydopamine. The method further includes stirring the mixture to form the hydrogel.

In some embodiments, the method of preparing the hydrogel further includes oxidizing sodium alginate by sodium periodate to form oxidized sodium alginate having aldehyde groups, and grafting dopamine to the oxidized sodium alginate in the presence of 1-(3dimethylaminopropyl)-3-ethylcarbodiimide hydrochloride (EDC) and N-hydroxysuccinyl imine (NHS).

In some embodiments, the method of preparing the hydrogel further includes polymerizing methyl thiophene-3-acetate in the presence of ferric chloride to form poly(methyl thiophene-3-acetate), hydrolyzing the poly(methyl thiophene-3-acetate) to form poly(thiophene-3-acetic acid), and stirring the poly(thiophene-3-acetic acid) and dopamine hydrochloride in an alkaline condition to form the particles.

In some embodiments, the method of preparing the hydrogel further includes dissolving oxidized sodium alginate in phosphate buffered saline (PBS) to form the oxidized sodium alginate solution having a pH of 7.4, dissolving carboxymethyl chitosan in PBS to form the carboxymethyl chitosan solution having a pH of 7.4, dissolving ferric chloride in deionized water to form the ferric chloride solution, and dispersing the particles in PBS to form the dispersion of particles.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings.

FIGS. 5C-1, 5C-2, 5C-3, 5C-4 and 5C-5 show scanning electron microscopy (SEM) images of hydrogels, according to certain embodiments.

FIGS. 7J, 7K-1 and 7K-2 show LIVE/DEAD staining of L929 cells after 24 hours of leachate incubation, according to certain embodiments.

FIG. 10A is a scanning electron microscope (SEM) image showing the bacterial structure and morphology of MRSA after treatment with OSD/CMC+NIR, according to certain embodiments.

FIG. 10B is an SEM image showing the bacterial structure and morphology of MRSA after treatment with OSD/CMC/Fe/PA3+NIR, according to certain embodiments.

FIG. 10C is a SEM image showing the bacterial structure and morphology of E. coli after treatment with OSD/CMC+NIR, according to certain embodiments.

FIG. 10D is an SEM image showing the bacterial structure and morphology of E. coli after treatment with OSD/CMC/Fe/PA3+NIR, according to certain embodiments.

FIG. 13A are optical images of immunofluorescent labeled wound tissue with tumor necrosis factor (TNF-$\alpha$) on day 3, with a scale bar of 50 micrometers ($\mu$m), according to certain embodiments.

FIG. 13B are optical images of immunofluorescent labeled wound tissue with vascular endothelial growth factor (VEGF) on day 7, with a scale bar of 100 $\mu$m, according to certain embodiments.

DETAILED DESCRIPTION

Figure 1A:
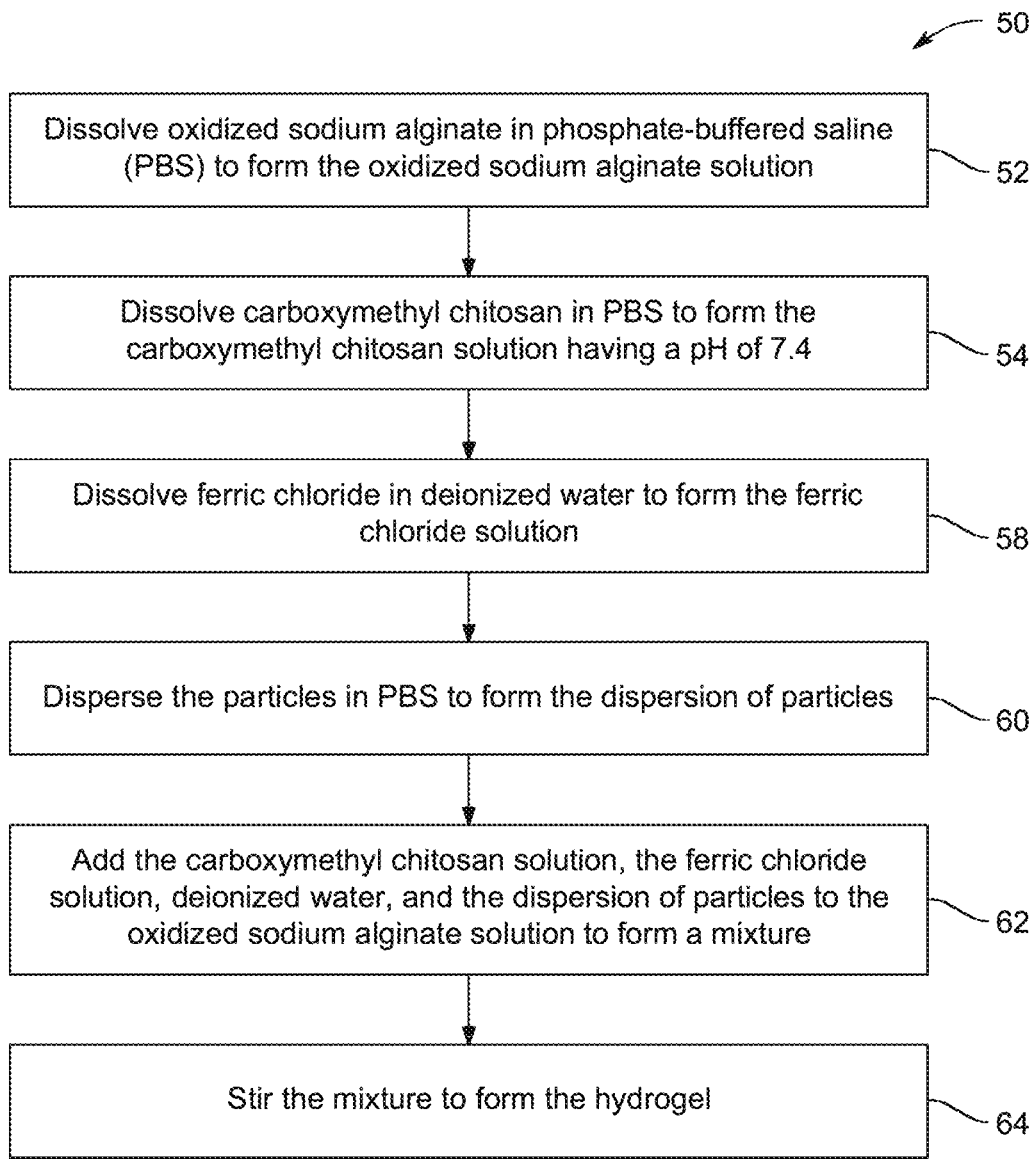
FIG. 1A is a schematic flowchart depicting a method of preparing a hydrogel, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of the present disclosure are directed to an adhesive self-healing conductive antibacterial hydrogel dressings based on oxidized sodium alginate-grafted dopamine/carboxy methylchitosan/Fe$^{3+}$ (OSD/CMC/Fe hydrogel)/polydopamine-encapsulated poly(thiophene-3-acetic acid), also referred to as OSD/CMC/Fe/PA hydrogel, which can be used to repair an infected wound. The hydrogel of the present disclosure has high antibacterial efficiency, suitable conductivity, excellent self-healing properties, good biocompatibility, hemostasis, and antioxidant properties, making it a promising candidate for wound-healing dressings for treating infected skin wounds.

A hydrogel is described. The hydrogel includes at least 4 components—i) a polysaccharide comprising aldehyde groups and carboxy groups; ii) a functionalized chitosan; iii) iron (III) ions; and iv) particles comprising a core comprising a carboxy-functionalized polythiophene and a shell comprising polydopamine.

The polysaccharide includes oxidized sodium alginate and dopamine. Sodium alginate is often used to construct hydrogel materials because it has good biocompatibility, abundant carboxyl groups, and good solubility. Sodium alginate is oxidized to obtain oxidized sodium alginate (OSA). The OSA has aldehyde groups that can significantly improve the ability of sodium alginate to cross-link with other molecules. The OSA has a number average molecular weight of 2,000-20,000 g/mol, preferably 4,000-10,000 g/mol, preferably 6,000-8,000 g/mol. In an embodiment, the sodium alginate is oxidized using an oxidizing agent using methods known in the art. In a specific embodiment, the sodium alginate is oxidized using sodium periodate. In some embodiments, the OSA may be used in conjunction with or substituted with one or more other polysaccharides selected from the group consisting of guar gum, gum arabic, locust bean gum, agar agar, gelatin, whey protein, carrageenan, and xanthan gum. In some embodiments, any of these polysaccharides may be oxidized by methods known in the art to form oxidized polysaccharides with an aldehyde group. The polysaccharide further includes dopamine. Dopamine is a highly adhesive substance secreted by mussels. Under specific conditions, dopamine undergoes self-polymerization to form polydopamine (PDA). PDA with several catechol groups imparts a solid adhesive character. Combining the advantages of the biocompatible and soluble properties of the oxidized sodium alginate and the tissue adhesive property of PDA, the OSA is grafted on dopamine/polydopamine to form the polysaccharide, e.g. oxidized sodium alginate having grafted dopamine (OSD).

The hydrogel further includes functionalized chitosan. Chitosan is the product of the partial deacetylation of natural polysaccharide chitin. It is biodegradable, biocompatible and antibacterial. Yet, its application is limited by its poor water solubility. Chitosan may be functionalized to enhance its solubility in water. Carboxymethyl chitosan (CMC) enhances chitosan's solubility in water by introducing a certain number of hydrophilic carboxyl groups. The amine groups in the CMC react with the aldehyde groups in OSD to form a dynamic Schiff base network.

The hydrogel further includes iron (III) ions. The iron (III) ions can be in the form of ferric chloride, ferric bromide, ferric sulfate, ferric nitrate and the like. In a preferred embodiment, the iron (III) ions are in the form of ferric chloride. The iron (III) ions coordinate with the carboxyl groups and catechol in the OSD to form dynamic bond-metal coordination bonds. The crosslinked network having dual dynamic bonds (Schiff base and bond-metal coordination) endows the hydrogel with good mechanical and self-healing properties as will be explained later. In some embodiments, the iron (III) ions may not be present in the hydrogel.

The hydrogel further includes a photothermal agent. The photothermal antibacterial treatment kills bacteria by using the penetrating power of near-infrared light, thereby solving the problem of serious infections. Suitable examples of photothermal agents include, but are not limited to, gold nanorods, gold nanoshells, thermos nanoarchitectures, graphene and graphene oxide, conjugated polymers like polyaniline (PANI), polypyrrole (PPy), polythiophene (PTh), polydopamine (PDA), donor-acceptor (D-A) conjugated polymers, and poly(3,4-ethylenedioxythiophene): poly(4-styrenesulfonate) (PEDOT: PSS), and/or derivatives thereof. In a preferred embodiment, the photothermal agent includes a carboxy-functionalized polythiophene. Although carboxy-functionalized polythiophene demonstrates good biocompatibility, chemical stability, and photothermal properties, it suffers from poor water solubility. Hence, carboxy-functionalized polythiophene is modified by polymerizing dopamine on its surface to improve its hydrothermal and photothermal properties. The modification results in particles with a core and a shell encapsulating the core. The core includes carboxy-functionalized polythiophene, specifically poly(thiophene-3-acetic acid) (PTAA), and the shell includes polydopamine. The number average molecular weight of the carboxy-functionalized polythiophene is 400-5,000 g/mol, preferably 600-2,000 g/mol, preferably 800-1,600 g/mol, preferably 1,000-1,300 g/mol.

The components of the hydrogel are configured so that a crosslinked network is formed by Schiff bases between the oxidized sodium alginate and the carboxymethyl chitosan and coordination between the iron (III) ions and carboxy groups of the carboxymethyl chitosan and catechol groups of the dopamine grafted to PTAA. The particles are dispersed in the crosslinked network, which is dynamic in that the hydrogel is configured to self-heal into one piece after being severed into two or more pieces.

In some embodiments, the hydrogel includes 3-10 wt. %, preferably 4-8 wt. %, preferably 5-7 wt. %, of the oxidized sodium alginate, 1-5 wt. %, preferably 2-4 wt. %, preferably 2.5-3.5 wt. %, of the carboxymethyl chitosan, 0.05-1 wt. %, preferably 0.1-0.75 wt. %, preferably 0.25-0.5 wt. %, of the iron (III) ions, and 0.25 to 10 wt. %, preferably 1-7.5 wt. %, preferably 2.5-5 wt. %, of the particles based on a total weight of the hydrogel.

In a specific embodiment, the hydrogel includes 6 wt. % of the oxidized sodium alginate, 2.7 wt. % of the carboxymethyl chitosan, 0.2 wt. % of the iron (III) ions, and 1 to 5 wt. % of the particles, based on the total weight of the hydrogel. Such hydrogel has a storage modulus 22%-56% higher than that of a comparative hydrogel that is the same but does not include the particles, a swelling ratio of the hydrogel is 8%-20% lower than that of the comparative hydrogel, an electrical conductivity and an adhesive strength of the hydrogel is 46%-110% higher than that of the comparative hydrogel, and an adhesive strength of the hydrogel to mammalian skin is 43%-143% higher than that of the comparative hydrogel.

In some embodiments, the hydrogel does not include one or more chemical additives selected from the group consisting of D-(+)-glucono delta-lactone, polyvinylpyrrolidone, tannic acid, gallic acid and a nanofiber film comprising fibers of polycaprolactone and polylactic acid on which the hydrogel is disposed.

Although the description provided herein illustrates using the hydrogel for wound dressings, a person skilled in the art may understand that applications of the hydrogel are not limited to wound dressings. For instance, the hydrogel can be adapted to be part of contact lenses, hygiene products, tissue engineering scaffolds, and/or drug delivery systems.

A method of treating a wound is described. As used herein, the term "wound" means any damage to a tissue in a living organism, including human organisms. The tissue may be an internal tissue, such as an internal organ, or an external tissue, such as the skin. The damage may have resulted from a surgical incision or the unintended application of force to the tissue. Wounds include damage caused by mechanical injuries such as abrasions, lacerations, penetrations, and the like, as well as burns and chemical injuries. The damage may also have arisen gradually, such as in an ulcer, lesion, sore, or infection. Examples of wounds include, but are not limited to, contused wounds, incised wounds, penetrating wounds, perforating wounds, puncture wounds, and subcutaneous wounds.

The method includes applying a dressing including the hydrogel to the wound. The dressing includes a base layer and the hydrogel attached or adhered to the base layer. The base layer may include gauze, lint, plaster, bandage, and/or cotton wool. The method further includes irradiating the dressing with near-infrared light with a wavelength of 780 to 2500 nm, preferably 790 to 1500 nm, preferably 790 to 1000 nm, preferably 800 to 900 nm for 0.5-30 minutes, preferably 1-15 minutes, preferably 2-10 minutes, preferably 3-5 minutes. In some embodiments, the wavelength may be outside the suggested ranges; the selection depends on the choice of the photothermal agent. In a specific embodiment, the method includes irradiating the dressing with near-infrared light having a wavelength of 808 nm for 3-10 minutes, preferably 4-9 minutes, preferably 5-8 minutes.

A method of preparing a hydrogel is described. The order in which the method 50 is described is not intended to be construed as a limitation, and any number of the described method steps can be combined to implement the method 50. Additionally, individual steps may be removed or skipped from the method 50 without departing from the spirit and scope of the present disclosure.

At step 52, the method 50 includes dissolving oxidized sodium alginate in phosphate-buffered saline (PBS) to form the oxidized sodium alginate solution, which has a pH of 7-9, preferably 7.2 to 8, preferably 7.4. In an embodiment, the oxidized sodium alginate is obtained by mixing sodium alginate using a suitable oxidizing agent to obtain a solution. In a preferred embodiment, the oxidizing agent is sodium periodate. The weight ratio of sodium alginate to the oxidizing agent, specifically sodium periodate, is in the range of 1:1 to 10:1, preferably 2:1 to 9:1, preferably 3:1 to 8:1, preferably 4:1 to 7:1, preferably 5:1 to 6:1, preferably 5:1. Since sodium periodate is light sensitive, it is preferred to carry on this reaction in the dark. After adding sodium periodate, the solution is mixed at room temperature for 1-5 hours, preferably 2-4 hours, preferably 3-4 hours, preferably 4 hours to allow for complete oxidation of sodium alginate. The reaction may be quenched, preferably after 4 hours, using a suitable quenching agent, to prevent further oxidation. In a preferred embodiment, the quenching agent is ethylene glycol. The oxidized sodium alginate thus obtained is precipitated/filtered by methods known in the art. The oxidized sodium alginate has aldehyde groups.

In some embodiments, the oxidized sodium alginate is grafted onto dopamine to obtain dopamine-grafted oxidized sodium alginate (OSD). The OSD is obtained by initiating an amidation reaction between oxidized sodium alginate and dopamine hydrochloride in a weight ratio of 1:2 to 2:1, preferably about 1.5:1. The amidation reaction is carried out in the presence of a carbodiimide cross-linker. In a preferred embodiment, the cross-linker includes a combination of 1-(3-dimethylaminopropyl)-3-ethylcarbodiimide hydrochloride (EDC) and N-hydroxysuccinyl imine (NHS), although EDC may be used alone as well. The reaction was carried out at a pH of about 4-6, preferably 5-6, preferably about 5.5 at room temperature for 12 hours to 36 hours, preferably 16 to 32 hours, preferably 20 to 28 hours to obtain the OSD. In an embodiment, the OSD was dissolved in the PBS solution. The concentration of OSD in the PBS solution is in the range of 10-20 wt. %, preferably 12-18 wt. %, preferably 13-15 wt. %, preferably about 15 wt. %.

At step 54, the method 50 includes dissolving carboxymethyl chitosan in PBS to form the carboxymethyl chitosan solution. The carboxymethyl chitosan solution has a pH range of 7-9, preferably 7.2 to 8, preferably about 7.4. The concentration of the CMC in the PBS ranges from 1-12 wt. %, preferably 2-10 wt. %, preferably 5-9 wt. %, preferably about 9 wt. %

At step 56, the method 50 includes dissolving ferric chloride in deionized water to form the ferric chloride solution. In an embodiment, the concentration of ferric chloride in the ferric chloride solution is in the range of 0.1-2 wt. %, preferably 0.5-1.5 wt. %, preferably 0.75-1.2 wt. %, preferably 1 wt. %.

At step 58, the method 50 includes dispersing the particles in PBS to form the dispersion of particles. The concentration of the particles in the dispersion is in the range of 0.1-5 wt. %, preferably 0.5-4 wt. %, preferably 1-3 wt. %. Other ranges are also possible. The particles include a core of a carboxy-functionalized polythiophene and a shell of polydopamine that encloses the core. In a specific embodiment, the carboxy-functionalized polythiophene is poly(thiophene-3-acetic acid), and the particles include polydopamine-coated poly(3-thiopheneacetic acid)—where polydopamine forms the shell and poly(3-thiopheneacetic acid) forms the core.

In some embodiments, the method of forming poly(thiophene-3-acetic acid) includes polymerizing methyl thiophene-3-acetate in the presence of ferric chloride to form poly(methyl thiophene-3-acetate) and hydrolyzing the poly(methyl thiophene-3-acetate) to form poly(thiophene-3-acetic acid). In some embodiments, the poly(thiophene-3-acetic acid) may be prepared by any method known in the art. In some embodiments, the poly(thiophene-3-acetic acid) is coated with dopamine. The polydopamine-coated poly(3-thiopheneacetic acid) is obtained by stirring the poly(thiophene-3-acetic acid) and dopamine hydrochloride in an alkaline condition (pH in a range of 7-9, preferably 7.5 to 8.5) for 24-48 hours, preferably 36-40 hours, to form the particles of polydopamine-coated poly(3-thiopheneacetic acid).

At step 60, the method 50 includes adding the CMC solution, the ferric chloride solution, deionized water, and the dispersion of particles to the oxidized sodium alginate solution to form a mixture. In an embodiment, the method includes adding the CMC solution, the ferric chloride solution, deionized water, and the dispersion of particles to the OSD solution to form the mixture.

At step 62, the method includes stirring the mixture to form the hydrogel. The mixture was stirred using a stirrer to form the hydrogel. The hydrogel has a storage modulus of 50 to 200 Pa, a swelling ratio of 200% to 375%, an electrical conductivity of $1.5 \times 10^{-4}$ to $10 \times 10^{-4}$ $Sm^{-1}$, and an adhesive strength of 2 to 17.5 kPa to mammalian skin. In a specific embodiment, the hydrogel has a storage modulus of 94.8 to 120.9 Pa, a swelling ratio of 240% to 266%, an electrical conductivity of $5.0 \times 10^{-4}$ to $7.2 \times 10^{-4}$ $Sm^{-1}$, and an adhesive strength of 5.0 to 8.5 kPa to mammalian skin.

EXAMPLES

The following examples are provided solely for illustration and are not to be construed as limitations of the present disclosure, as many variations thereof are possible without departing from the spirit and scope of the present disclosure.

Example 1: Materials

Sodium alginate (SA) was obtained from Aladdin. Dopamine hydrochloride (DA) and 3-thienylacetic acid (TAA) was obtained from J&K. 1-(3-dimethylaminopropyl)-3-ethylcarbodiimide hydrochloride (EDC), N-hydroxysuccinylimine (NHS) and carboxymethyl chitosan (CMC) were obtained from Macklin. Sodium periodate ($NaIO_4$) and ferric chloride were obtained from Sigma-Aldrich. The reagents were analytically pure and not further purified.

Example 2: Synthesis of Poly(3-Thiopheneacetic Acid)

Figure 1B:
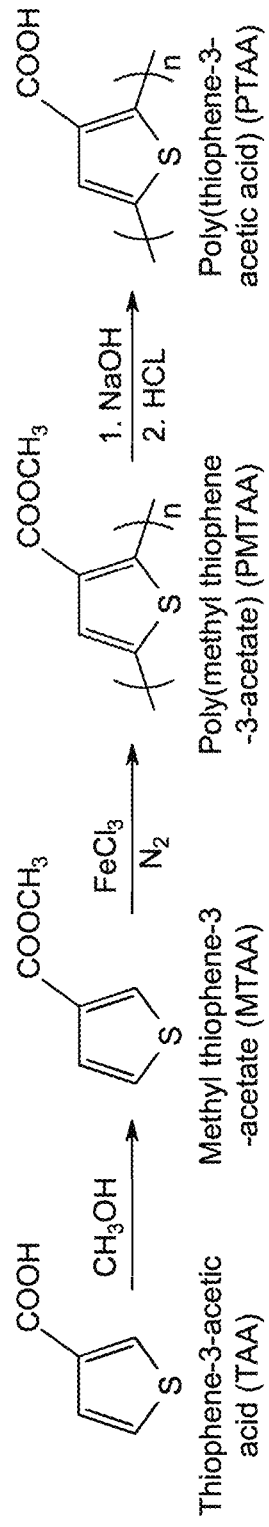
FIG. 1B is a reaction scheme depicting the synthesis of poly(3-thiophene acetate), according to certain embodiments.

As shown in FIG. 1B, 50 milliliter (mL) methanol was added into a 100 mL round bottom flask, and 4.9763 g thiophene-3-acetic acid was added under the protection of nitrogen gas ($N_2$). A catalytic amount of concentrated sulfuric acid was slowly added and stirred at room temperature. After 24 hours (h) of reaction, the solvent was evaporated, extracted with ether and deionized water, and dried with anhydrous sodium sulfate to obtain a yellow oily product, methyl thiophene-3-acetate. Then, 30 mL chloroform was added to a 100 mL three-necked flask. Under an inert $N_2$ environment, anhydrous ferric chloride with a catalytic amount was added at 0° C. and stirred for 20 minutes to obtain a dark green turbid liquid. 5.4674 g methyl thiophene-3-acetate ester dissolved in 20 mL chloroform was added dropwise within 10 minutes. After 24 h of reaction, the reactants were slowly poured into 300 mL methanol for standing and suction filtration. The filter cake was repeatedly washed with deionized water and vacuum dried at 50° C. for 10 h. Then, Soxhlet extraction was performed using methanol and acetone, respectively. Poly(methyl thiophene-3-acetate) was obtained. Finally, 5.4674 g poly(methyl thiophene-3-acetate) was added to 50 mL 2 mol/L NaOH solution, hydrolyzed at 100° C. for 24 h, and the insoluble matter was filtered to obtain a transparent red poly(sodium thiophene-3-acetate) solution. Hydrochloric acid was slowly added under continuous stirring until a yellow flocculent precipitate appeared, and then dialysis was performed in 0.1 mol/L hydrochloric acid solution for 5 days ($M_w$=500). The dialysis product was freeze-dried to obtain black pure poly(3-thiophene acetate) or PTAA or PA (FIG. 1B).

Example 3: Synthesis of Oxidized Sodium Alginate (OSA)

Figure 1C:
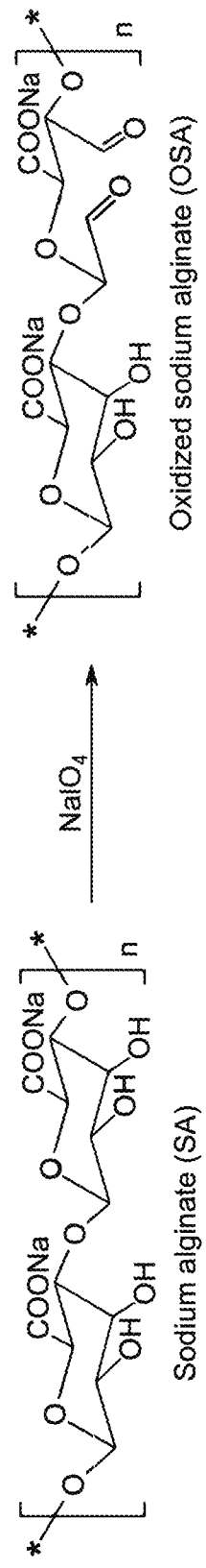
FIG. 1C is a reaction scheme depicting the synthesis of oxidized sodium alginate (OSA), according to certain embodiments.
Figure 3:
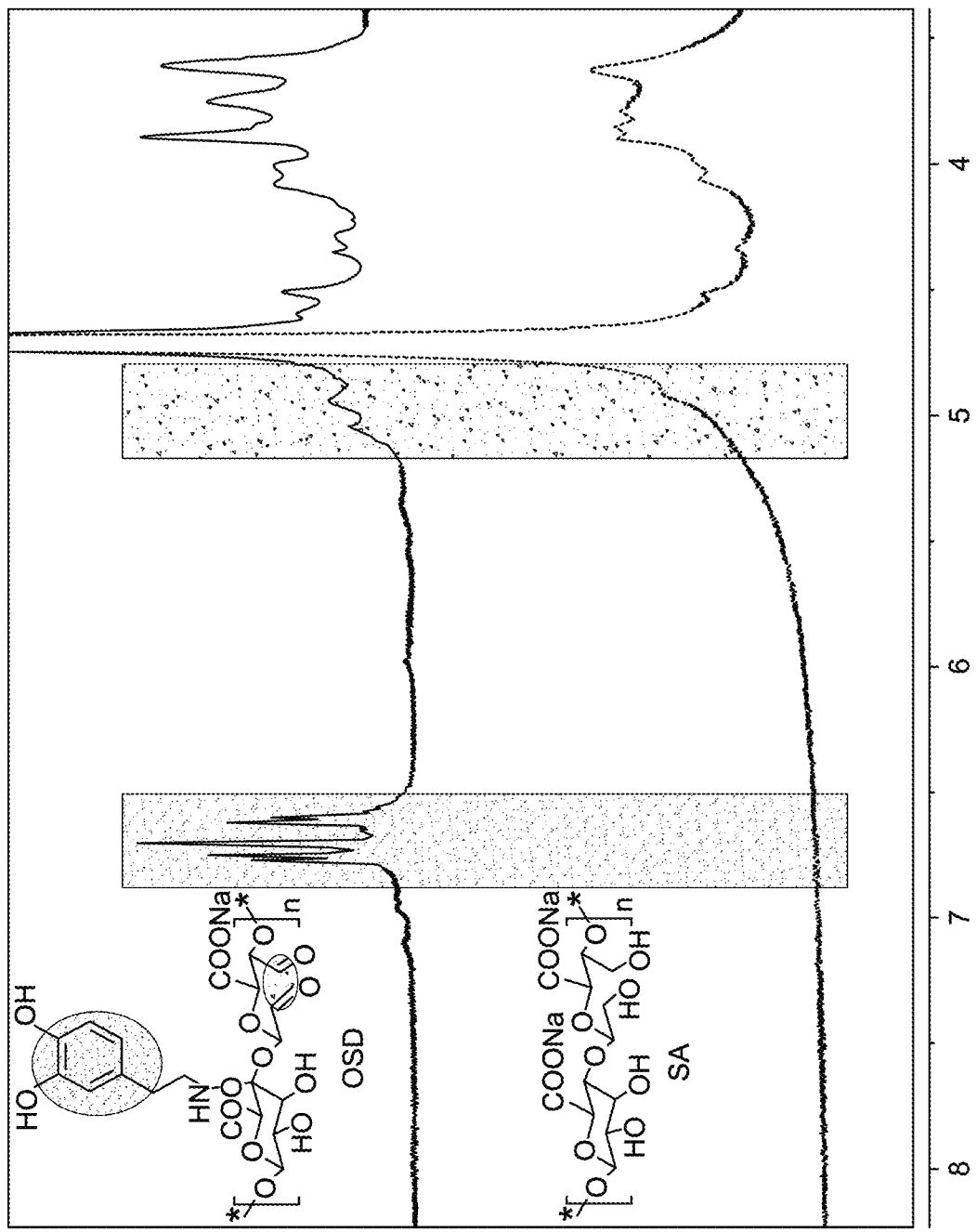
FIG. 3 depicts proton nuclear magnetic resonance ($^1$H NMR) spectra of sodium alginate (SA) and OSD, according to certain embodiments.

As shown in FIG. 1C, 3 grams (g) of sodium alginate was dissolved in 300 mL deionized water and magnetically stirred to completely dissolve to prepare a 1 weight percent (wt. %) solution. Subsequently, 0.6484 g of sodium periodate was added in the dark at 25° C. for 4 h, and 3 mL of ethylene glycol was added to terminate the reaction for 2 h. Further, 1 g of NaCl was added, and 100 mL of ethanol was added to precipitate it. A white product was obtained by vacuum filtration. After being dissolved with 100 mL of deionized water, the solution was put into a dialysis bag ($M_w$=3500) for dialysis for 3 days, and the water was changed 3 to 4 times a day. Furthermore, the product was freeze-dried to obtain a white OSA product, as observed in FIG. 1C.

Example 4: Synthesis of Dopamine-Grafted Oxidized Sodium Alginate (OSD)

Figure 1D:
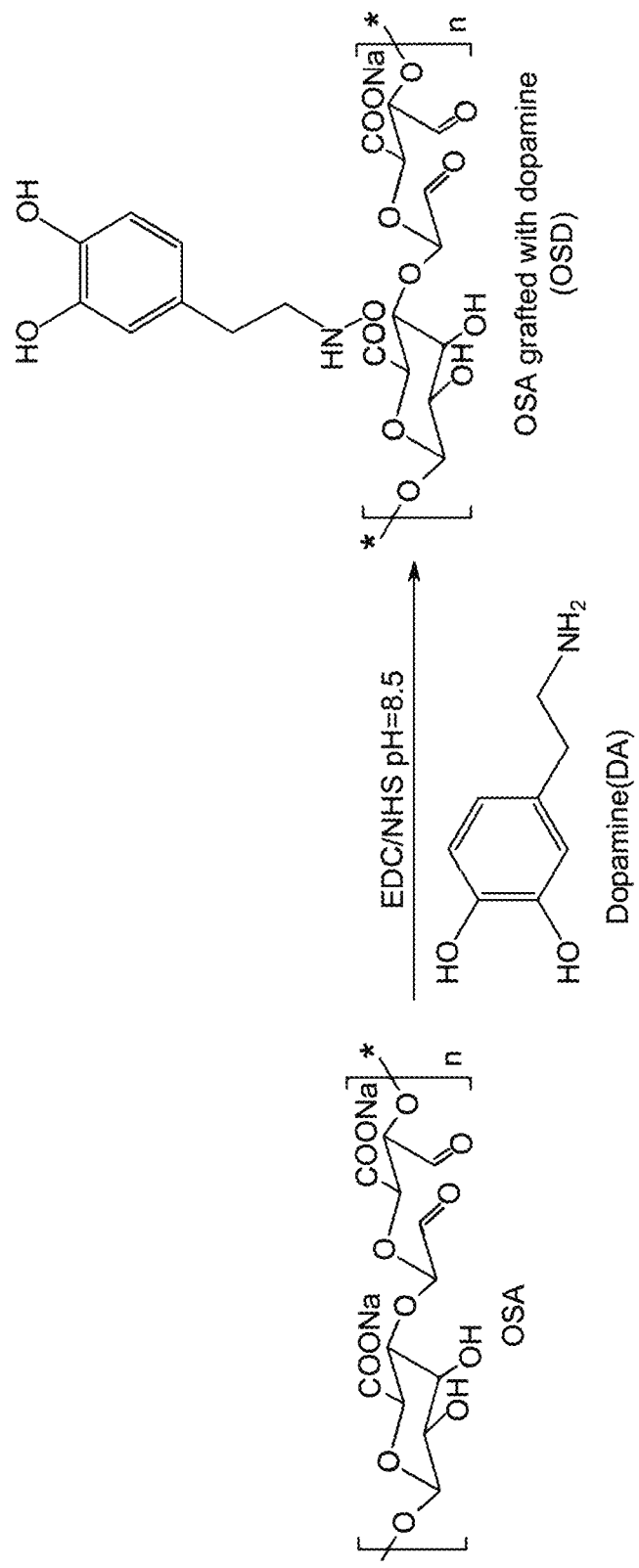
FIG. 1D is a reaction scheme depicting the synthesis of dopamine-grafted oxidized sodium alginate (OSD), according to certain embodiments.

As shown in FIG. 1D, 3 g of oxidized sodium alginate was dissolved in 300 mL deionized water. 2.71 g of 1-ethyl-(3-dimethylaminopropyl) carbodiimide, and 1.63 g of N-hydroxysuccinimide were added under an inert $N_2$ environment for 15 minutes, and then 2.0 g of dopamine hydrochloride was added to initiate the amidation reaction. During the reaction, the pH was adjusted to about 5.5 to make the solution slightly pink, and the pH of the solution was monitored every half hour to make it stable in the range. After 12 hours of reaction at 25° C., the reaction solution was placed in a dialysis bag ($M_w$=3500) and dialyzed with pH=5.5 buffer for three days. The dialysis product was freeze-dried to obtain a dopamine-grafted oxidized sodium alginate product (FIG. 1D).

Example 5: Synthesis of Polydopamine-Coated Poly(3-Thiopheneacetic Acid) or PTAA@PDA 300 milligrams (mg) of poly(thiophene-3-acetic acid) was added to a 500 mL round-bottom flask, dispersed with 300 mL of tris-HCl buffer (pH=8.5). After magnetic stirring for 5 min, 600 mg DA was added to the flask, and the pH was adjusted to more than 8.5 for 48 h at room temperature. Further, the reaction solution was centrifuged at 6000 revolutions per minute (rpm) to obtain a dopamine-coated poly (3-thiophene acetate) precipitate. The transmission electron microscope image of the polydopamine-coated poly(3-thiopheneacetic acid) is presented in FIG. 1F.

Example 6: Preparation of OSD/CMC/Fe/PA Hydrogels

Figure 1E:
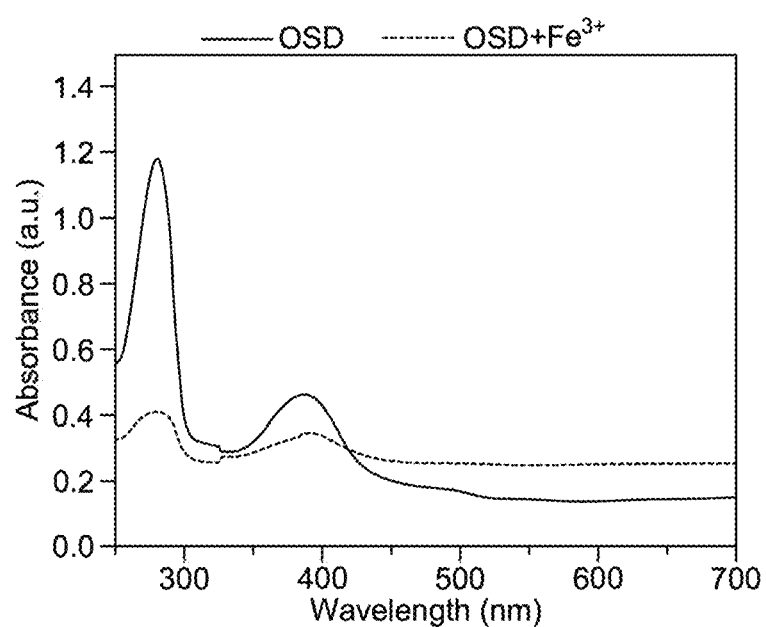
FIG. 1E depicts comparative UV-absorption spectra of the OSD in the presence and absence of $Fe^{3+}$, according to certain embodiments.
Figure 1F:
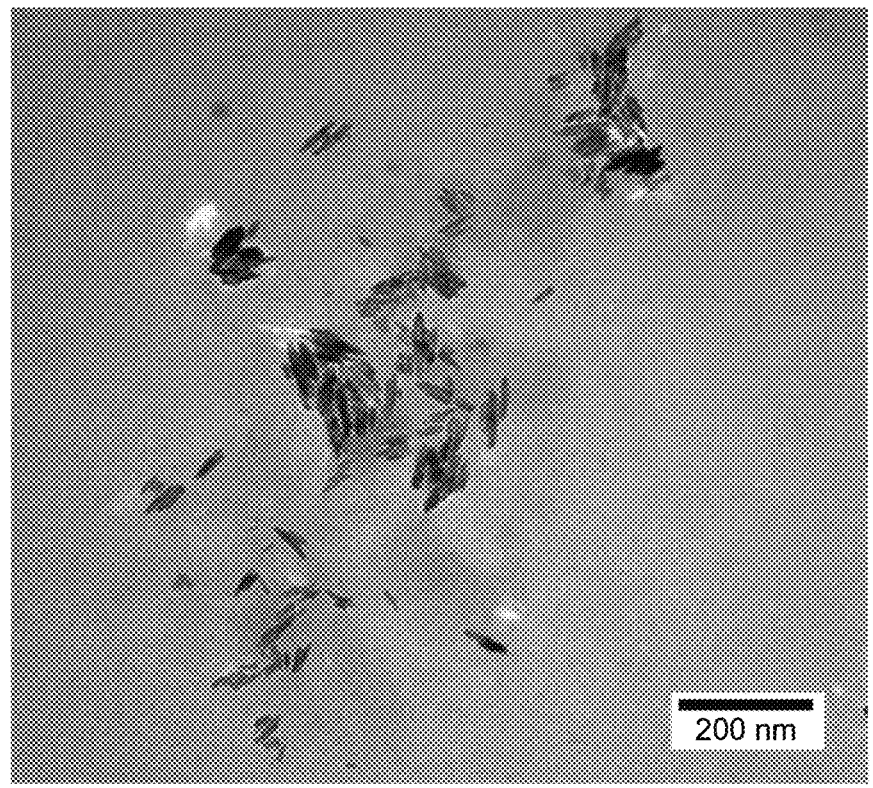
FIG. 1F is a transmission electron microscope (TEM) image of polydopamine-coated poly(3-thiopheneacetic acid) or PTAA@PDA or PA, according to certain embodiments.

To prepare 1 mL of OSD/CMC/Fe/PA hydrogels, OSD was first dissolved in pH=7.4 PBS to form a 15 wt. % solution. CMC was dissolved in pH=7.4 PBS to form a 9 wt. % solution. Ferric chloride was dissolved in deionized water to form a 1 wt. % solution and PA were dispersed in PBS to form a 6 wt. % dispersion. 400 μL of 15 wt. % OSD solution was added, followed by 300 L of 9 wt. % CMC solution, 200 μL of 1 wt. % ferric chloride solution, and various amounts of deionized water and PA dispersion under constant stirring to form a reddish-brown or black hydrogel. According to the presence or absence of $Fe^3$ and the amount of PA added, they were named OSD/CMC, OSD/CMC/Fe, OSD/CMC/Fe/PA1 (1 wt. % PA), OSD/CMC/Fe/PA3 (3 wt. % PA), and OSD/CMC/Fe/PA5 (5 wt. % PA). The UV-absorption spectra of the OSD in the presence and absence of $Fe^{3+}$ are compared and the results are depicted in FIG. 1E.

Example 7: Swelling and Biodegradation Behavior of OSD/CMC/Fe/PA Hydrogels

Firstly, the hydrogels were placed in a sealed tube containing PBS (pH=7.4) at 37° C. to mimic the physiological conditions. After that, the hydrogels were removed at regular intervals, and the hydrogels' mass was weighed after the surface water was wiped with filter paper, and the above process was repeated until the weight of the hydrogels was stable. Finally, the swelling ratios of hydrogels were calculated according to the swelling mass. The experiment was repeated 4 times for each sample, and the average value was calculated. The calculation formula of the swelling ratio was as follows: $S_R=(W_t-W_0)/W_0 \times 100\%$, where $S_R$ is the swelling ratio; $W_t$ is the weight of hydrogel after swelling for a specific time; and $W_0$ is the weight of the initial hydrogel.

The biodegradation behavior of OSD/CMC/Fe/PA hydrogels was evaluated in a wet state after the hydrogels reached swelling equilibrium. The hydrogels were placed in a sealed tube containing PBS (pH=7.4) at 37° C. to mimic the physiological conditions. After that, the hydrogels were removed at regular intervals, and the hydrogels' mass was weighed after the surface water was wiped with filter paper. The process above was repeated until the hydrogels were biodegraded entirely. Finally, the biodegradation ratios of hydrogels were calculated according to the remaining weight of the hydrogels. The experiment was repeated four times for each sample, and the average value was calculated. The calculation formula of biodegradation rate was as follows: $D_R=(W_S-W_D)/W_S \times 100\%$, where $D_R$ is the degradation ratio; $W_D$ is the weight of hydrogel after degradation for a specific time; and $W_S$ is the hydrogel weight with swelling equilibrium.

Example 8: Conductivity Testing of OSD/CMC/Fe/PA Hydrogels

According to the reference [W. Wang, Z. Li, H. Xu, L. Qiao, X. Zhang, Y. Zhao, Z. Dong, H. Huang, X. Zhao, B. Guo, *Highly stretchable, shape memory* and *antioxidant ionic conductive degradable elastomers for* strain *sensing with high sensitivity* and *stability, Mater. Des.* 222 (2022) 111041, incorporated herein by reference in its entirety], the hydrogels were machined into cylinders with a diameter of 20 mm and a thickness of 3 mm. The conductivity of the different hydrogels was measured using a digital multimeter (Agilent), and the data was recorded using Keysight software. The conductivity was calculated according to equation (1)

$$1/\rho = L/RS \qquad (1)$$

where $\rho$ is the conductivity of the hydrogel film; L is the length of the hydrogel film; R is the resistance of the hydrogel film; and S is the cross-sectional area of the hydrogel.

Example 9: Rheological and Self-Healing Properties Test of OSD/CMC/Fe/PA Hydrogels The rheological and self-healing properties of the OSD/CMC/Fe/PA hydrogels were evaluated by TA Rheometer (DHR-2) by the method reported [Y. Huang, L. Mu, X. Zhao, Y. Han, B. Guo, *Bacterial Growth-Induced Tobramycin Smart Release Self-Healing Hydrogel for Pseudomonas aeruginosa-Infected Burn Wound Healing, ACS Nano* 16(8) (2022) 13022-13036, incorporated herein by reference in its entirety]. In brief, the 350 µL hydrogels were made into round sheets with a diameter of 20 mm and a thickness of 1 mm, and the hydrogels were placed between parallel plates within the rheology experiment. The stiffness of different hydrogels was studied by the time sweep test with the frequency of 1 Hz, and the deformation was 1%. After the rheology test of the hydrogel, the above complete hydrogels were also employed to measure the maximum critical strain that the hydrogels could withstand by the strain amplitude scanning test ($\gamma$=1-1000%) at 25° C. with the constant frequency of 1 rad/s. Finally, according to the maximum critical strain of the hydrogels, the self-healing abilities of the hydrogels were also evaluated by the freshly prepared hydrogels with the same shape as the above experiments. The self-healing experiment was performed by alternating strain scanning at a fixed angular frequency of 1 rad/s at 25° C. During the test, the amplitude oscillation strain switched between the minimum strain $\gamma$=0.1% and the maximum strain above the maximum critical strain that the hydrogels could withstand ($\gamma$=274%) with 120 s time interval of each strain test, and the total cycle is six times.

Example 10: Antioxidant Efficiency of OSD/CMC/Fe/PA Hydrogels

The antioxidant efficiency of the OSD/CMC/Fe/PA hydrogels was assessed by their scavenging ability of stable 1,1-diphenyl-2-picrylhydrazyl (DPPH) free radicals. Briefly, the hydrogels (200 µL) were prepared in sealed tubes and made into homogenate using a tissue grinder. After that, the DPPH (100 µM) dissolved in 3.0 mL of ethanol was added into the sealed tubes and mixed with the hydrogel homogenate thoroughly, then the mixture was incubated in a light-proof shaker at 37° C. for 30 min, and 100 µM of ascorbic acid (VC) was used as a positive control. Wavelength scanning was performed using a UV-vis spectrophotometer. The DPPH degradation was calculated using the following equation:

DPPH scavenging (%)=$(A_B-A_H)/A_B \times 100\%$, where $A_B$ was the absorption of the blank(DPPH+ethanol), and $A_H$ was the absorption of the film (DPPH+ethanol+hydrogels).

Example 11: Tissue Adhesion Capacity of OSD/CMC/Fe/PA Hydrogels

The adhesive strength test of hydrogel was conducted based on literature [Y. Liang, X. Zhao, T. Hu, B. Chen, Z. Yin, P. X. Ma, B. Guo, *Adhesive Hemostatic Conducting Injectable Composite Hydrogels with Sustained Drug Release and Photothermal Antibacterial Activity to Promote Full-Thickness Skin Regeneration During Wound Healing, Small* 15(12) (2019) 1900046, incorporated herein by reference in its entirety]. Briefly, the adhesive ability of the hydrogels to the host tissue was evaluated using fresh porcine skin. The skin tissue was cut into 10 mm×40 mm rectangles and immersed in PBS before use. Then 100 µL of OSD/CMC/Fe/PA hydrogel prepolymer solutions were applied onto the surface of the porcine skin, and another piece of porcine skin was put onto the hydrogel solution. The adhesive area was 10 mm×10 mm. Subsequently, the porcine skin was placed at room temperature for 30 min. The adhesion properties were tested using the lap shear test on a Materials Test system (MTS Criterion 43, MTS Criterion) equipped with a 50 N load cell at a rate of 2 mm/min. All these tests were employed more than five times.

Example 12: In Vivo Hemostatic Performance of OSD/CMC/Fe/PA Hydrogels

According to the reference [Y. Liang, X. Zhao, T. Hu, B. Chen, Z. Yin, P. X. Ma, B. Guo, *Adhesive Hemostatic Conducting Injectable Composite Hydrogels with Sustained Drug Release and Photothermal Antibacterial Activity to Promote Full-Thickness Skin Regeneration During Wound Healing, Small* 15(12) (2019) 1900046, incorporated herein by reference in its entirety], a hemorrhaging liver mouse (Kunming mice, 20-30 g, female) was employed to evaluate the hemostatic potential of the OSD/CMC/Fe/PA hydrogels. Briefly, by injecting 10 wt. % chloral hydrate, a mouse was anesthetized and then fixed on a surgical corkboard. The liver of the mouse was exposed by an abdominal incision, and serous fluid around the liver was removed. A pre-weighted filter paper on a paraffin film was placed beneath the liver. Bleeding from the liver was induced using a 20 G needle with the corkboard tilted at about 30°, and 50 mL of OSD/CMC/Fe/PA hydrogel solution was immediately applied to the bleeding site using the syringe. Ten minutes later, the weight of the filter paper with absorbed blood was measured and compared with a control group (no treatment after pricking the liver).

Example 13: Whole Blood Clotting Test of OSD/CMC/Fe/PA Hydrogels

The whole blood clotting capability of OSD/CMC/Fe/PA hydrogels was assessed by referring to work [X. Zhao, Y. Liang, B. Guo, Z. Yin, D. Zhu, Y. Han, *Injectable dry cryogels with excellent blood-sucking expansion and blood clotting to cease hemorrhage for lethal deep-wounds, coagulopathy and tissue regeneration*, Chem. Eng. J. 403 (2021) 126329, incorporated herein by reference in its entirety]. In brief, 200 μL of a hydrogel precursor solution was added to the bottoms of 10 mL sealed tubes. After the hydrogel precursor was completely gelled, the rat whole blood for 50 μL after recalcification by $CaCl_2$ (0.2 M, 10 mM) was slowly dripped onto the surface of the hydrogels, and the sealed tubes were incubated at 37° C. for 10 min. Then, the deionized water (10 mL) was added to each tube to re-suspend uncoagulated blood without destroying the original clot. Then, the supernatants in the tubes were removed and a microplate reader (Molecular Devices) detected their absorbance at 540 nm. Meanwhile, the blood clotting properties of the gelatin sponge were evaluated as the controls. The reference value according to the absorbance of untreated 50 μL recalcified whole blood was incubated at the same time (negative control), and the untreated 50 μL recalcified whole blood with unincubated was set as blank. The following equation evaluated the whole blood clotting properties of the hydrogels: Blood Clotting Index (BCI)=[(As−Ao)/(Ab−Ao)]×100%, where "As" means the absorbance of the supernatants in sample groups; "Ab" represented the absorbance of the supernatants of the blank control; and "Ao" represented the absorbance of the DI water. All the above examinations have 5 replicates.

Example 14: The Cytocompatibility of OSD/CMC/Fe/PA Hydrogels

Cytocompatibility testing is a way to test the cytocompatibility of the material, which needs to be in contact with skin tissue or in vivo tissue during application, and the toxicity of the leachate of the material was tested. Different hydrogels were sterilized, and the mass of the hydrogel was weighed and soaked in DMEM at a concentration of 10 mg/mL for 24 hours, then, the leaching solution was filtered using a sterile filter, and 10% serum was added. A leaching solution of different hydrogel was added to the 96-well plate seeded with L929 cells (10,000 cells/well) and placed in a 37° C. humidified incubator containing 5% $CO_2$ for culture. After 24 hours, the leaching solution was removed, and 100 μL of working solution (V (alamarBlue®): V (complete medium)=1:9) was added to each well. The plate was incubated in an incubator at 37° C. for 4 hours. Then, 90 μL of working solution from each well was transferred to a 96-well black plate (Costar). Next, each well was rinsed twice with PBS, added with Live/Dead working solution, and incubated in an incubator for 40 minutes. Fluorescence was read in a black 96-well plate in a microplate reader (Molecular Devices) using 560 nm as excitation wavelength and 600 nm as emission wavelength. Cells seeded on TCP without leaching solution served as a positive control. The test was repeated four times for each group. Cell viability was observed under an inverted fluorescence microscope (IX53, Olympus).

Example 15: Hemocompatibility Test of OSD/CMC/Fe/PA Hydrogels

The hemocompatibility of OSD/CMC/Fe/PA hydrogels was assessed by red blood cells of the mouse. In brief, the red blood cells were obtained by centrifuging the blood of the mouse at 1000 rpm for 10 min. Then, the obtained red blood cells were washed with PBS 3 times and diluted to a final concentration of 5% (v/v). 200 μL of hydrogels was prepared in a 48-well plate at 37° C., and 1 mL of mouse red blood cells suspension was added to each well. After the 48-well plate was incubated at 37° C. for 1 h, the suspension was transferred to the centrifuge tube for centrifugation at 1000 rpm for 10 min. After centrifugation, the supernatant was transferred to a 48-well plate of 100 μL per well, and the absorbance of the supernatant was read at 540 nm through the microplate reader (Molecular Devices). In addition, the 0.1% Triton X-100 was used as the positive control and PBS as the negative control. Each experiment was repeated three times. Calculate the hemolysis percentage according to the formula:

Hemolysis (%)=[($A_p$−$A_b$)/($A_t$−$A_b$)]×100%, where $A_p$ is the absorbance value of the hydrogel group; $A_t$ was the absorbance value of the positive control Triton X-100; and $A_b$ is the absorbance value of PBS.

Example 16: Photothermal Behavior, Photothermal Enhanced In Vitro and In Vivo Antibacterial Property of OSD/CMC/Fe/PA Hydrogels The photothermal capability of the OSD/CMC/Fe/PA hydrogels was assessed by a Near-Infrared (NIR) laser with a wavelength of 808 nm. Briefly, the different hydrogels were prepared in tubes, and the NIR light was hit on the hydrogel surface. Then, the temperature around the irradiation spot in the hydrogel's surface was recorded with a visual thermometer until the temperature stopped rising. The temperature-time curves were used to evaluate the photothermal properties of hydrogels. As for the cycle photothermal test of the hydrogels, the NIR light was applied on the hydrogel surface. After the temperature of the hydrogels surface reached its peak, the NIR light was removed and waited for the surface temperature of the hydrogel to drop to room temperature. The surface temperature of the hydrogel during the whole process was recorded with a visual thermometer, and the process above was repeated for 3 times.

After photothermal evaluation, the in vitro antibacterial property enhanced by photothermal treatment of hydrogels was tested following the method: hydrogel blocks (5×5×5 mm) were prepared in a sterile environment and placed in sterile 24-well plates. Then, 10 μL of bacterial suspension ($10^8$ CFU/mL) was added to each hydrogel surface by dropping, and the hydrogels were irradiated for 0, 1, 3, 5, and 10 min with an NIR laser (808 nm, 1.4 W/cm²). After irradiation, 1 mL of sterile PBS was added to each well to re-suspend the surviving bacteria. Then L of the re-suspended bacterial solution was added to the plate and incubated at 37° C. for 18 to 24 h to calculate the colony on the plate. Moreover, 10 μL of the bacterial suspension ($10^8$ CFU/mL) in 1 mL of sterile PBS was also irradiated at the same time by the NIR laser (808 nm, 1.4 W/cm$^2$) set as a negative control. All these tests were performed 5 times.

For the in vivo NIR irradiation-enhanced antibacterial performance test, female Kunming mice weighing 25-35 g and 5-6 weeks of age were chosen. All mice were randomly divided into 4 groups, including control, OSD/CMC hydrogel, OSD/CMC/Fe/PA3 hydrogel, and OSD/CMC/Fe/PA3 hydrogel+NIR irradiation. Each group contained 5 mice. All mice were acclimatized for 1 week before surgery. For the surgery part, all procedures were performed under aseptic conditions. After standard anesthesia with an intraperitoneal injection of chloral hydrate (0.3 mg/kg body weight), the dorsal region of mice above the tail but below the back was shaved to prepare for surgery. 7 mm diameter full-thickness skin round wounds were created by a needle biopsy. After removing the wound skin, all groups were added with 10 μL of S. aureus suspension (10$^8$ CFU/mL). The control group was not treated. The OSD/CMC and OSD/CMC/Fe/PA3 hydrogel groups were treated with hydrogel directly. For the NIR irradiation group and OSD/CMC/Fe/PA3 hydrogel+NIR irradiation group, wounds were exposed to NIR laser light (808 nm, 1.0 W/cm$^2$) for 10 min. After all operations were completed, the samples were taken and dispersed in 5 mL of PBS by a tissue crusher. Then, these samples containing PBS were diluted and cultured on LB agar plates to check the antibacterial activity.

Example 17: In Vivo Infection Wound Treatment and Wound Healing Promotion Capabilities of OSD/CMC/Fe/PA Hydrogels in Full-Thickness Skin Defect Infected Model According to the reference [X. Zhao, H. Wu, B. Guo, R. Dong, Y. Qiu, P. X. Ma, *Antibacterial anti-oxidant electroactive injectable hydrogel as self-healing wound dressing with hemostasis and adhesiveness for cutaneous wound healing, Biomaterials* 122 (2017) 34-47, incorporated herein by reference in its entirety], the in vivo wound healing promotion capability of OSD/CMC/Fe/PA hydrogel was evaluated by infected full-thickness skin defect model with male mice (Kunming) weighing 30-40 g and aged 5-6 weeks. The 60 mice were randomly divided into the following four groups: (1) Tegaderm™ film (3M Health Care, USA) as a blank group; (2) OSD/CMC hydrogel as a control group; (3) OSD/CMC/Fe/PA3 hydrogel group; and (4) OSD/CMC/Fe/PA3 with NIR photothermal treatment as an experimental group. The 15 mice in each group were randomly divided into the following three sampling points: 3rd, 7th, and 14th days, and each sampling point had five mice (n=5). After grouping, all mice underwent the following operations under aseptic conditions: (1) all mice were anesthetized by intraperitoneal injection of 10% chloral hydrate solution with 3.33 mL/kg; (2) the hair on the back of all mice was removed to facilitate the following operations; (3) a circular wound of full-thickness skin 7 mm in diameter was created in the dorsal region of the mouse above the tail but below the back using a needle biopsy; (4) the MRSA solutions (10 μL, 10$^8$ CFU/mL) were added to the wound sites; (5) in the blank group, the film was covered directly with Tegaderm™ without any treatment. As for the other three groups, 50 μL of the OSD/CMC and OSD/CMC/Fe/PA3 hydrogels were added to the wound sites and covered by Tegaderm™ films; and (6) the full-thickness circular skin wounds with OSD/CMC/Fe/PA3 hydrogel in NIR group were treated with NIR photothermal treatment for 10 min. After surgery on the 3rd, 7th, and 14th days, the wound areas of each group were counted, and the tissue around the wound site was collected for further histomorphological observation and biochemical index analysis.

Example 18: The Evaluations of Wound Healing in the Full-Thickness Skin Defect Model and Full-Thickness Skin Defect Infected Model According to the reference [X. Zhao, H. Wu, B. Guo, R. Dong, Y. Qiu, P. X. Ma, *Antibacterial anti-oxidant electroactive injectable hydrogel as self-healing wound dressing with hemostasis and adhesiveness for cutaneous wound healing, Biomaterials* 122 (2017) 34-47, incorporated herein by reference in its entirety], for visual evaluation of wound healing, after surgery for 3rd, 7th, and 14th days, the wound areas of each group were counted. The following formula calculated the wound contraction ratios: Wound contraction (%)=area ($0^{th}$ day)−area ($n^{th}$ day)/area ($0^{th}$ day)×100%, where n is the date after surgery.

Subsequently, the tissue around the wound site was collected on the 3rd, 7th, and 14th days and fixed with 4% paraformaldehyde for 1 h for further histomorphological observation and biochemical index analysis. Histomorphological observation was used to evaluate the process of wound healing from the epidermal regeneration and inflammation. The wound site tissue, after fixed, was embedded in paraffin, transected into 4 m thick sections, and stained with hematoxylin-eosin (H&E). After that, a microscope (IX53, Olympus, Japan) was employed to photograph and analyze the staining results. As for biochemical index analysis, the TNF-α and VEGF antibody (abeam) was used to stain the wound tissue above with four m thick sections. The nuclei were stained with a DAPI-containing mounting solution. Slides were observed under an inverted fluorescence microscope (IX53, Olympus, Japan). After that, a microscope (IX53, Olympus, Japan) was employed to photograph and analyze the staining results.

Example 19: Statistical Analysis

For statistical analysis, the experimental data in this study were presented as mean±standard deviation and analyzed employing a Student's t-test. When the P value was less than 0.05, the data were considered to have a significant difference.

Results and Discussion

Figures 2A, 2B:
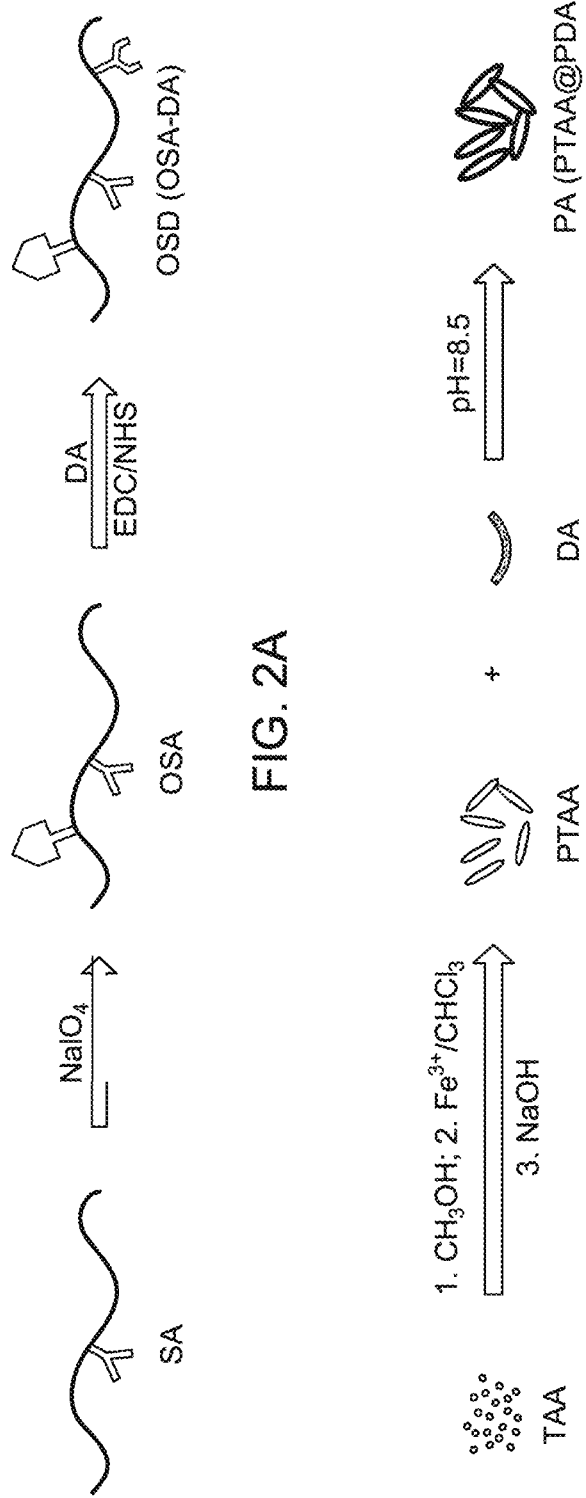
FIG. 2A depicts a reaction scheme for the synthesis of the OSD, according to certain embodiments.
FIG. 2B depicts a reaction scheme for synthesizing the PA, according to certain embodiments.
Figure 2C:
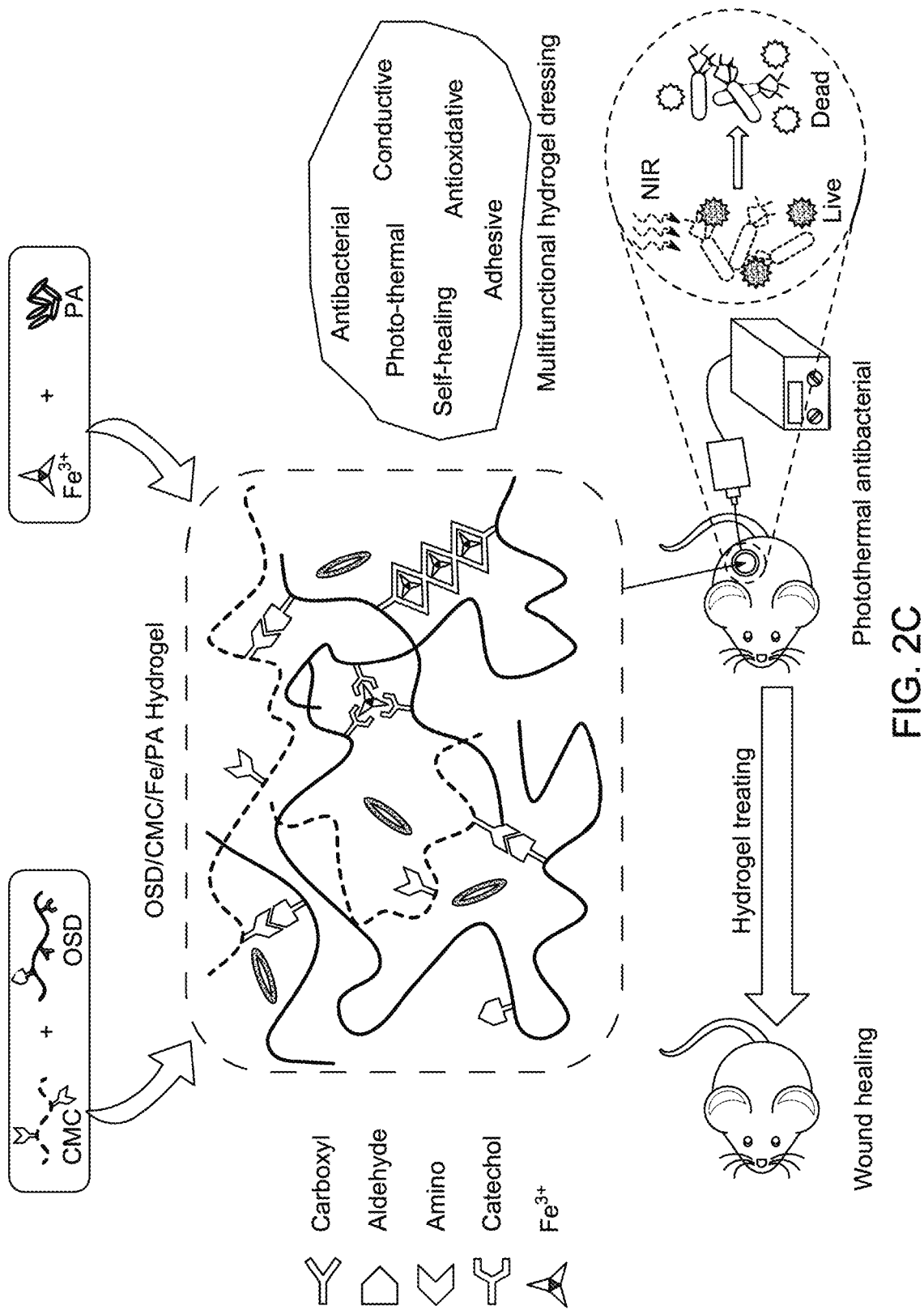
FIG. 2C depicts a reaction scheme for the synthesis of OSD/carboxymethyl chitosan (CMC)/$Fe^{3+}$/PA (OSD/CMC/Fe/PA) hydrogels, according to certain embodiments.

According to the present disclosure, a range of self-healing antibacterial conductive hydrogel dressings with dual dynamic bonds and suitable mechanical properties, conductivity, photothermal properties, antioxidant properties, self-healing properties, and biocompatibility were prepared. Further, the evaluation of their application in treating infected wounds was also demonstrated. A schematic illustration for designing the hydrogel for wound healing is shown in FIGS. 2A-2C. Sodium alginate (SA) was selected as a network molecule because it has good biocompatibility and coordination properties with metals. To give SA one or more aldehyde groups, sodium periodate was used to oxidize sodium alginate to obtain oxidized sodium alginate (OSA), as shown in FIG. 2A. The appearance of two peaks with δ 4.9 and 5.0 in the proton nuclear magnetic resonance ($^1$H NMR) spectrum proved the synthesis of OSA, as shown in FIG. 3. To impart good adhesion and antioxidant to OSA, dopamine (DA) was linked to OSA by 1-(3-dimethylaminopropyl)-3-ethyl-ethylcarbodiimide hydrochloride (EDC)/N-hydroxysuccinyl imine (NHS) chemistry to synthesize dopamine-grafted oxidized sodium alginate (OSD), as shown in FIG. 2A. The appearance of the benzene ring peak (δ=6.9) on the $^1$H NMR spectrum of OSD proves the successful grafting of dopamine, as shown in FIG. 3.

PTAA, which has conductive properties, was coated with polydopamine (PDA) to improve water solubility and photothermal properties, as shown in FIG. 2B. Further, PDA may also increase tissue adhesion.

Figures 4A, 4B:
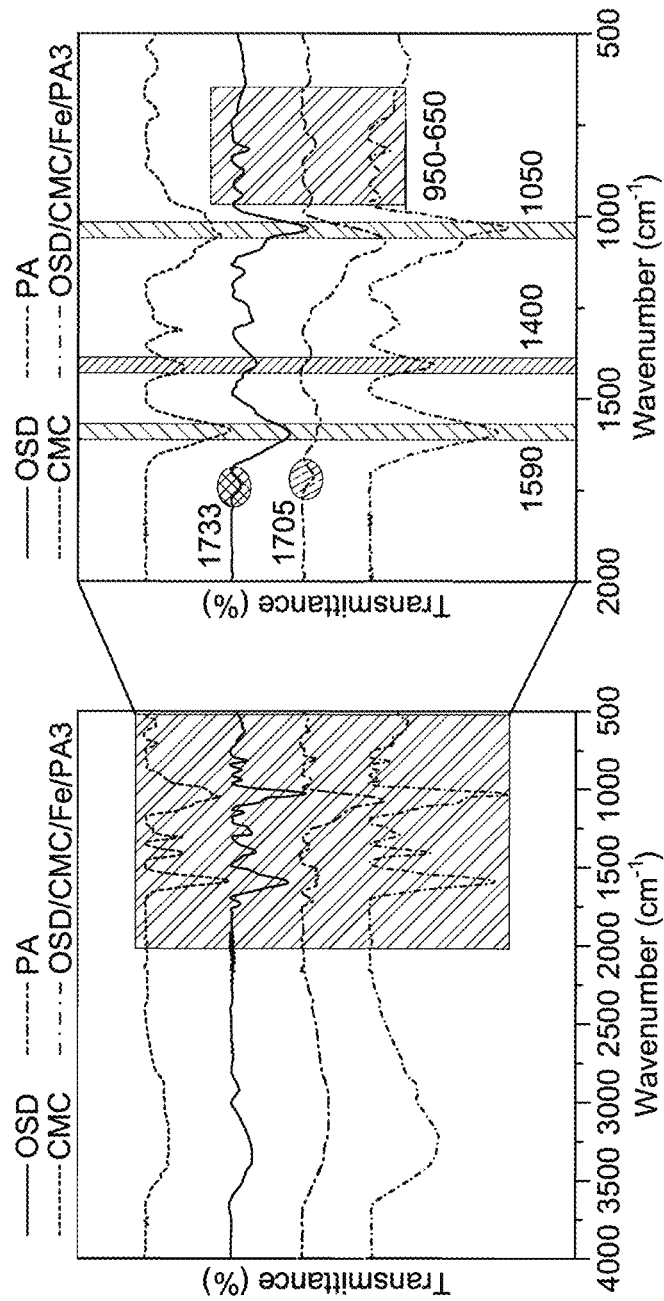
FIG. 4A depicts Fourier transform infrared spectroscopy (FTIR) spectra for OSD, CMC, PA, and dried OSD/CMC/Fe/PA3 hydrogel, according to certain embodiments.
FIG. 4B is a graph depicting FTIR spectroscopy results for OSD, CMC, PA and dried OSD/CMC/Fe/PA3 hydrogel, according to certain embodiments.

Carboxymethyl chitosan (CMC) was chosen as another component to introduce Schiff base bonds in the hydrogel network (FIG. 2C). As a chemically modified chitosan, CMC has good water solubility and biocompatibility, and contains carboxyl and amino groups. CMC may form Schiff base bonds with the OSD and coordinate with metal ions. Furthermore, to further strengthen the network of the hydrogel, $Fe^{3+}$ ions were introduced to coordinate with carboxyl groups in CMC and catechol groups in dopamine, as shown in FIG. 2C. In the Fourier Transform Infrared (FTIR) spectra (FIGS. 4A-4B) the successful formation of OSD is demonstrated by an aldehyde peak at 1733 $cm^{-1}$, a benzene ring peak at 950 $cm^{-1}$ to 650 $cm^{-1}$ and the C—N bond peak at 1400 $cm^{-1}$. The carboxylic acid peak at 1705 $cm^{-1}$, the thiophene ring peak at 1200 $cm^{-1}$ to 1050 $cm^{-1}$ and the benzene ring peak at 950 $cm^{-1}$ to 650 $cm^{-1}$ of PA also proved the preparation of PA. The FTIR spectra of the OSD/CMC/Fe/PA hydrogels showed the superposition of the carboxylate, Schiff base, and amide peaks at 1590 $cm^{-1}$ and the hydroxyl peak in the sugar ring at 1050 $cm^{-1}$. Additionally, a series of multifunctional antibacterial OSD/CMC/Fe/PA hydrogel dressings were constructed to repair infected full-thickness skin wound models in mice, as depicted in FIG. 2C. The different hydrogels were named OSD/CMC, OSD/CMC/Fe, OSD/CMC/Fe/PA1 (1 wt. % PA), OSD/CMC/Fe/PA3 (3 wt. % PA), and OSD/CMC/Fe/PA5 (5 wt. % PA) according to the presence or absence of $Fe^{3+}$ and the amount of PA added.

Figure 5A:
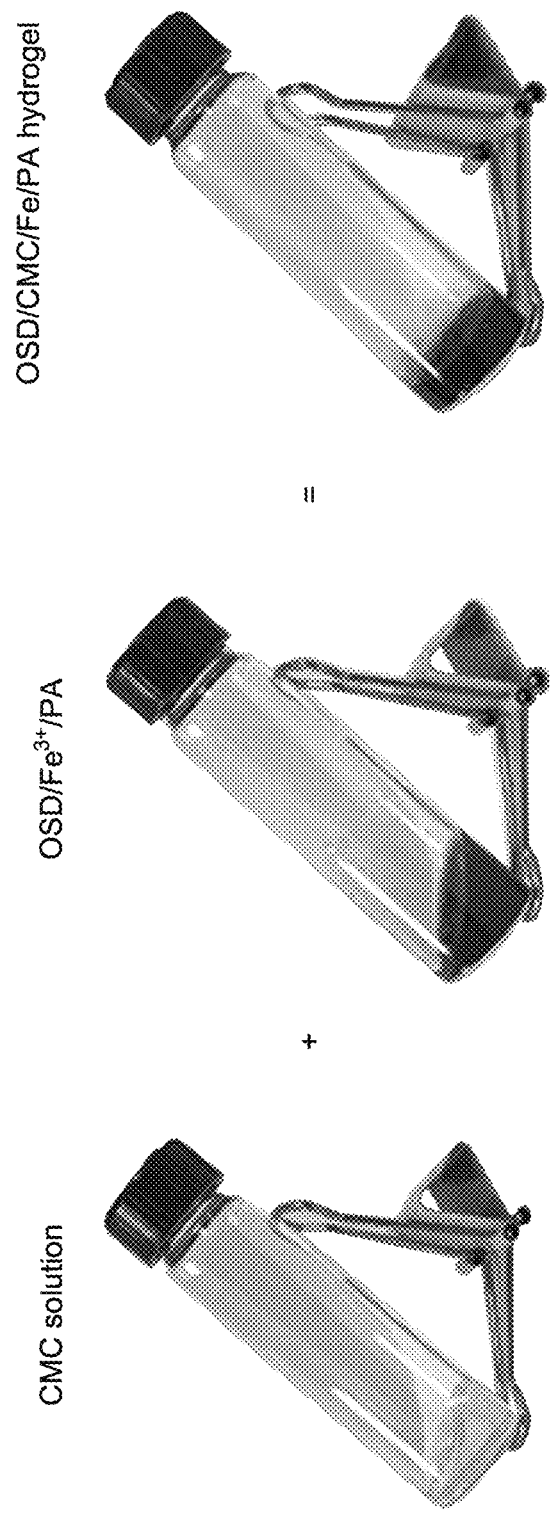
FIG. 5A depicts optical images of hydrogel formation, according to certain embodiments.
Figure 5B:
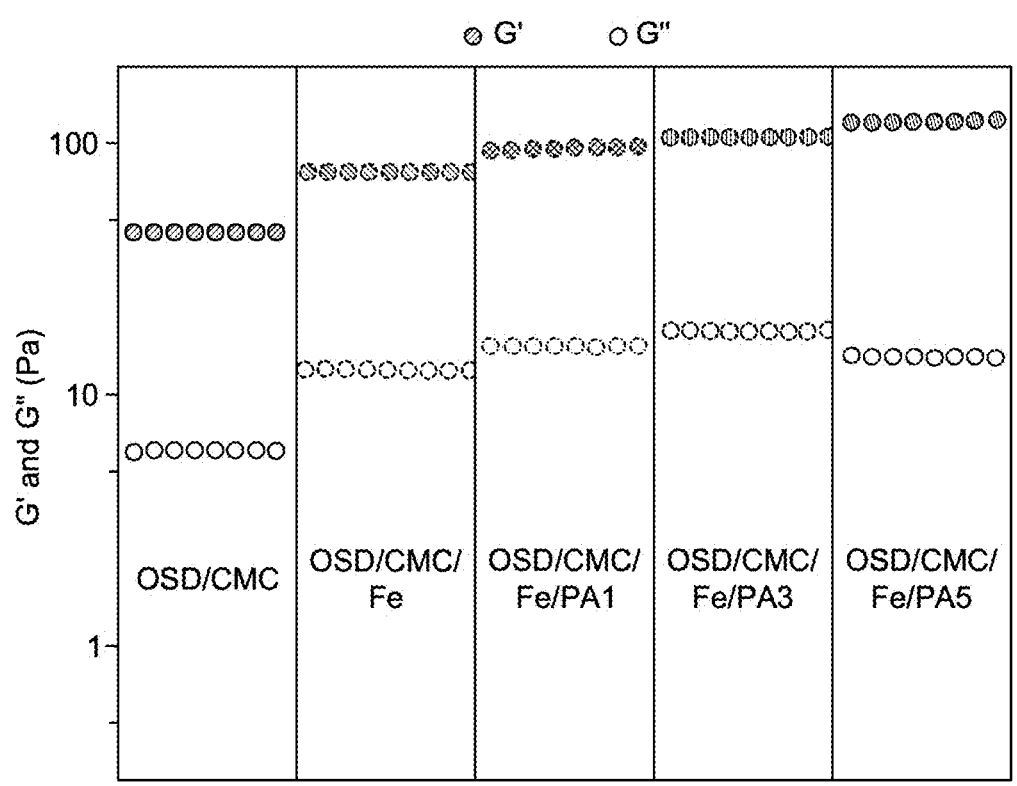
FIG. 5B depicts the modulus of hydrogels with a scanning time of 300 seconds for each group, according to certain embodiments.
Figure 5C:
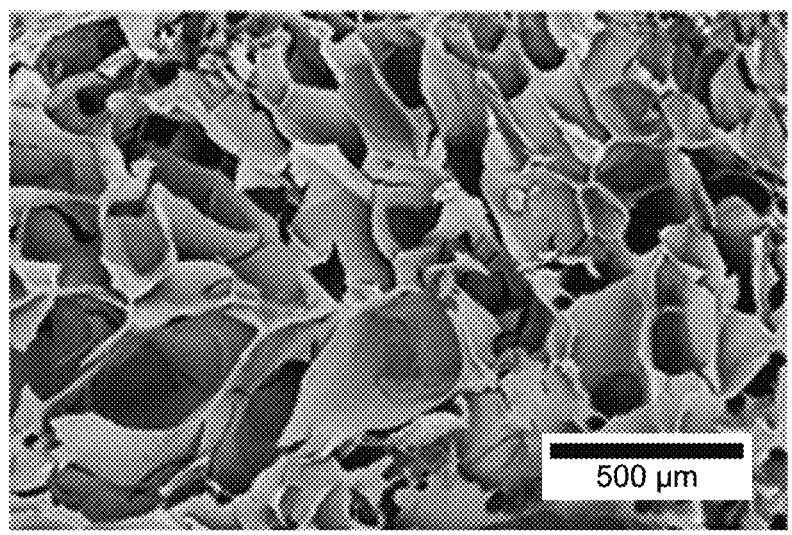
Figure 1:
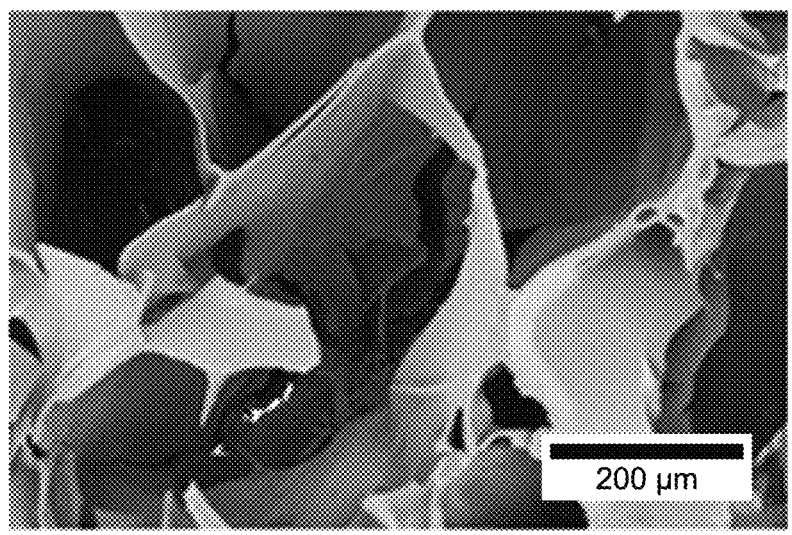
Figure 5C:
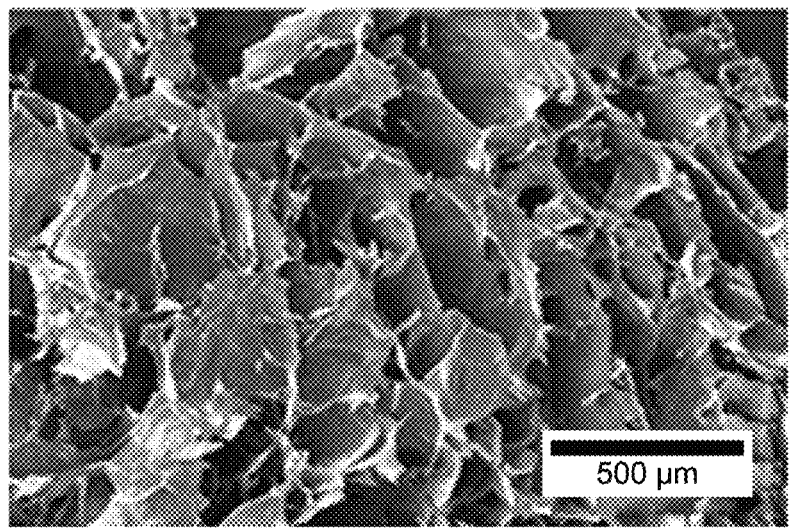
Figure 2:
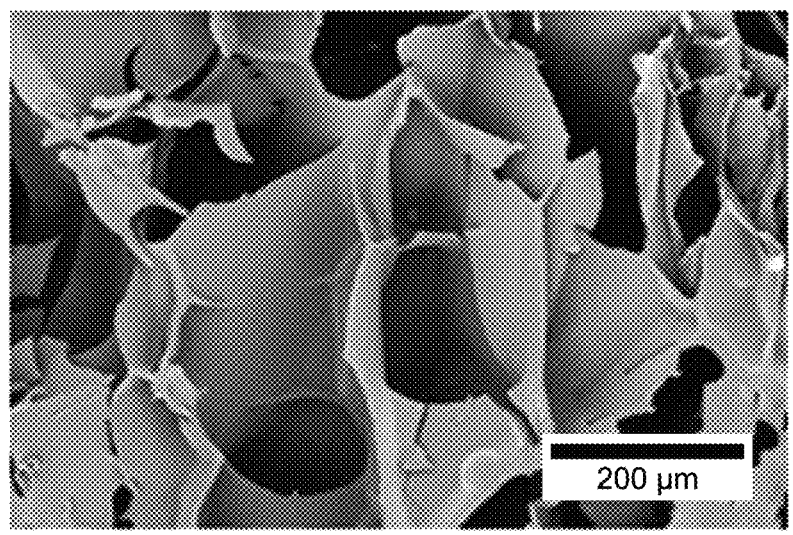
Figure 5C:
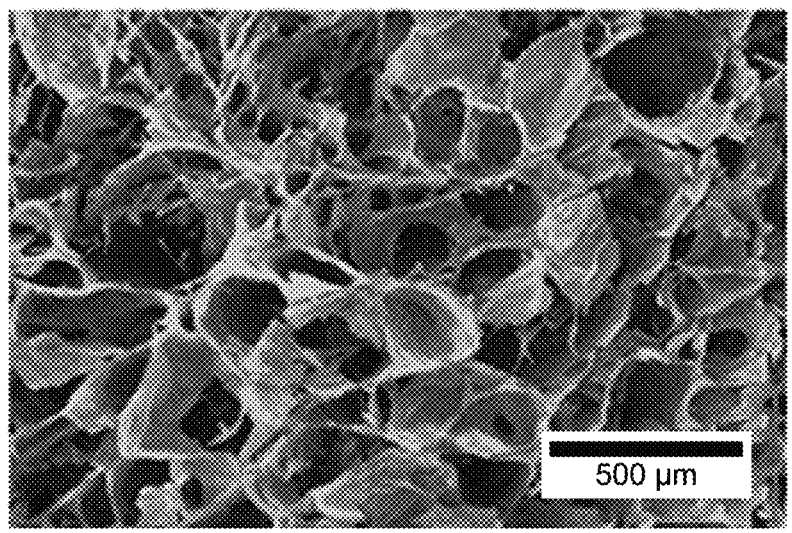
Figure 3:
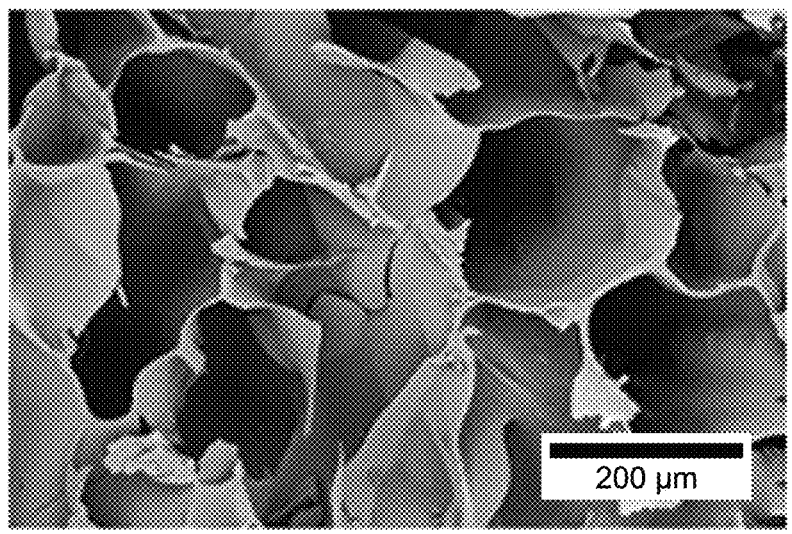
Figure 5C:
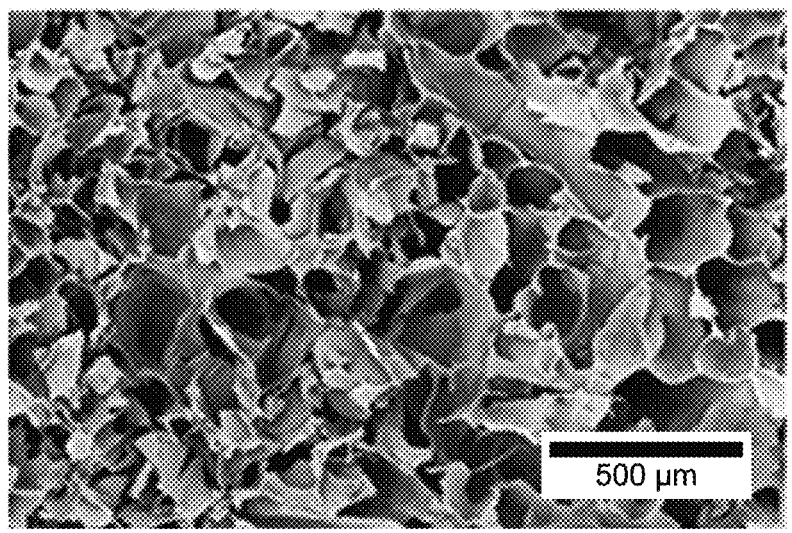
Figure 4:
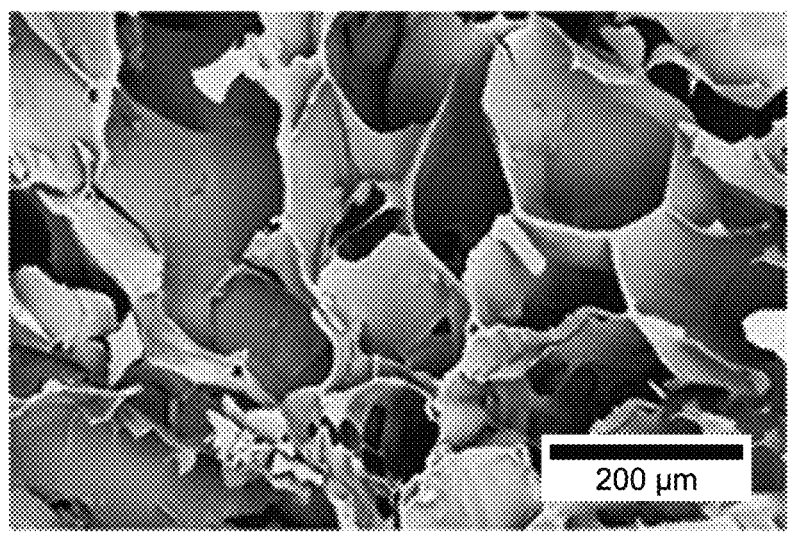
Figure 5C:
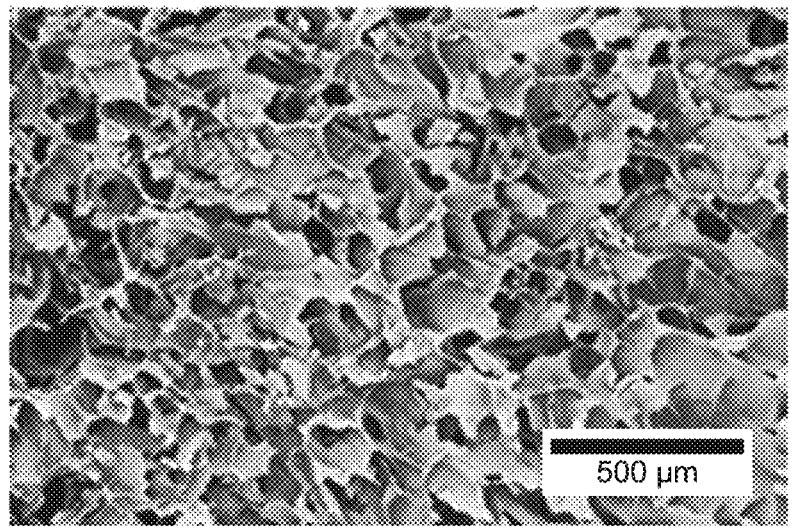
Figure 5:
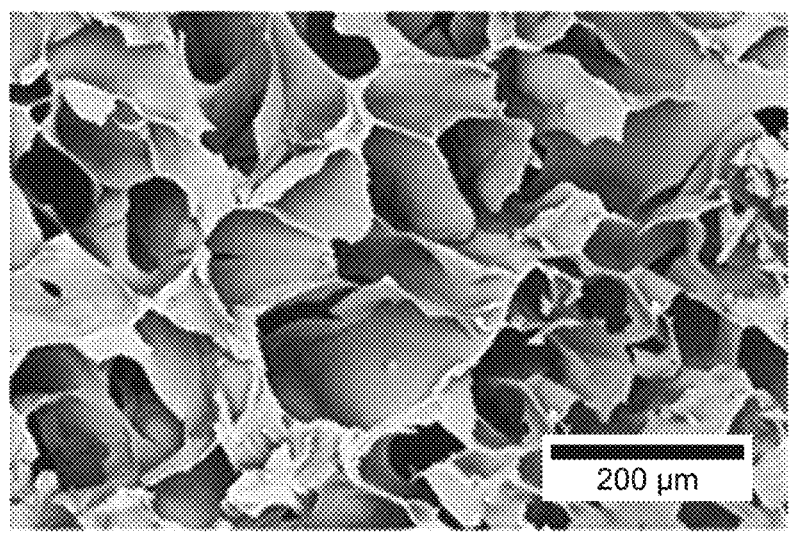

FIG. 5A shows optical images for the preparation of the hydrogel. The OSD/CMC/Fe/PA hydrogel can be formed by mixing the CMC solution with the OSD/$Fe^{3+}$/PA mixture. The storage modulus (G') and loss modulus (G") of a series of hydrogels were recorded as a function of time to examine the effect of different PA contents on the modulus of OSD/CMC/Fe/PA hydrogels, as shown in FIG. 5B. The G' of the OSD/CMC/Fe/PA5 hydrogel with 5 wt. % PA (120.9 Pa) was higher than the values obtained for hydrogel with PA 3 wt. % (104.9 Pa), 1 wt. % (94.8 Pa) and 0 wt. % (77.4 Pa) and OSD/CMC hydrogel (44.2 Pa). This is because the addition of $Fe^{3+}$ and the increase of PA content led to the increase of the crosslinking density of the hydrogel, which in turn led to the gradual increase of the G' of the hydrogel. The morphology of these OSD/CMC/Fe/PA hydrogels was observed by scanning electron microscopy (SEM), as shown in FIGS. 5C-1, 5C-2, 5C-3, 5C-4 and 5C-5. The pore size of the hydrogel is negatively correlated with the amount of PA added; that is, with the increase of the amount of PA, the pore size of the hydrogel gradually decreases. It is believed that the hydrogel network strengthens step by step with PA added, thereby forming a smaller pore size.

Figure 5D:
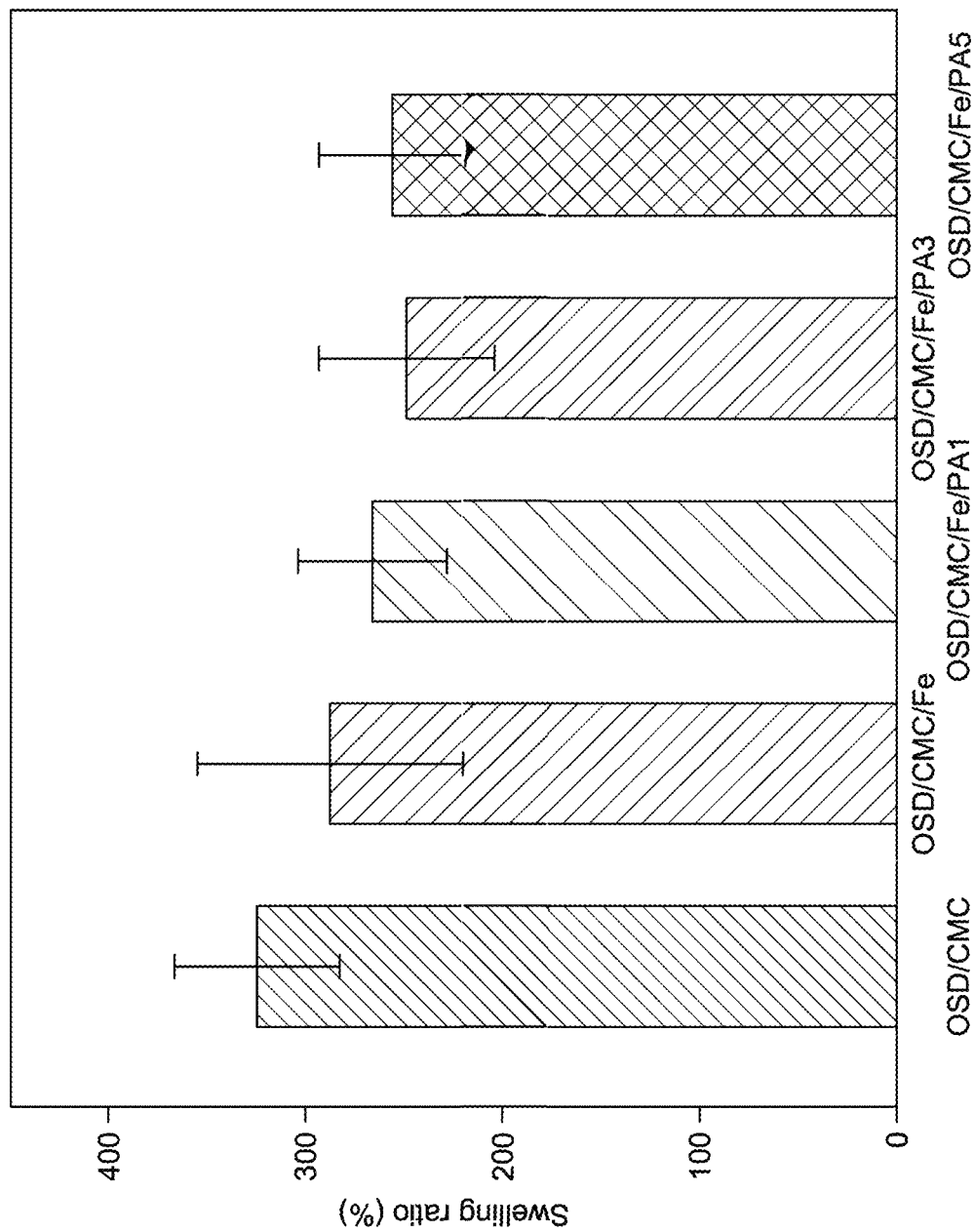
FIG. 5D depicts the swelling ratio of different hydrogels, according to certain embodiments.

The swelling ratio is an important parameter for hydrogels. The hydrogel effectively reduces infection by absorbing wound exudate, resulting in faster wound healing. FIG. 5D shows the swelling ratio of these hydrogels. Among them, OSD/CMC hydrogel has the highest swelling ratio, reaching about 320%. The OSD/CMC/Fe hydrogel network was further enhanced by adding $Fe^{3+}$ to form metal coordination bonds, and the swelling ratio decreased to 288%. Furthermore, the networks of OSD/CMC/Fe/PA1 hydrogel, OSD/CMC/Fe/PA3 hydrogel, and OSD/CMC/Fe/PA5 hydrogel were gradually enhanced with increasing the amount of PA, and the swelling ratio decreased from 266% to 249% and 240%, respectively. The experimental results showed that the swelling ratio of the hydrogel gradually reduced with the addition of $Fe^{3+}$ and PA, which proved the enhancement of the hydrogel network to some extent.

Figure 5E:
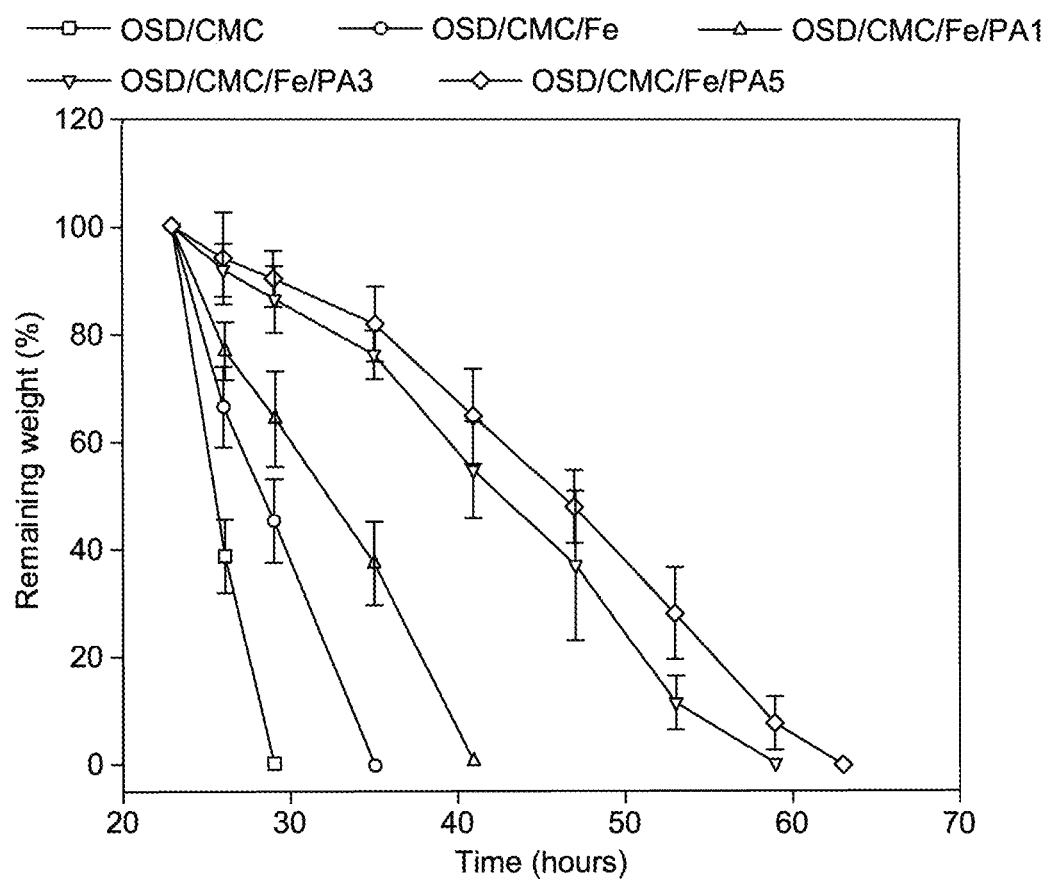
FIG. 5E is a graph depicting the effect of time on the degradation of hydrogels in phosphate-buffered saline (PBS) at 37° C. and a pH of 7.4, according to certain embodiments.
Figure 5F:
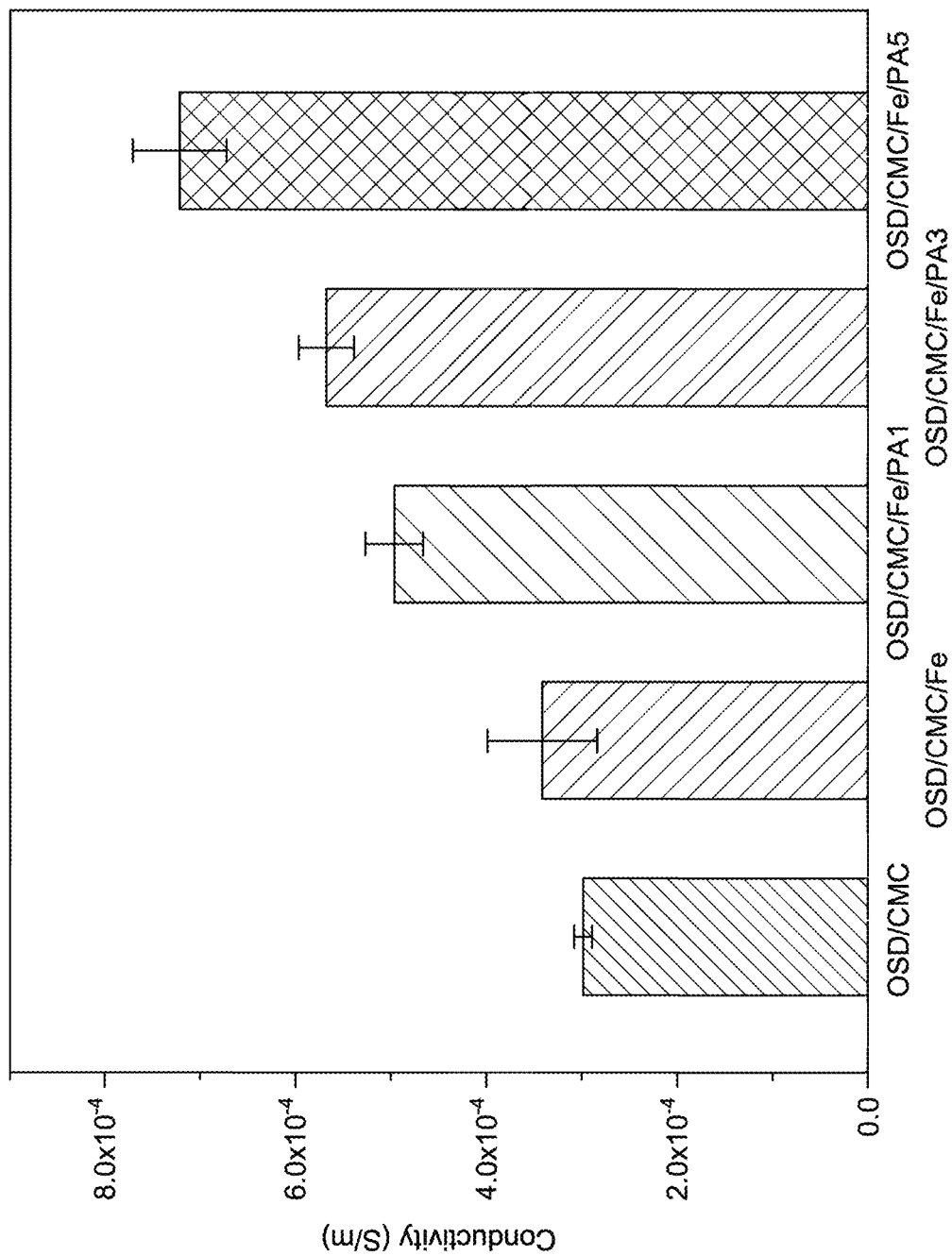
FIG. 5F depicts the conductivity of different hydrogels, according to certain embodiments.

An appropriate degradation rate is important for biomaterials. The results, as presented in FIG. 5E, show that the OSD/CMC hydrogel was degraded entirely in less than 30 h due to the single Schiff base network. However, the OSD/CMC/Fe hydrogel network was strengthened after adding $Fe^{3+}$, which led to complete degradation within 35 h. Furthermore, with the addition of PA, the degradation time of OSD/CMC/Fe/PA1 hydrogel, OSD/CMC/Fe/PA3 hydrogel, and OSD/CMC/Fe/PA5 hydrogel increased from 41 h to 59 h and 63 h, respectively. It may be noted that the amount of $Fe^{3+}$ and PA nanoparticles increased the strength of the cross-linked network of the hydrogel. PTAA has good conductivity, biocompatibility, and chemical stability. Hence, it was selected as the conductive component to endow these OSD/CMC/Fe/PA hydrogels with conductive properties. Conductive biomaterials have the potential to accelerate wound healing. The conductivity of these hydrogels is shown in FIG. 5F. OSD/CMC hydrogel has the lowest conductivity ($3.0 \times 10^{-4}$ S $m^{-1}$). However, OSD/CMC/Fe hydrogel has an increased conductivity ($3.43 \times 10^{-4}$ S $m^{-1}$) due to the addition of $Fe^3$. Benefit from the addition of conductive nanoparticles PA, the conductivity of OSD/CMC/Fe/PA1 hydrogel, OSD/CMC/Fe/PA3 hydrogel, and OSD/CMC/Fe/PA5 hydrogel increased from $5.0 \times 10^{-4}$ S $m^{-1}$ to $5.7 \times 10^{-4}$ S $m^{-1}$ and $7.2 \times 10^{-4}$ S $m^{-1}$, respectively. Dressings with conductive properties may enhance endogenous electrical currents in the skin, causing neutrophils, macrophages, and keratinocytes to migrate to the wound site, accelerating wound healing. Therefore, these conductive wound dressings show similar conductivity to skin and may be favorable for wound healing.

Figure 6A:
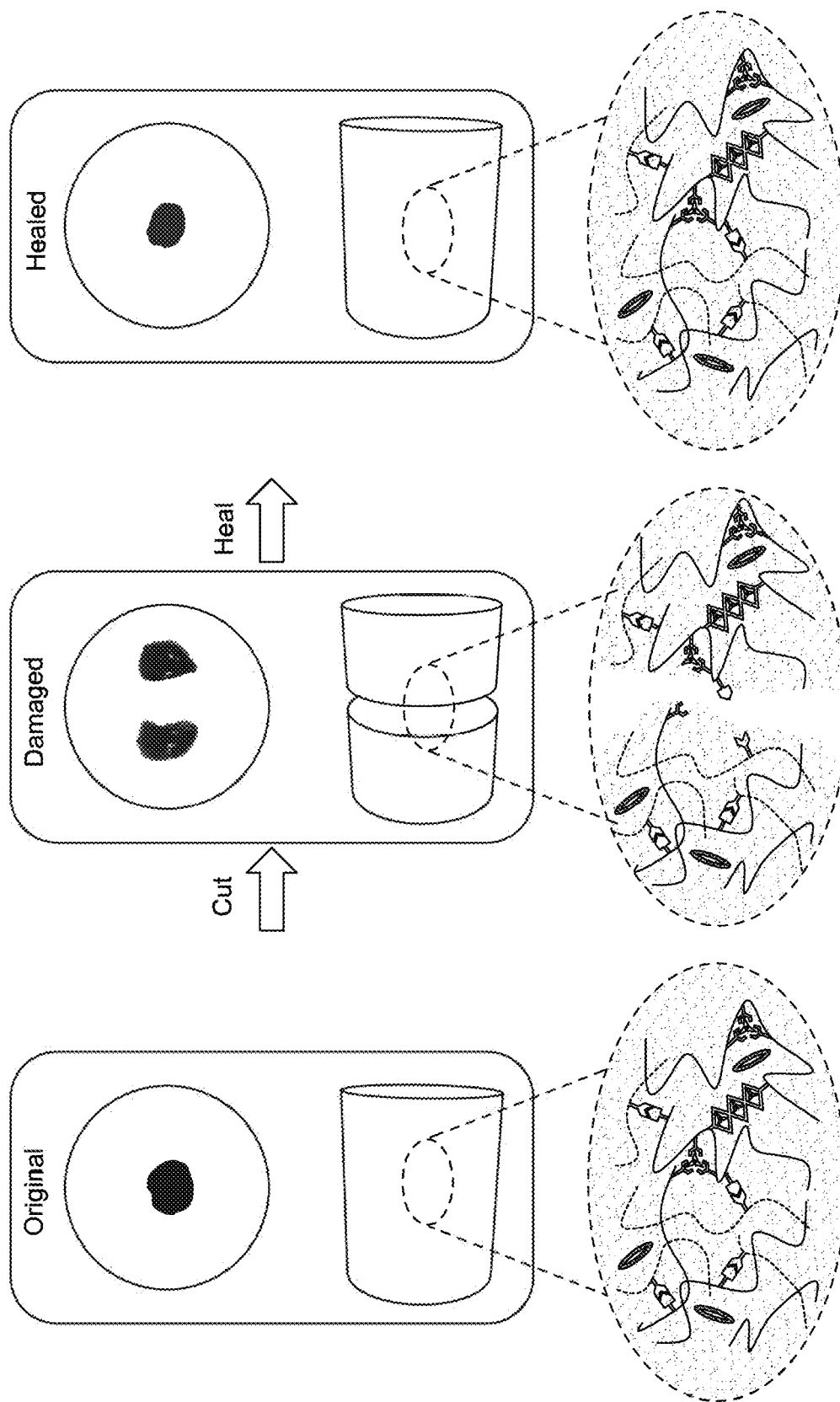
FIG. 6A depicts the self-healing demonstration and possible mechanisms of microscopic healing in hydrogels at a scale bar of 1 cm, according to certain embodiments.
Figure 6B:
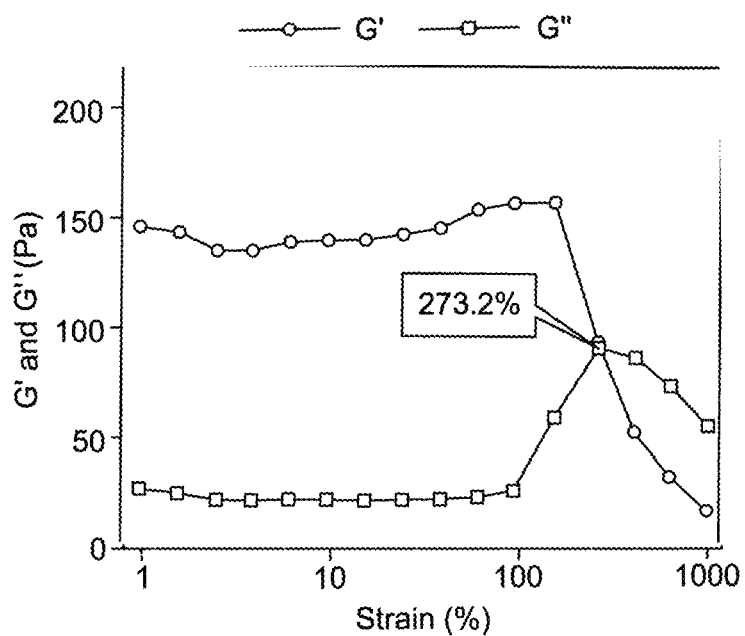
FIG. 6B depicts fracture point testing results of the hydrogel, according to certain embodiments.
Figure 6C:
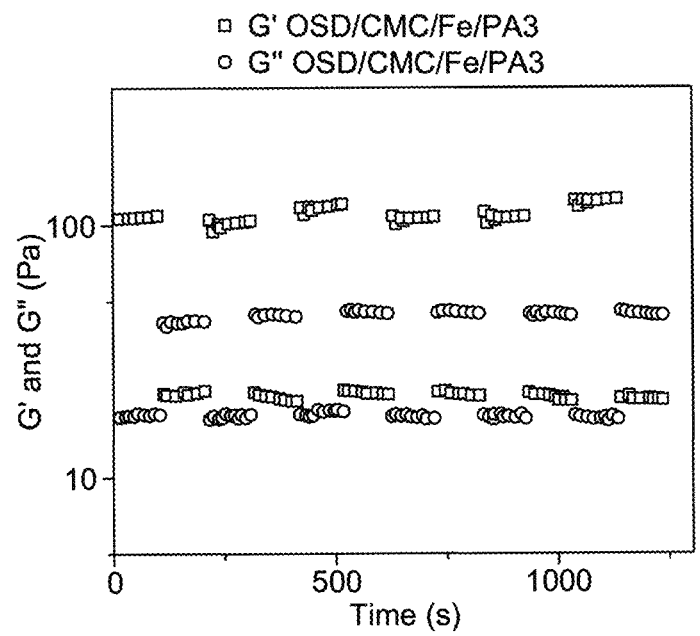
FIG. 6C depicts self-healing test results of the hydrogel, according to certain embodiments.

Dressings covering the wound surface can easily be damaged by skin movement, thus failing to heal the wound or even causing wound infection. The self-healing hydrogel wound dressing repairs the broken part of the dressing by self-healing behavior so that the dressing can treat and protect the wound for an extended period. OSD/CMC/Fe/PA3 hydrogel was chosen as a representation to test the self-healing properties of the hydrogel. FIG. 6A shows a macro-level self-healing performance of the OSD/CMC/Fe/PA3 hydrogel. The OSD/CMC/Fe/PA3 hydrogel was sliced in half and carried out in close contact. After 10 min at 25° C., the two hydrogels healed into a complete hydrogel. The dual dynamic network hydrogels with ligand and Schiff base bonds of the hydrogel are the source of good automatic repair ability. OSD/CMC/Fe/PA3 hydrogels were tested at the rheological level to examine their self-healing properties further. The results in FIG. 6B shows that G' of the hydrogel is equal to G" when the strain reaches 273.2%, indicating that at this strain, the hydrogel is in between solid and liquid state. The hydrogel is destroyed after the critical strain (strain >273.2%). The hydrogel's self-recovering ability was subsequently performed using successive step-strain tests, as shown in FIG. 6C. At first, at 300% strain, G' was markedly reduced from 108 Pa to 21 Pa, and the hydrogel network was proven to collapse. At first, a small strain of 1%, G', recovered to 101 Pa, suggesting most of the cross-linked network of the hydrogel had been recovered. After six high and low strain cycles were tested, the healed hydrogels showed similar G' and G" values as the first cycle, confirming the great self-healing properties of the OSD/CMC/Fe/PA3 hydrogels.

Figure 7A:
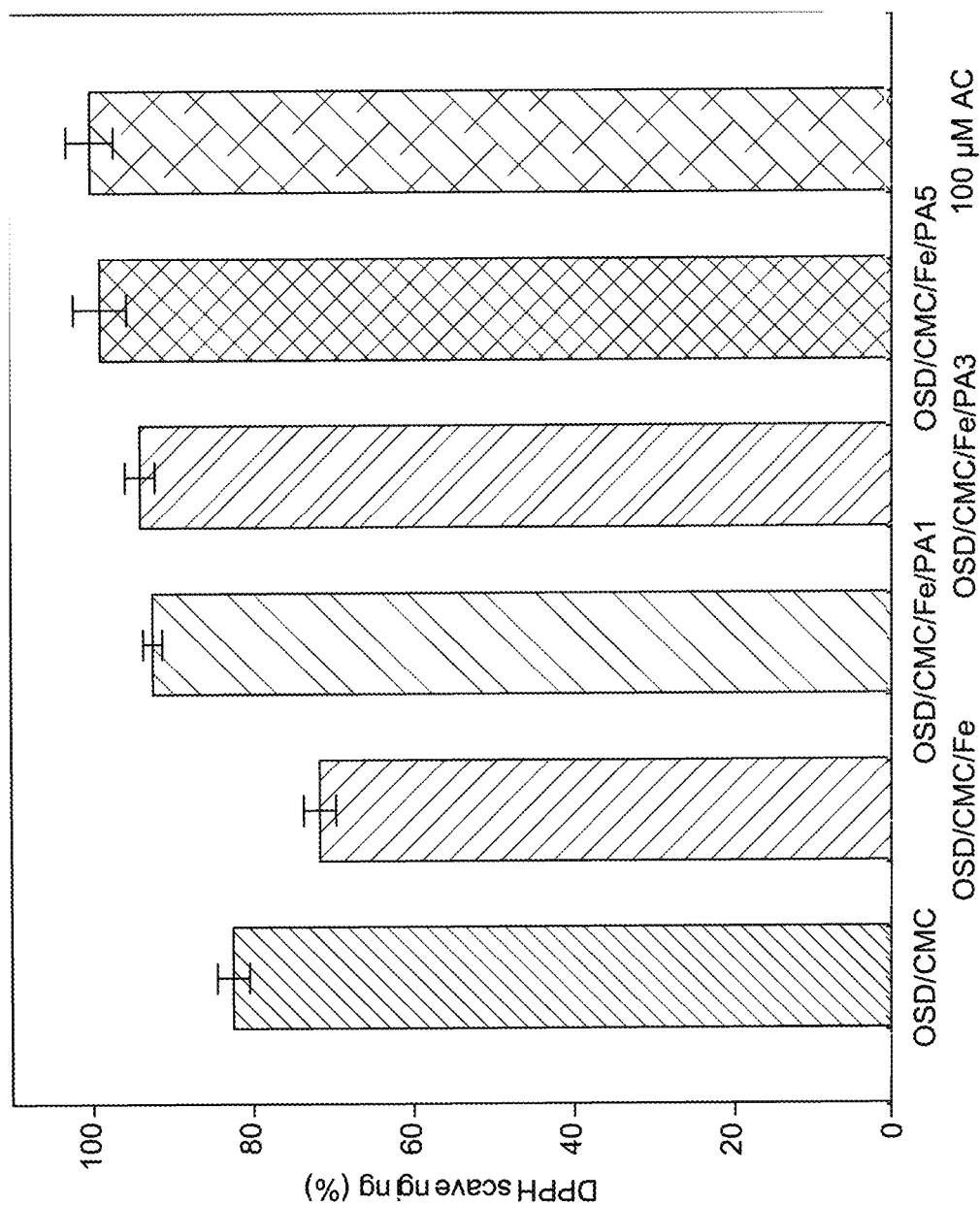
FIG. 7A depicts 2,2-diphenyl-1-picrylhydrazyl (DPPH) clearance ratios of different hydrogels, according to certain embodiments.

A sustained inflammatory response occurs at the wound site in a wound infection, generating a plurality of free radicals. This leads to oxidative stress, further allowing for cellular enzyme inactivation, lipid peroxidation, and DNA damage at the wound site. In general, adding antioxidant ingredients to wound dressings can significantly reduce the production of free radicals at the wound site to accelerate wound closure. 1,1-diphenyl-2-trinitrophenylhydrazine (DPPH) is a stable free radical. According to the present disclosure, the ability of a series of hydrogels to eliminate DPPH was tested, and vitamin C (VC), which has excellent antioxidant properties, was used as a positive control to evaluate its antioxidant properties. The results in FIG. 7A show that these hydrogels have good antioxidant properties because of dopamine. However, the antioxidant properties of OSD/CMC/Fe hydrogels are weakened due to adding $Fe^{3+}$. Meanwhile, with the addition of PA nanoparticles, the antioxidant capacity of the hydrogels was further enhanced by the polydopamine contained in the nanoparticles. The DPPH clearance ratio was above 90% for all three hydrogel groups, and the clearance increased with the increase of PA addition. The activity of the hydrogels to eliminate —O— was further explored by nitro blue tetrazolium (NBT).

Figure 7B:
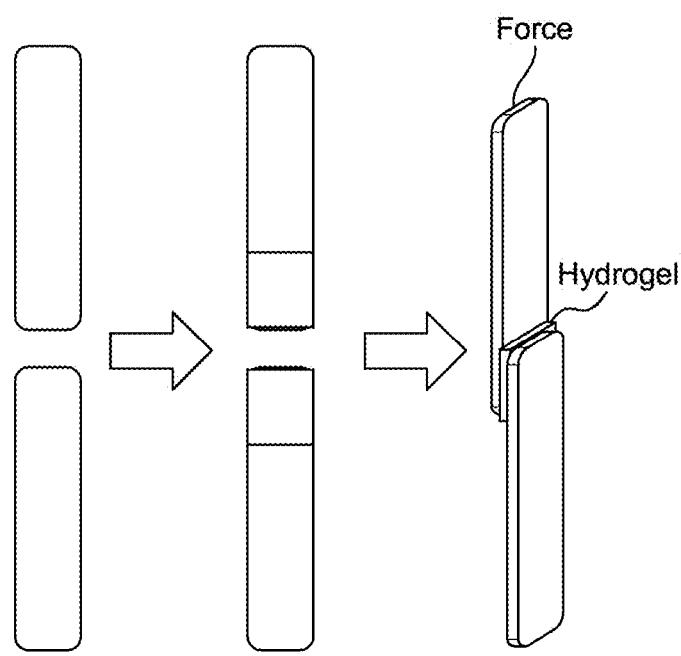
FIG. 7B is a schematic diagram of pigskin adhesion experiment of hydrogels, according to certain embodiments.
Figure 7C:
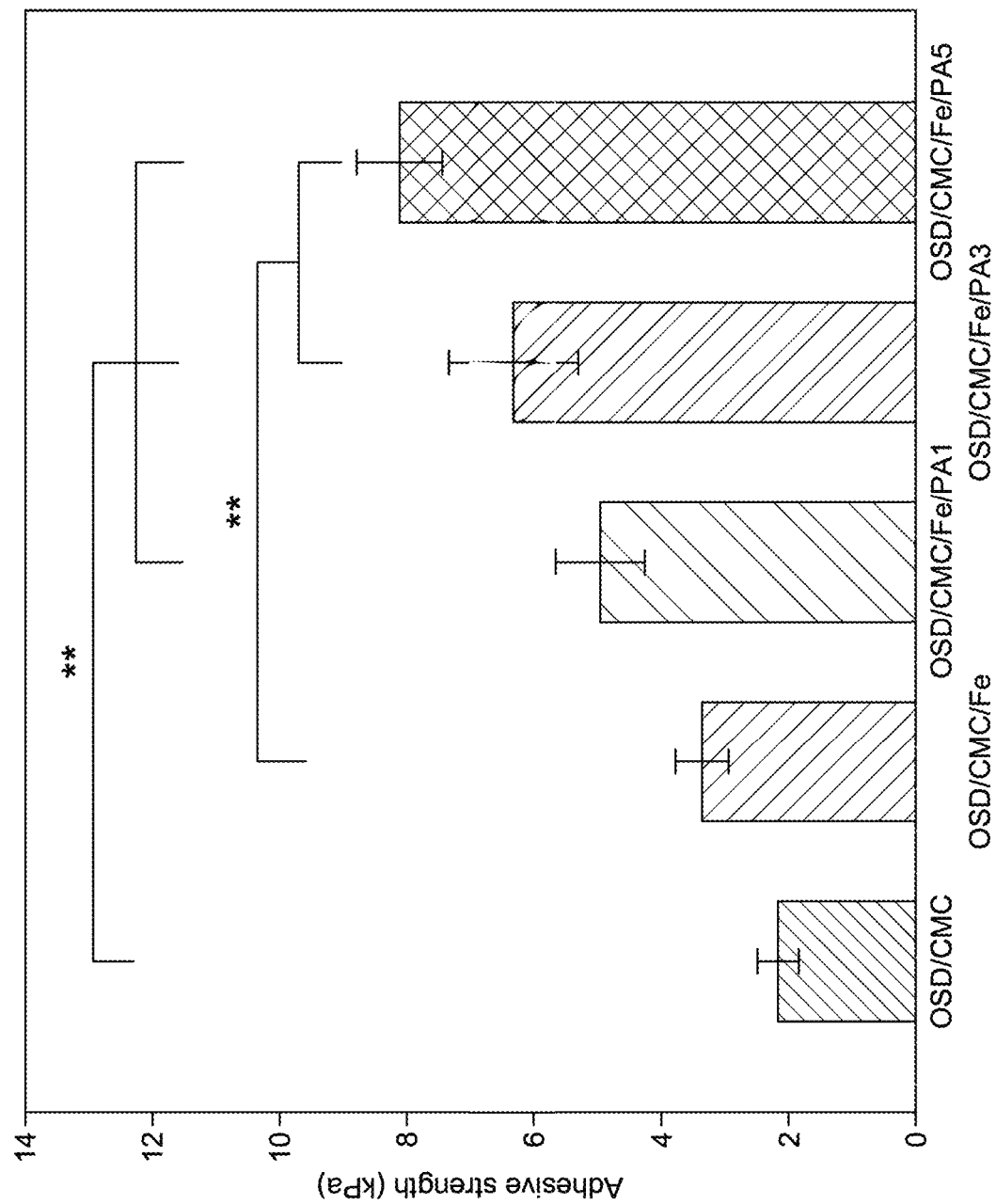
FIG. 7C depicts adhesion strength of pigskin with the hydrogel, according to certain embodiments.
Figure 8:
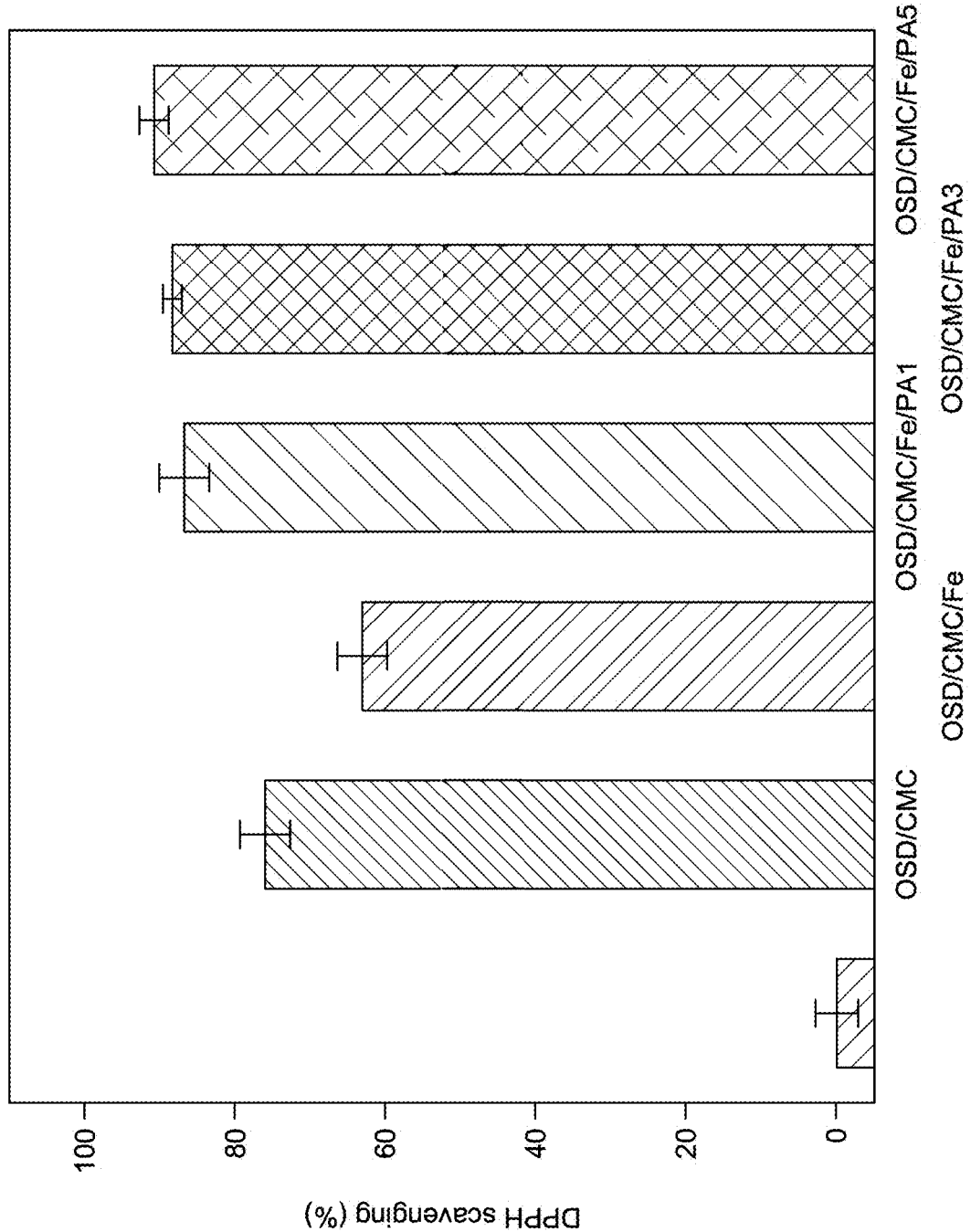
FIG. 8 is a graph depicting the $—O_2^-$ scavenging ratio of the hydrogels, according to certain embodiments.

As shown in FIG. 8, the hydrogel group with PA had the highest activity of eliminating —O—. Specifically, the —O— scavenging ratio of OSD/CMC/Fe/PA1, OSD/CMC/Fe/PA3, and OSD/CMC/Fe/PA5 groups was 86.7%, 88.3%, and 90.7%, respectively, while the —O— clearance ratio of OSD/CMC group was 75.9%, and the —O— scavenging ratio of OSD/CMC/Fe group was the lowest, 63.2%. This showed the same trend as the DPPH scavenging test. Further, a wound dressing needs appropriate adhesion to adhere tightly to the wound. Since the hydrogel contains a large amount of dopamine, dopamine is an effective component that provides adhesion properties in the mussel adhesion protein, and with the abundant hydrogen bonding in the hydrogel; the hydrogel theoretically has sufficient adhesion ability. According to the present disclosure, pig skin lap shear tests were carried out to test the adhesive properties of the materials, and the results are shown in FIGS. 7B-7C. All hydrogels have high adhesive strength, and their adhesion properties positively correlate with the amount of PA. Among them, OSD/CMC/Fe/PA3 hydrogels and OSD/CMC/Fe/PA5 hydrogels exhibited better adhesion strength than commercial dressings (~5 kPa), indicating good adhesion properties of the hydrogels. Possible sources of hydrogel adhesion are the Michael reaction of the aldehyde and quinone groups on the OSD and PA with groups such as amino groups of the skin, as well as electrostatic interactions, π-π interactions, and hydrogen bonding of hydrogels to the skin.

Bleeding is common after a skin injury, especially with a full-thickness defect. Haemostasis is the primary operation in the management of wounds, and rapid haemostasis plays an important role in avoiding massive blood loss. OSD/CMC/Fe/PA hydrogel has several procoagulant components; OSD with catechol of PA, amino of CMC, and iron ions may promote blood coagulation. To explore the haemostasis of hydrogels, the coagulation properties of OSD/CMC/Fe/PA hydrogels were evaluated by dynamic whole blood coagulation assay. Calcified whole blood of rats was used as a control group, and a commercially available hemostatic agent such as a gelatine sponge was used as a positive control. FIG. 7E-FIG. 7F illustrate a series of hydrogels with better procoagulant capacity than gelatine sponges. The catechol structure in OSD/CMC/Fe/PA1 and OSD/CMC/Fe/PA3 hydrogels further promotes blood coagulation with a minimum BCI of about 40% due to the introduction of PA. Compared with OSD/CMC/Fe/PA3 hydrogel, the BCI value of OSD/CMC/Fe/PA5 did not change much because the blood absorption capacity was reduced. The above results demonstrate that the newly developed OSD/CMC/Fe/PA3 hydrogel has good coagulation properties. Based on the procoagulant properties provided by polydopamine and the good tissue adhesion of OSD/CMC/Fe/PA hydrogels, it can be used as a haemostatic agent.

Figure 7D:
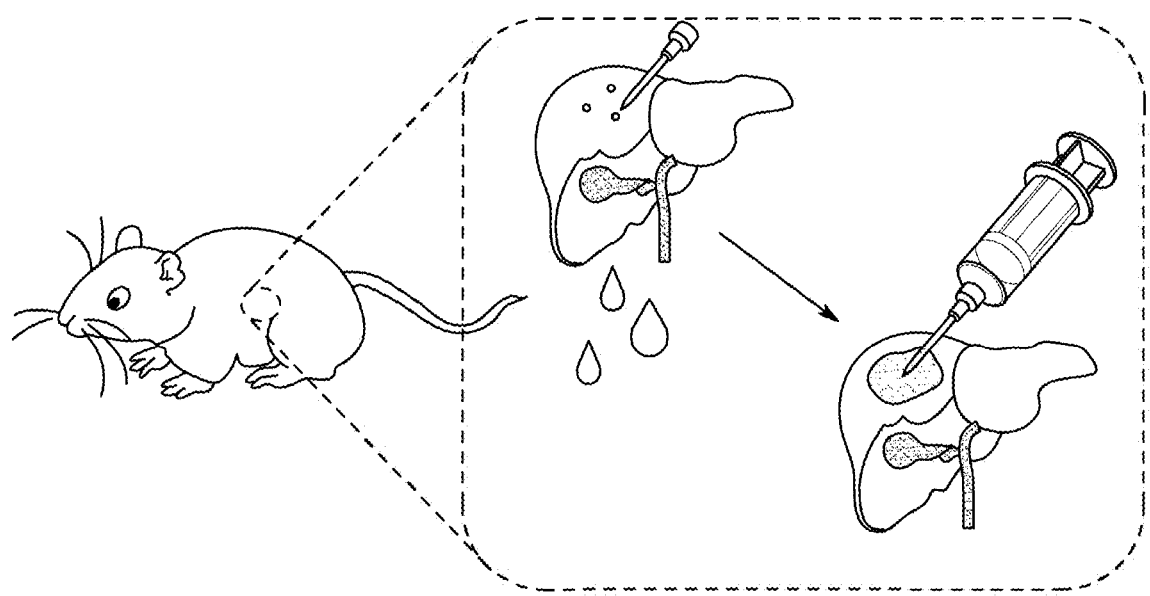
FIG. 7D is a schematic diagram of rat liver hemorrhage model, according to certain embodiments.
Figure 7E:
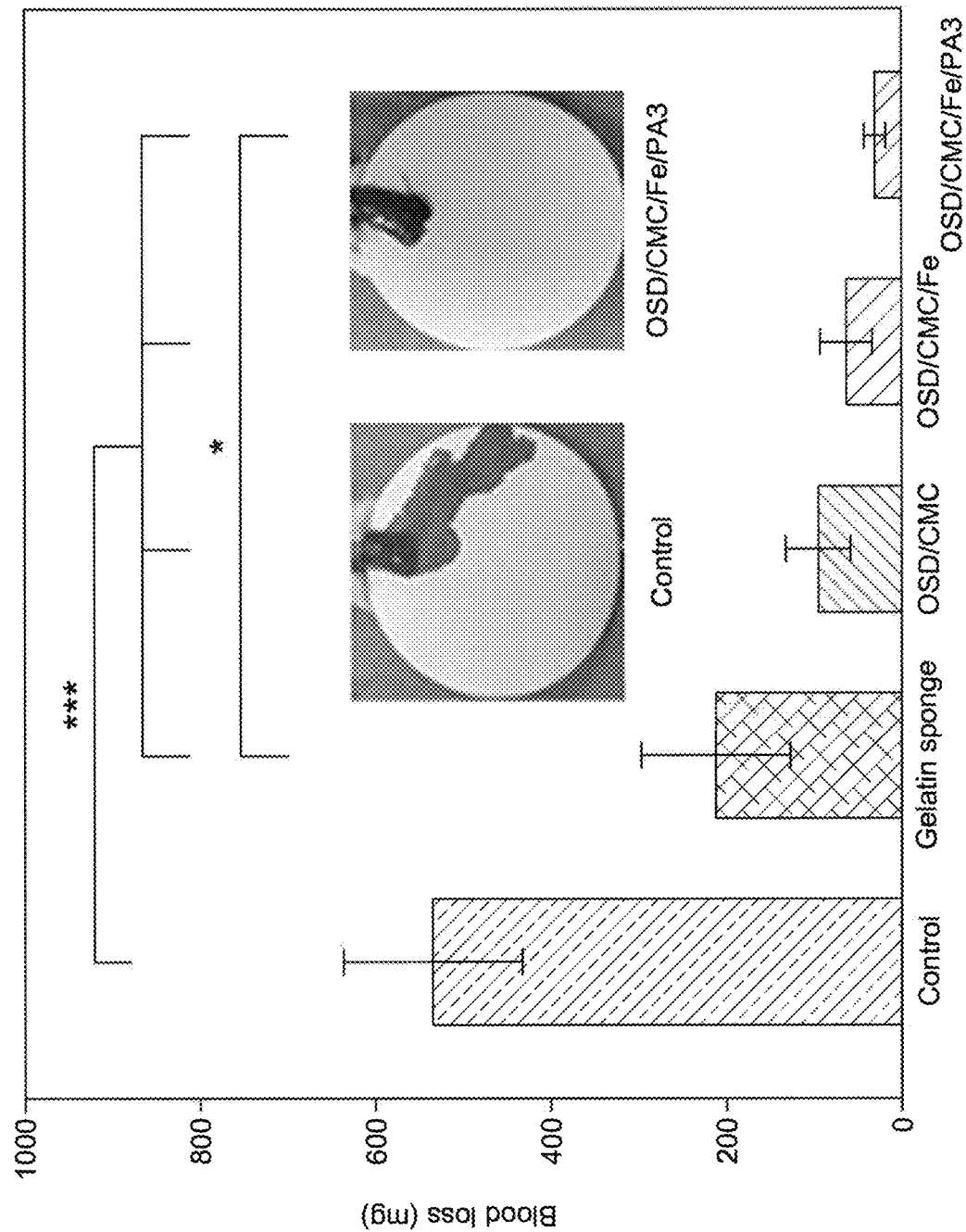
FIG. 7E depicts the haemostatic properties of gelatine sponges, OSD/CMC, OSD/CMC/Fe, and OSD/CMC/Fe/PA3, according to certain embodiments.
Figure 7F:
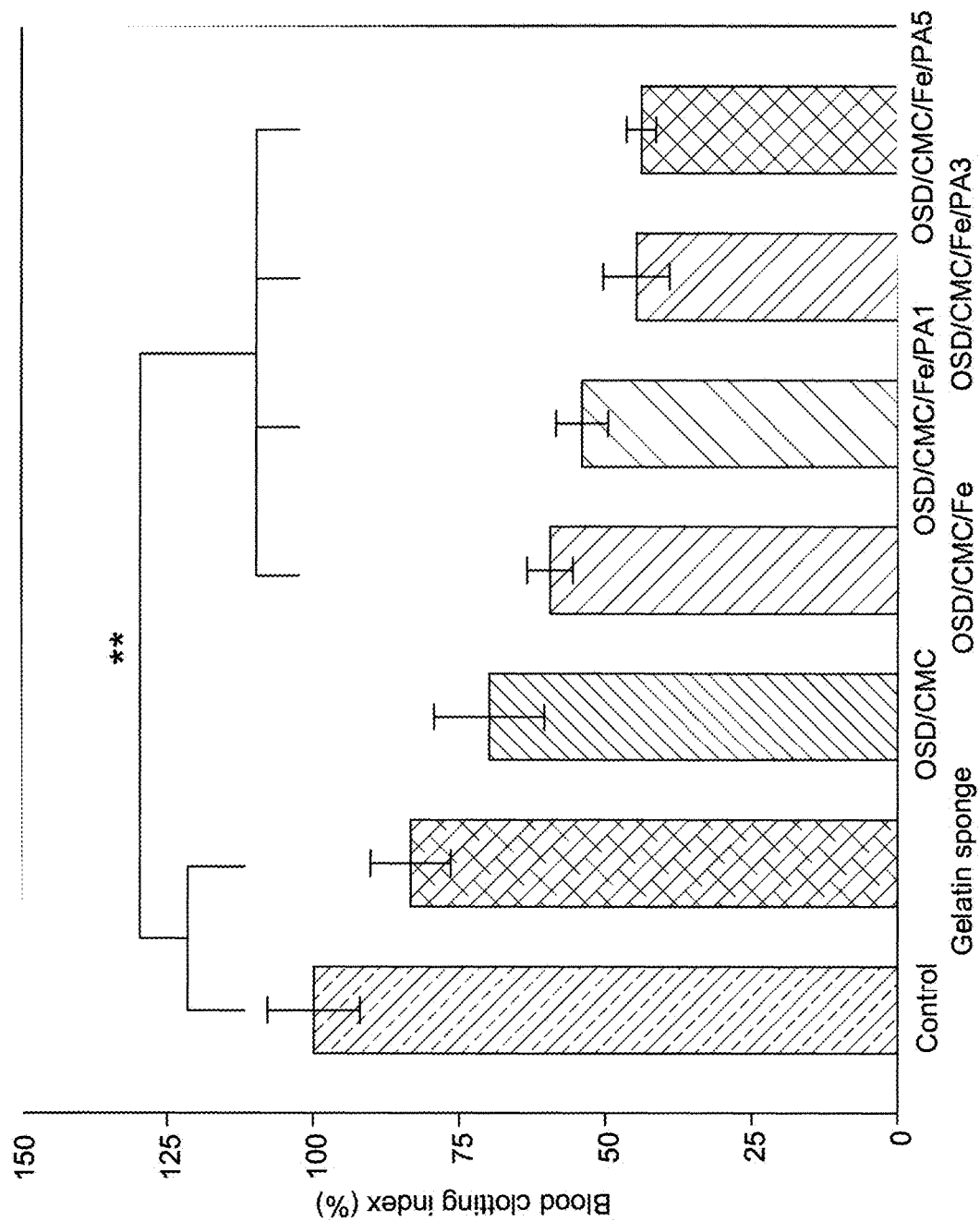
FIG. 7F depicts the coagulation properties of gauze and hydrogels according to certain embodiments.

To further test the in-vivo haemostatic properties of these dressings, a mouse liver puncture model was constructed to test the haemostatic properties of OSD/CMC/Fe/PA hydrogels, as shown in FIG. 7D. Regardless of the OSD/CMC hydrogel, OSD/CMC/Fe hydrogel and OSD/CMC/Fe/PA3 hydrogel had good haemostatic effects, and their blood loss was 90.98 mg, 62.6 mg, and 30.05 mg, respectively. The values are lower than the commercial gelatine sponge group (209.33 mg) and the control group (532.43 mg). In conclusion, the OSD/CMC/Fe/PA3 hydrogel with appropriate haemostatic ability was chosen to represent multifunctional dressing.

Figure 7G:
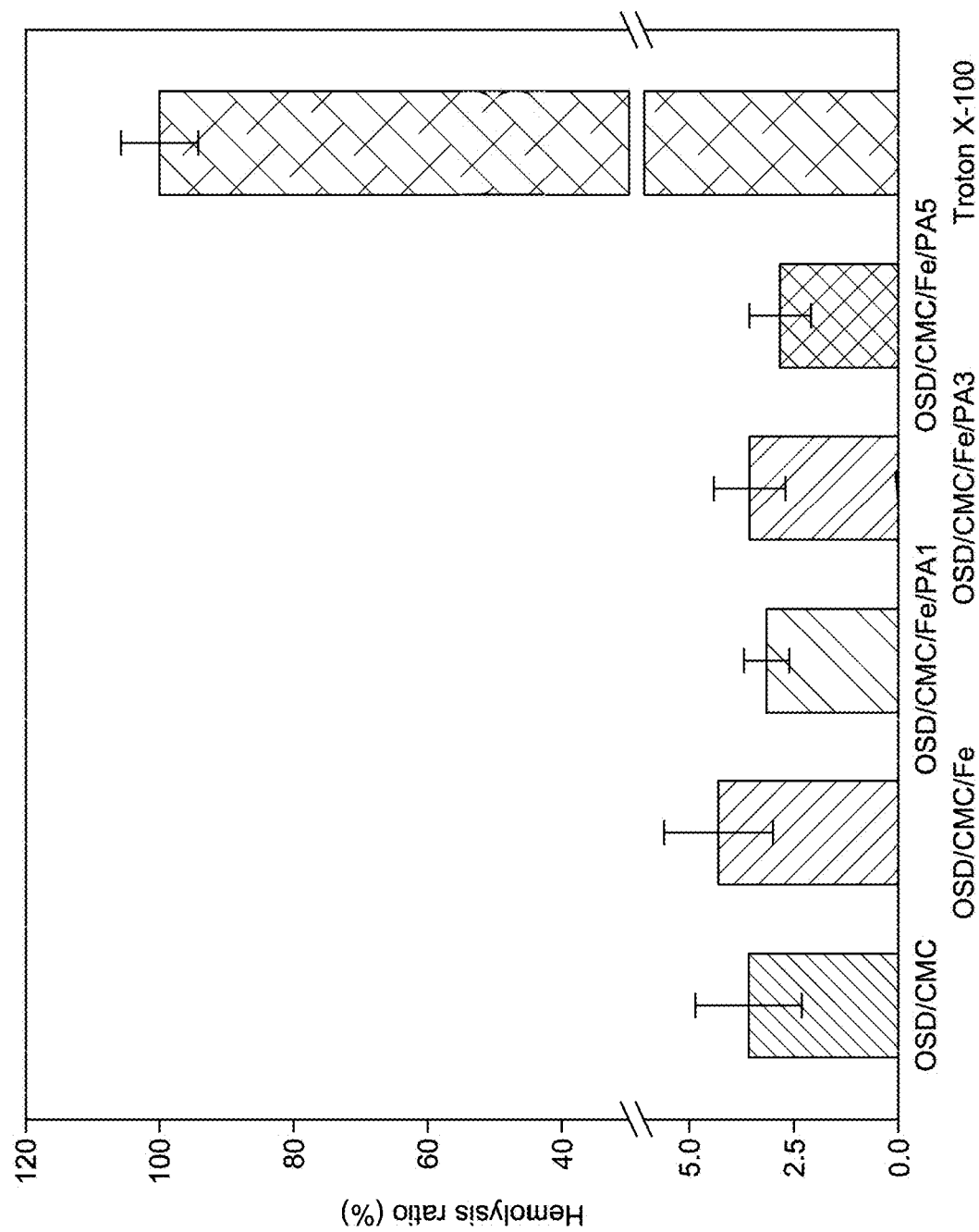
FIG. 7G depicts haemolytic activity test results of the hydrogels, according to certain embodiments.
Figure 7H:
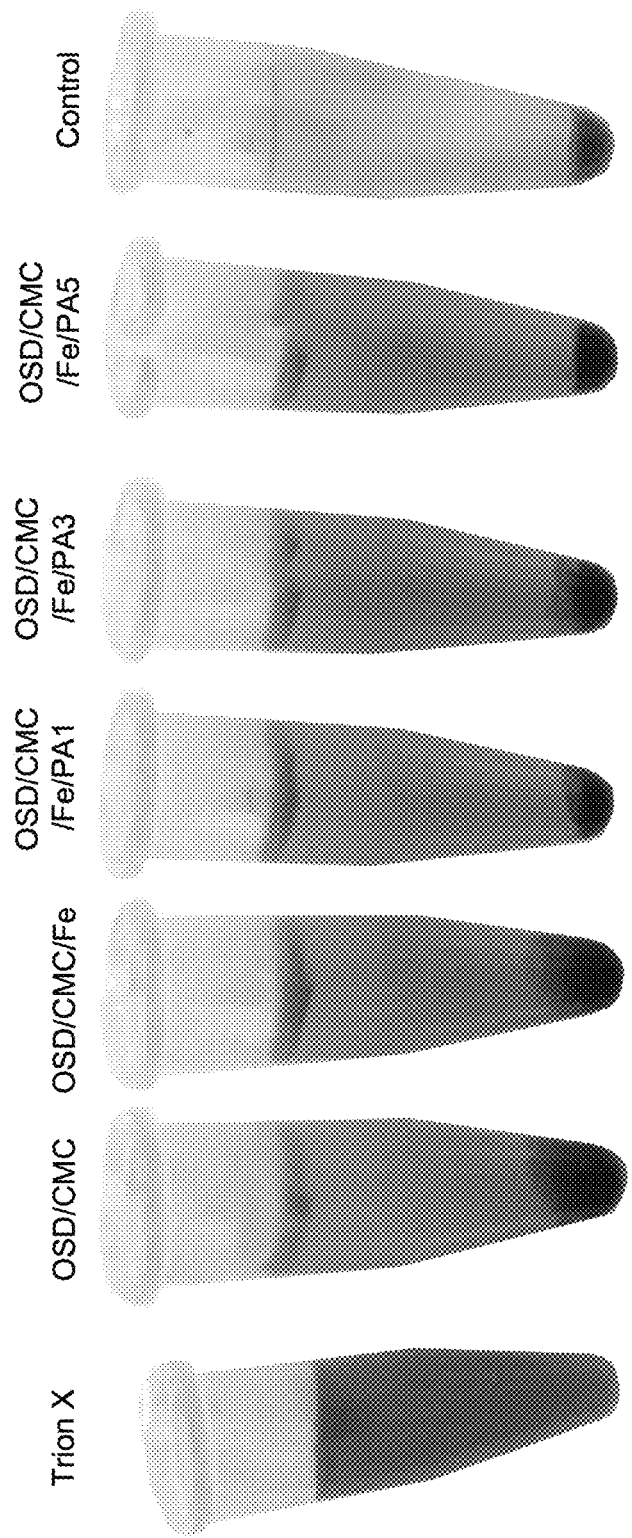
FIG. 7H shows the hydrogel haemolytic activity test graphs, according to certain embodiments.
Figure 7I:
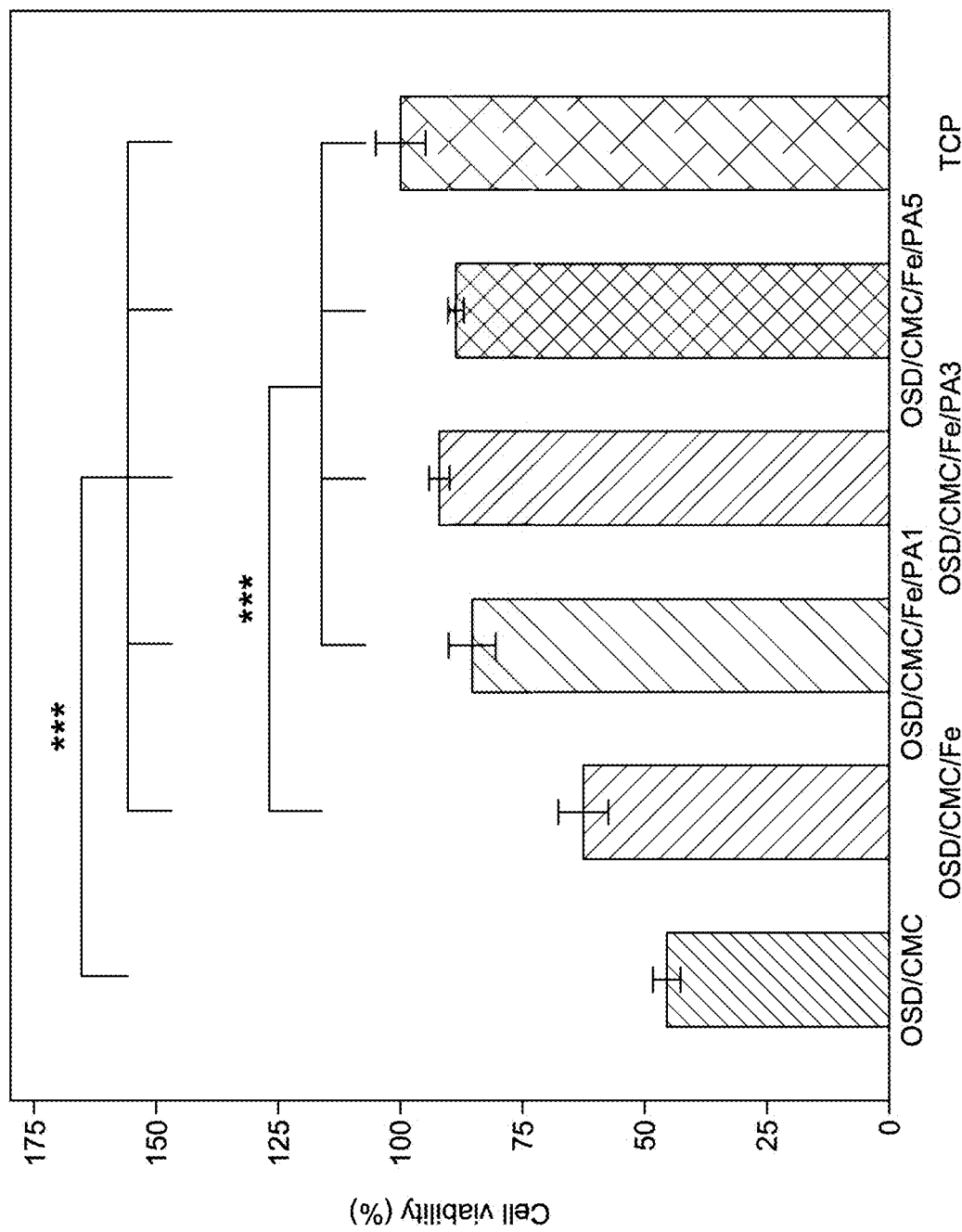
FIG. 7I depicts the cytocompatibility of the hydrogels according to certain embodiments.
Figure 7J:
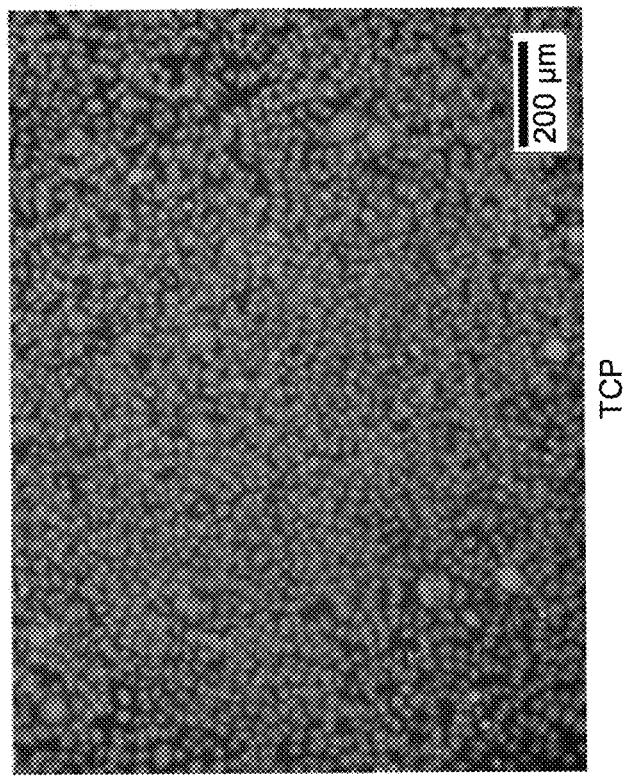
Figure 7J:
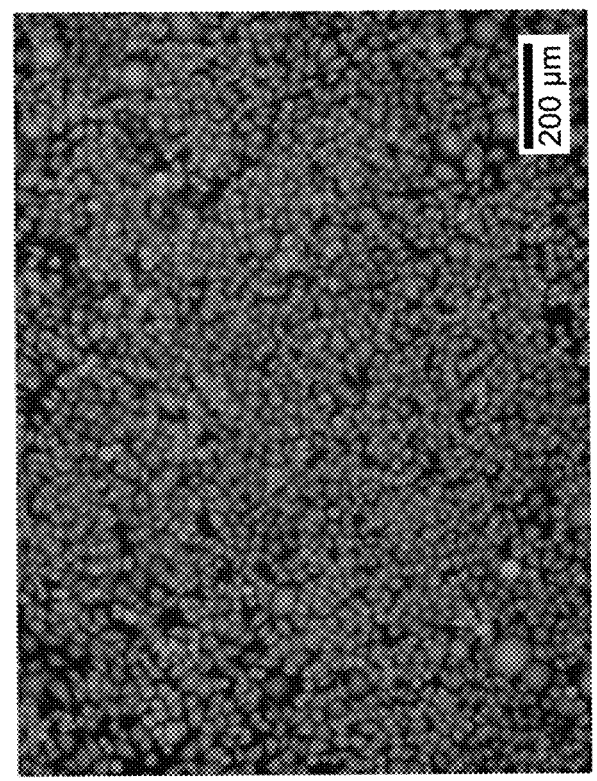
Figure 7K:
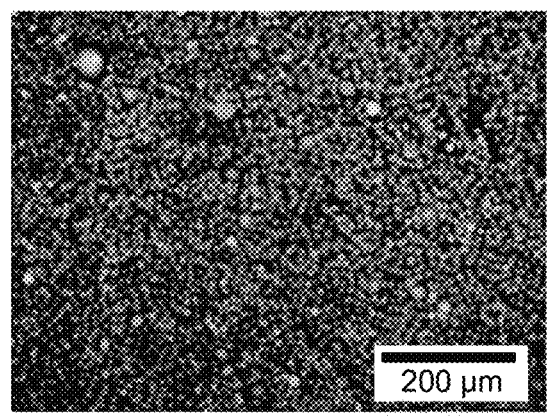
Figure 2:
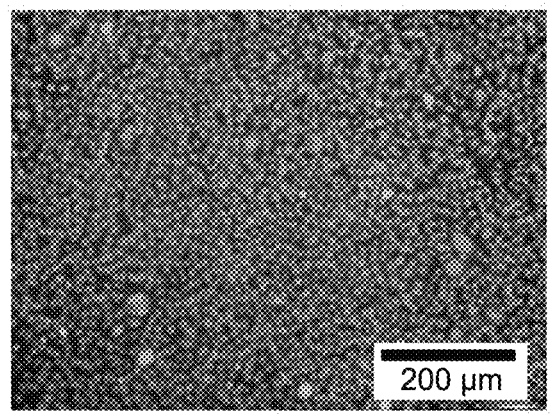
Figure 9A:
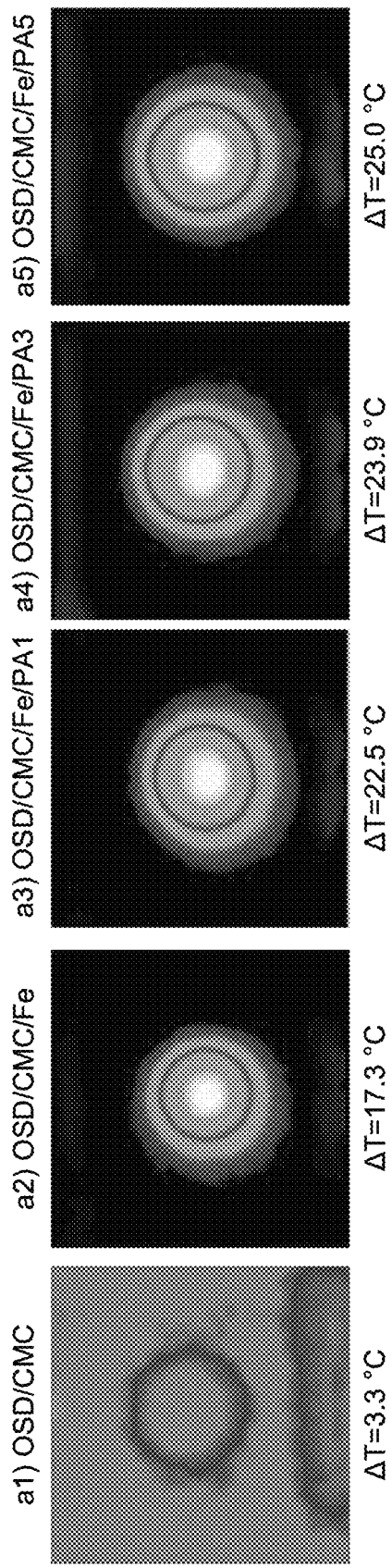
FIG. 9A shows heat maps of OSD/CMC, OSD/CMC/Fe, OSD/CMC/Fe/PA1, OSD/CMC/Fe/PA3, and OSD/CMC/Fe/PA5 hydrogels after 10 minutes of 808 nanometers of near-infrared (NIR) radiation, according to certain embodiments.
Figure 9B:
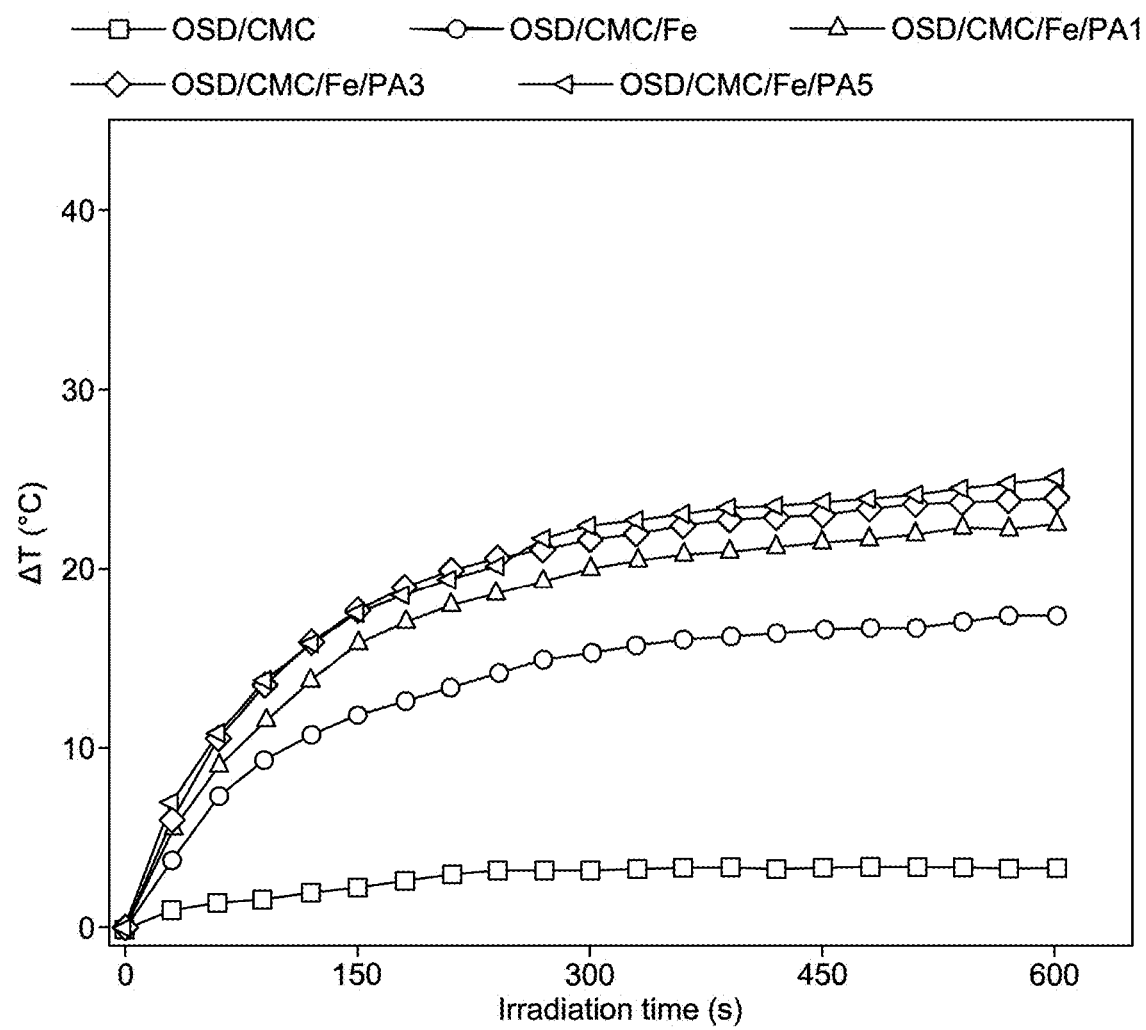
FIG. 9B depicts the temperature change ($\Delta T$) versus NIR radiation time curve of the hydrogel under 1.4 W cm$^{-2}$, 808 nm NIR light irradiation, according to certain embodiments.

The dressing adheres to the wound surface during wound treatment and needs to have a high level of hemocompatibility from the point of view of biocompatibility. A haemolysis test was chosen to evaluate the hemocompatibility of the hydrogel. The data in FIG. 7G exhibits a haemolysis ratio of less than 5% (<5% for good hemocompatibility) for the whole hydrogel groups, indicating that the hydrogels have good hemocompatibility. Cytocompatibility is another important aspect of biocompatibility. The Leachate method of L929 cells was selected for testing the cytocompatibility of hydrogels. As shown in FIG. 7I, the OSD/CMC/Fe/PA1 hydrogel and OSD/CMC/Fe/PA3 hydrogel groups have good biocompatibility (cell viability >80%), and the LIVE/DEAD staining diagram in FIG. 7J and FIGS. 7K-1 and 7K-2 also confirms the same result. Dopamine-encapsulated PA has dual photothermal components, which may have excellent photothermal properties. The change of hydrogel temperature with irradiation time was tested under 808 nanometres (nm) near-infrared (NIR) light irradiation to evaluate its photothermal properties. FIG. 9A depicts a plurality of optical images of the photothermal performance test. As illustrated in FIG. 9B, the ΔT of OSD/CMC hydrogel is only 3.3° C. after 10 min illumination because no photothermal agent is added. However, the photothermal performance of OSD/CMC/Fe hydrogel was improved due to the oxidation of dopamine by $Fe^3$, and its ΔT was found to increase to 17.3° C. Further, the OSD/CMC/Fe/PA1, OSD/CMC/Fe/PA3, and OSD/CMC/Fe/PA5 hydrogels with the addition of PA have improved photothermal performance. Furthermore, the ΔT gradually increased with the addition of PA, and the ΔT of OSD/CMC/Fe/PA1, OSD/CMC/Fe/PA3, and OSD/CMC/Fe/PA5 hydrogels were noted to be 22.5° C., 23.9° C., and 25.0° C., respectively. The photothermal test proved that the OSD/CMC/Fe/PA hydrogels had good photothermal properties.

Figure 9C:
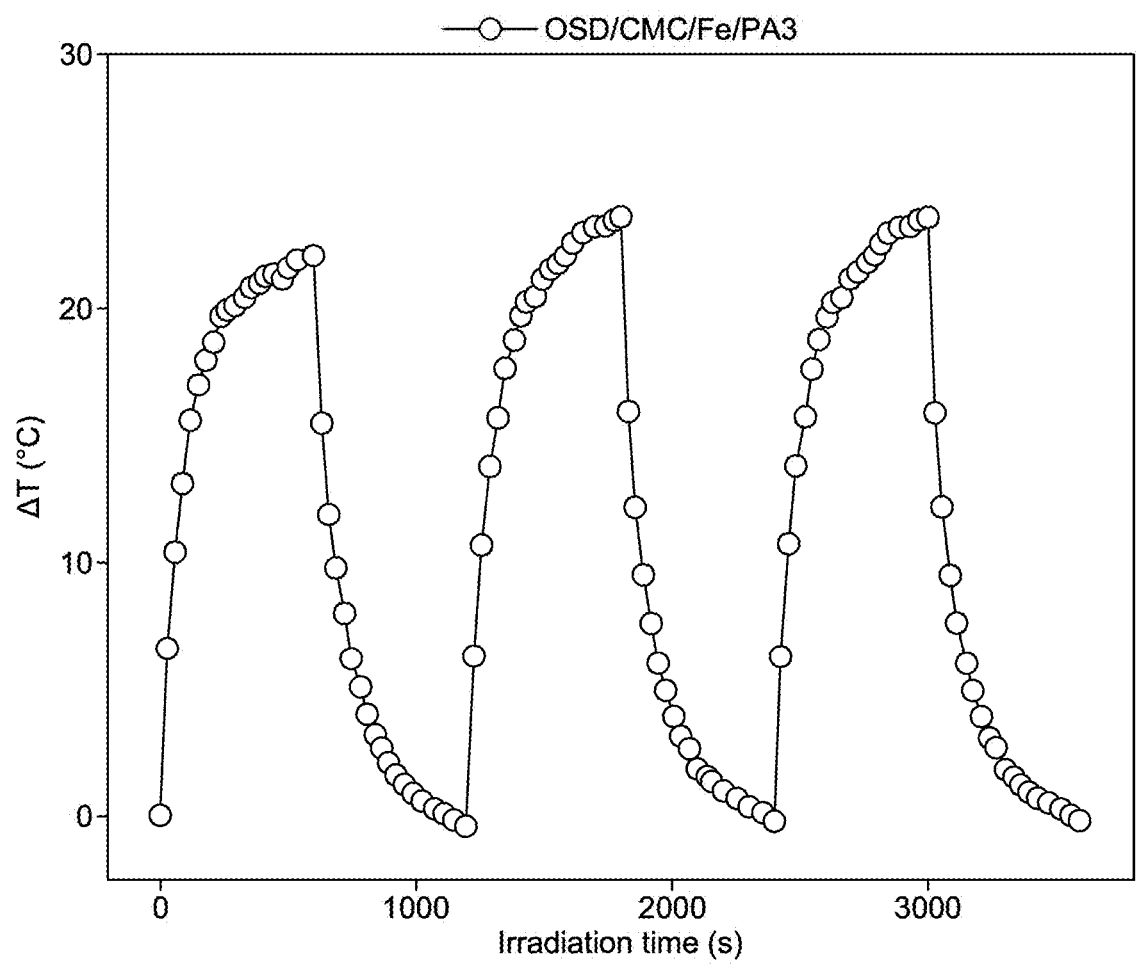
FIG. 9C is a graph depicting $\Delta T$ versus irradiation cycle curves of OSD/CMC/Fe/PA3 hydrogels at 1.4 W cm$^{-2}$ light intensity of 808 nm NIR light, according to certain embodiments.

Stable photothermal properties have important implications for wound dressings. The OSD/CMC/Fe/PA3 hydrogel was selected as a representative hydrogel, and the stability of the photothermal properties of the hydrogel was examined by three cycles of photothermal tests at 808 nm at 1.4 W $cm^2$. The results show that OSD/CMC/Fe/PA3 hydrogel has stable cyclic photothermal performance with the ΔT stable above 23° C. under three cycles, as shown in FIG. 9C. This lays a solid foundation for hydrogels to repair the infected wounds.

Figure 9D:
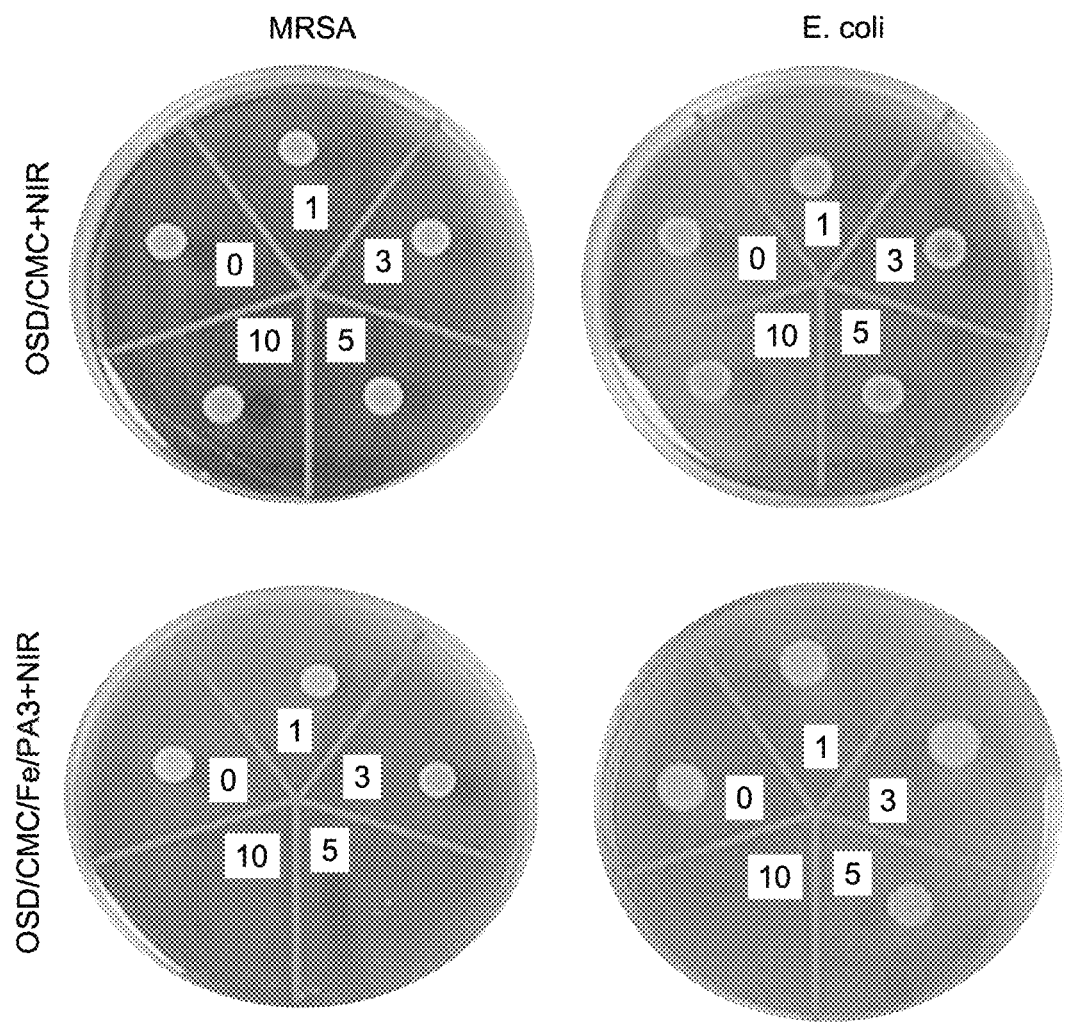
FIG. 9D are optical images of in-vitro antibacterial activity of hydrogels irradiated with NIR light for 0, 1, 3, 5, and 10 minutes, respectively, according to certain embodiments.
Figure 9E:
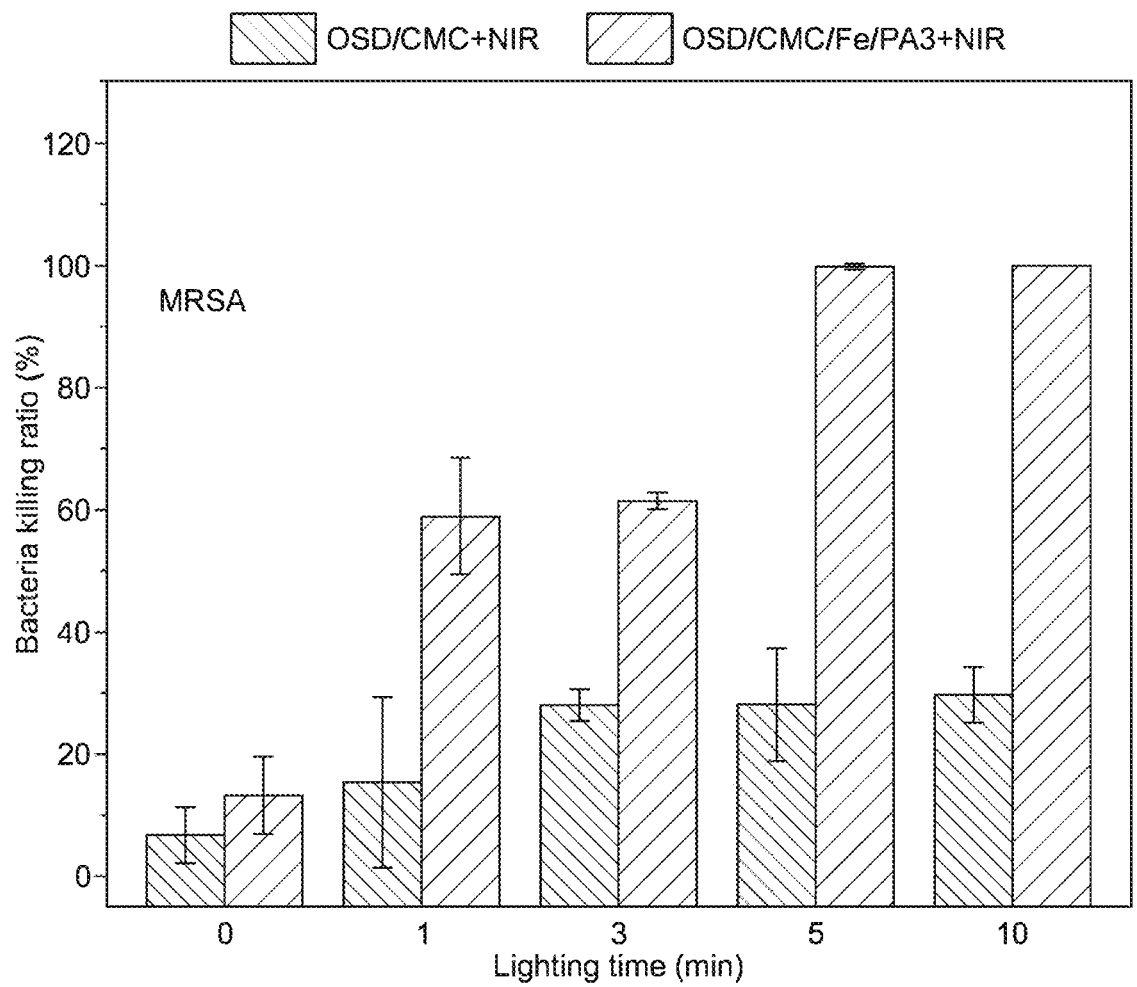
FIG. 9E depicts the killing ratio of Methicillin-resistant Staphylococcus aureus (MRSA) for different irradiation timing, according to certain embodiments.
Figure 9F:
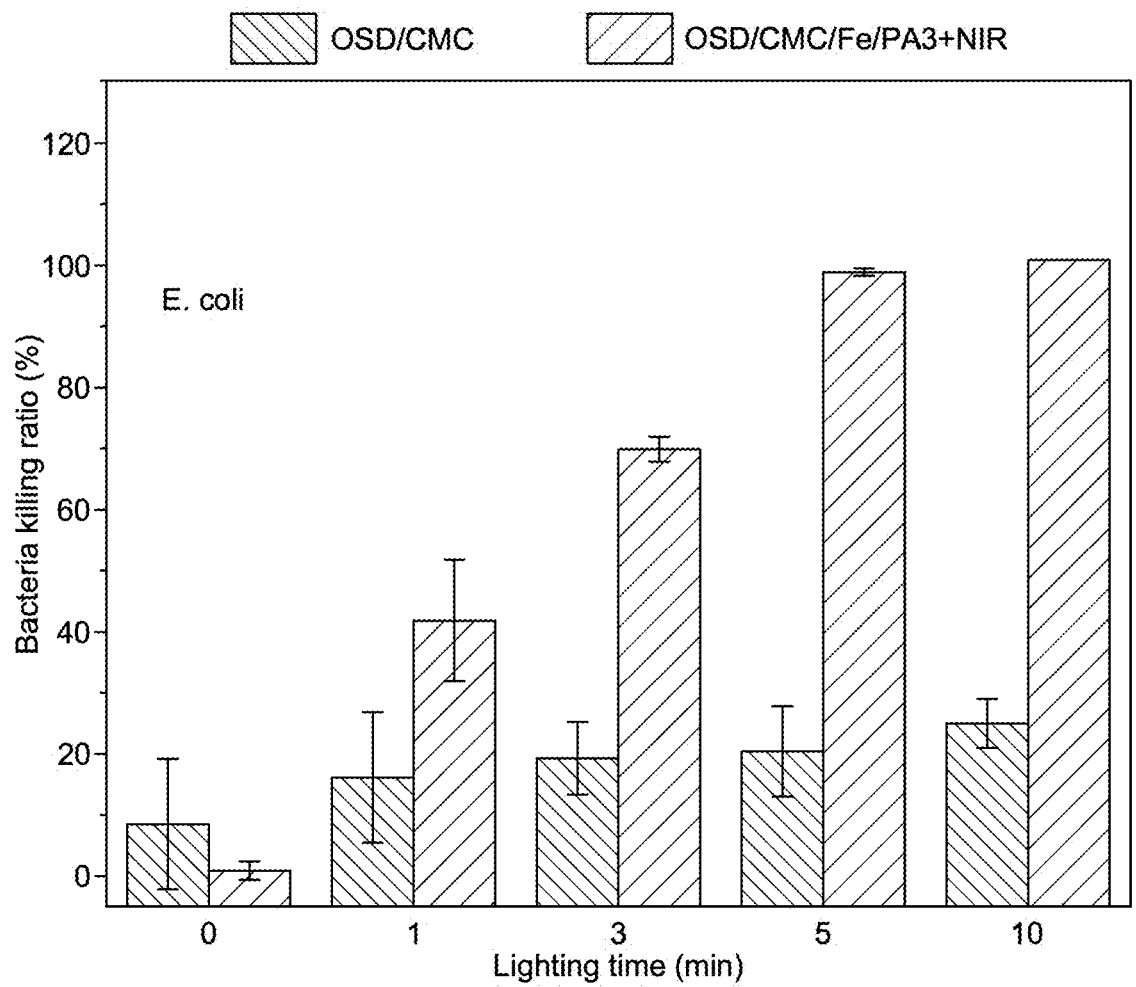
FIG. 9F depicts the killing ratio of E. coli for different irradiation timings, according to certain embodiments.

Based on the test results above, the photothermal antibacterial ability of these hydrogels was further evaluated by selecting Escherichia coli (E. coli) and methicillin-resistant Staphylococcus aureus (MRSA) as representative bacteria. FIG. 9D is an in-vitro photothermal antibacterial display image of OSD/CMC and OSD/CMC/Fe/PA3 hydrogels. Compared with OSD/CMC hydrogel+NIR, OSD/CMC/Fe/PA3 hydrogel+NIR may kill more than 99% of MRSA in about 5 min of light irradiation and may kill all E. coli within 10 min, as shown in FIG. 9E and FIG. 9F, respectively. Glutaraldehyde fixation of bacteria was performed after photothermal treatment of different hydrogels, and their SEM images were taken. As shown in FIGS. 10A-10D, the OSD/CMC+NIR treated bacteria exhibited an intact bacterial structure with a smooth bacterial surface, indicating that the bacteria were not significantly damaged. However, after OSD/CMC/Fe/PA3+NIR treatment, both bacteria exhibited irregular morphological shrinkage and increased surface roughness, indicating that the integrity of the bacteria was severely damaged, leading to leakage of contents and protein denaturation. The strong antibacterial performance of OSD/CMC/Fe/PA3 results from its photothermal properties and the synergistic effect of antibacterial substances such as carboxymethyl chitosan and $Fe^{3+}$.

Figure 9G:
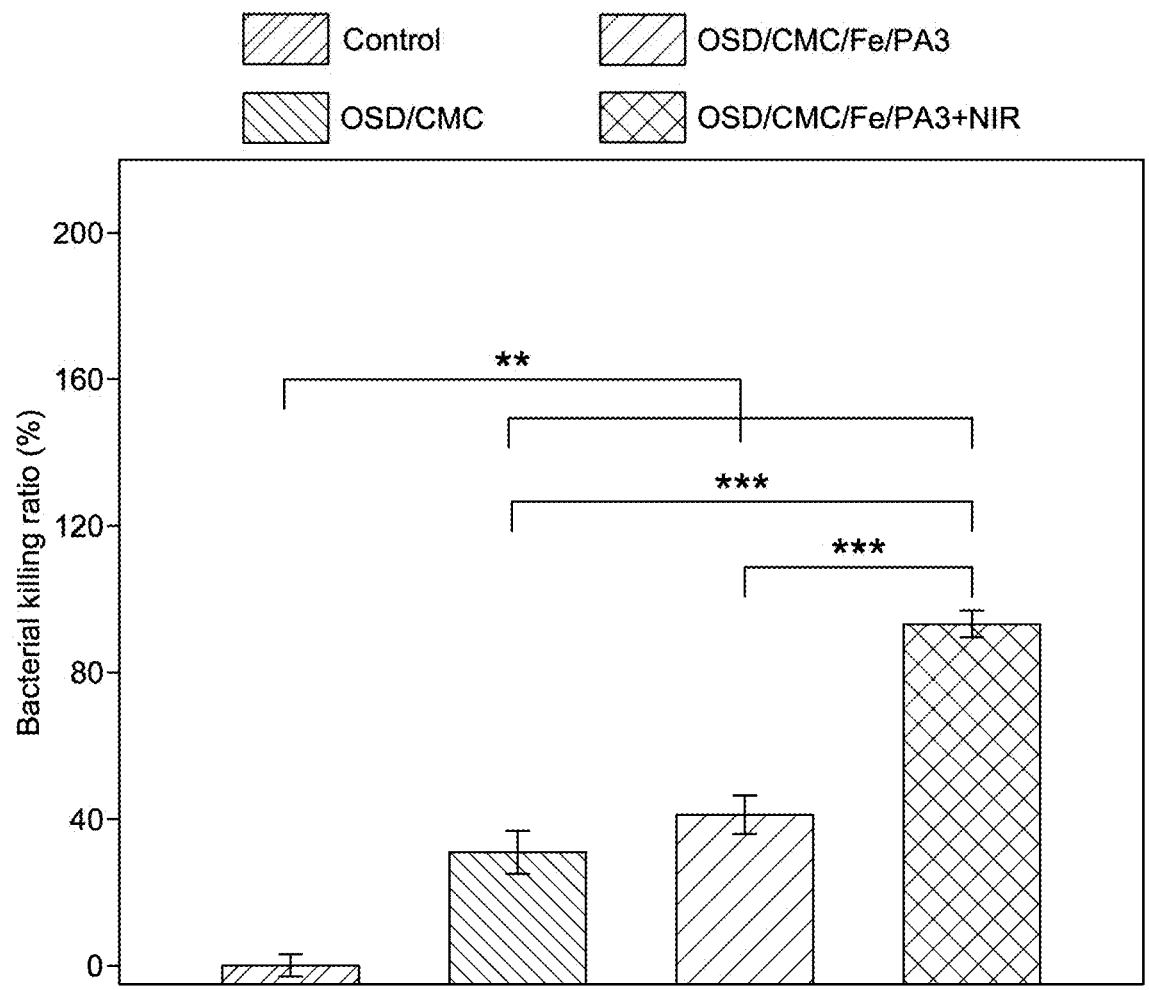
FIG. 9G depicts the in-vivo antibacterial activity results of the hydrogels, according to certain embodiments.

An in-vivo antibacterial test was carried out in a mouse skin wound model infected with MRSA to examine the in-vivo photothermal antibacterial properties of the hydrogel in depth. As shown in FIG. 9G, after different treatments and bacterial cultures of infected tissue, the test results showed high bacterial survival in control (treated with PBS) and in the wounds treated with OSD/CMC hydrogel. However, in the wounds treated with OSD/CMC/Fe/PA3 hydrogel and applying 10 min of NIR irradiation, bacterial survival was extremely low at about 6.9%. The OSD/CMC/Fe/PA3 hydrogel+NIR group also significantly differed from the other three groups (P<0.01). Moreover, there was no significant difference in bacterial survival between OSD/CMC and OSD/CMC/Fe/PA3 hydrogel groups, suggesting that the photothermal effect provided by PA and complexes of $Fe^{3+}$ with catechol is the source of the antibacterial properties of OSD/CMC/Fe/PA3.

Figure 11A:
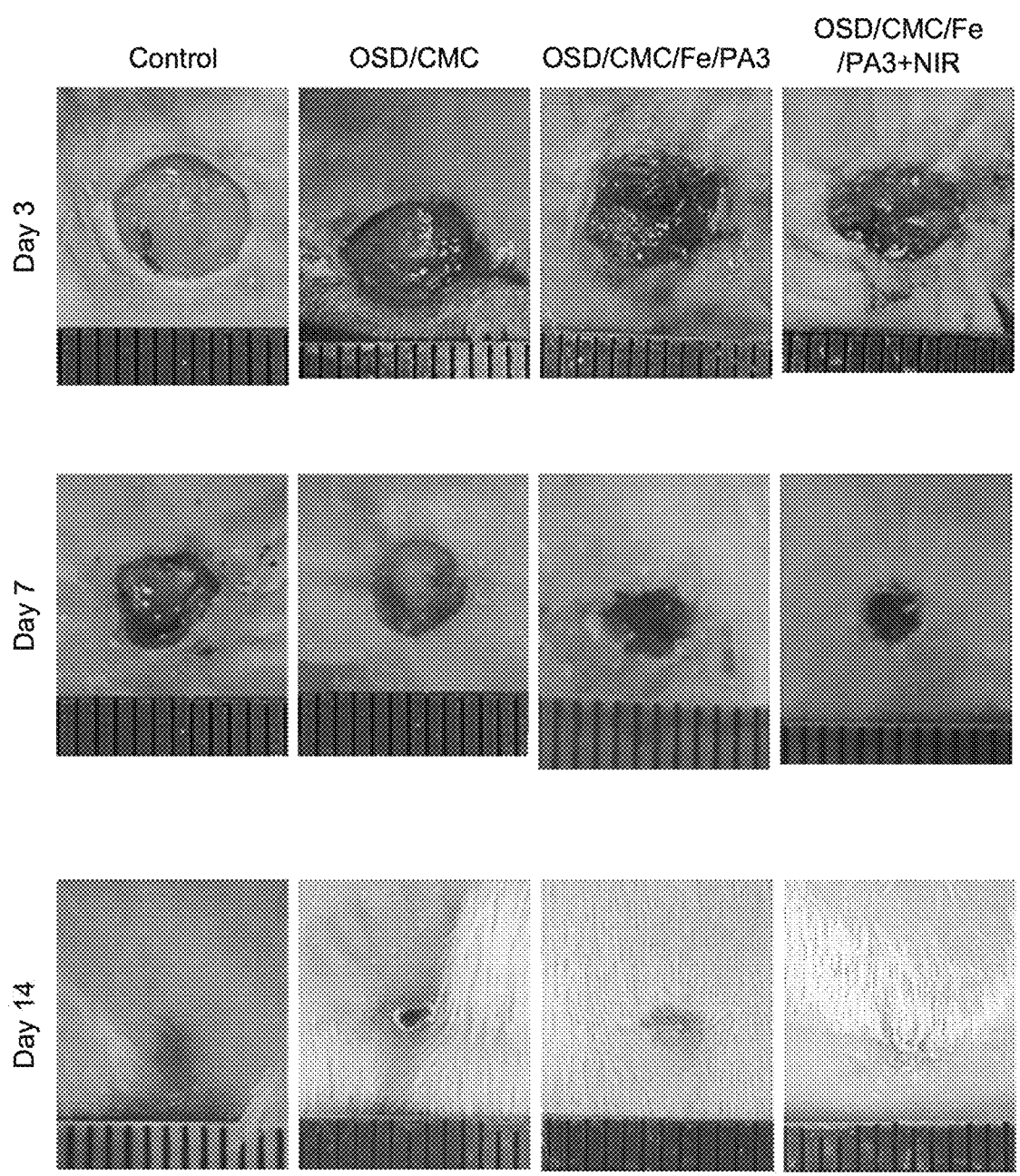
FIG. 11A shows optical images of wounds in the control group using Tegaderm™ film dressing, OSD/CMC hydrogel, OSD/CMC/Fe/PA3 hydrogel, and OSD/CMC/Fe/PA3 hydrogel+NIR on days 3, 7, and 14, respectively, according to certain embodiments.
Figure 11B:
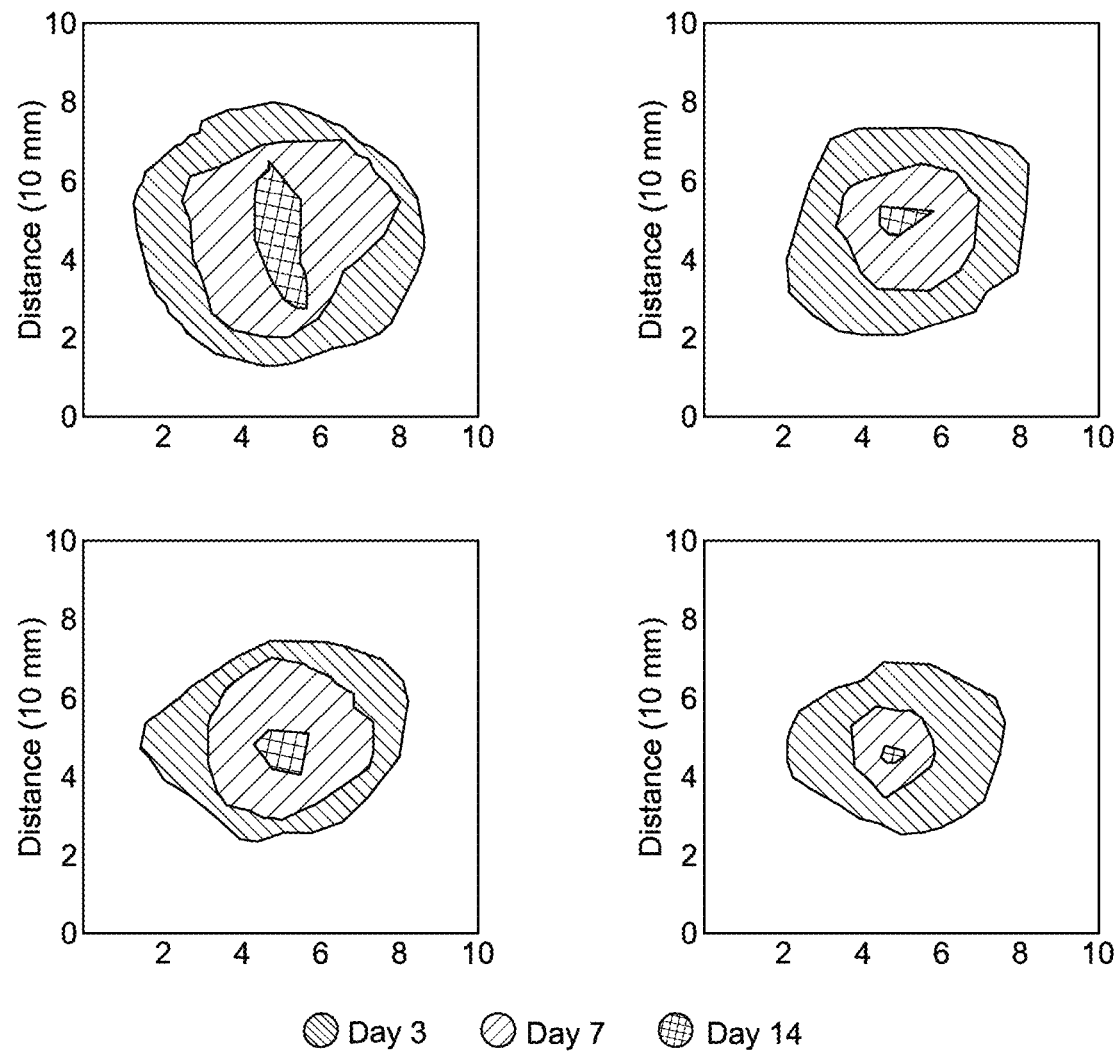
FIG. 11B depicts a plurality of schematic diagrams of wound area of control (b1), OSD/CMC hydrogel (b2), OSD/CMC/Fe/PA3 hydrogel (b3), and OSD/CMC/Fe/PA3 hydrogel+NIR (b4) for 14 days, according to certain embodiments.
Figure 11C:
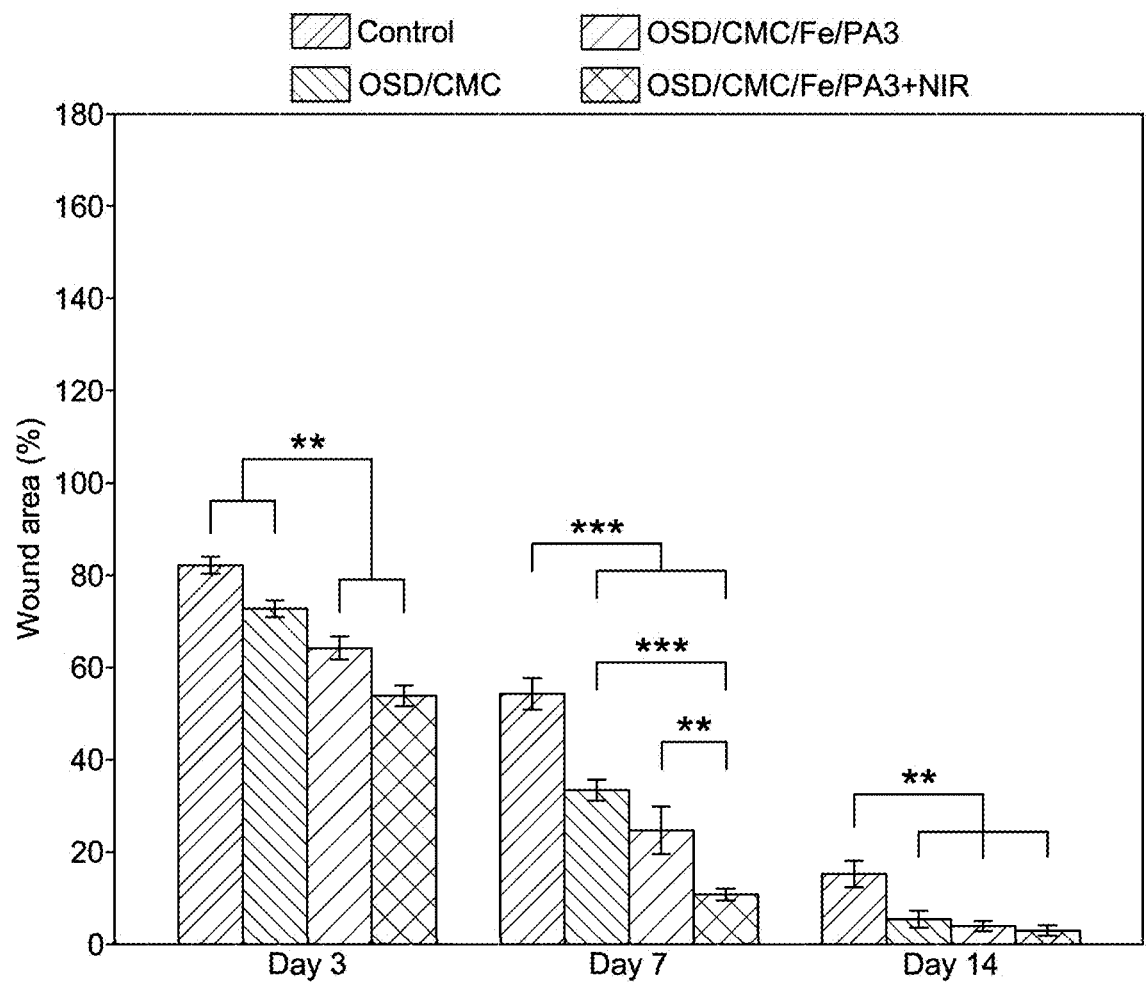
FIG. 11C depicts the wound area percentage of each group according to certain embodiments.

A mouse full-thickness defect infection model was established to comprehensively evaluate the healing-promoting properties of OSD/CMC/Fe/PA hydrogels as wound dressings. OSD/CMC/Fe/PA3 with good biocompatibility, good conductivity, and NIR light-assisted antibacterial properties were selected as the experimental group, and Tegaderm™ film commercial product was selected as the control group. As illustrated in FIGS. 11A-11D, the wound size of the entire group gradually decreased over time. Wounds treated with OSD/CMC hydrogel, OSD/CMC/Fe/PA3 hydrogel, and OSD/CMC/Fe/PA3 hydrogel+NIR were smaller than the control group after 3 days of wound healing. In addition, the wounds treated in the OSD/CMC/Fe/PA3 hydrogel+NIR and OSD/CMC/Fe/PA3 hydrogel groups were significantly different from the OSD/CMC hydrogel and control groups (P<0.001), indicating that the hydrogels with the addition of conductive PTAA had better promotion of repair. After 7 days of wound treatment, all three hydrogel groups had a higher wound repair ratio than the control group. After 14 days, the wounds of all groups were largely healed, and the wounds of the hydrogel treatment group were completely closed and even covered by hair. Statistical analysis of the wound area throughout the healing procedure showed that the wound closure ratio of the OSD/CMC/Fe/PA3 hydrogel and OSD/CMC/Fe/PA3 hydrogel+NIR treatments groups were 95.5% and 97.02% respectively, and 85.01% for the Tegaderm™ film dressing, as shown in FIG. 11C. The repair effect of the OSD/CMC/Fe/PA3 hydrogel+NIR group was the best, demonstrating that conductivity and photothermal antibacterial properties may speed up the repair of infected wounds.

Figure 11D:
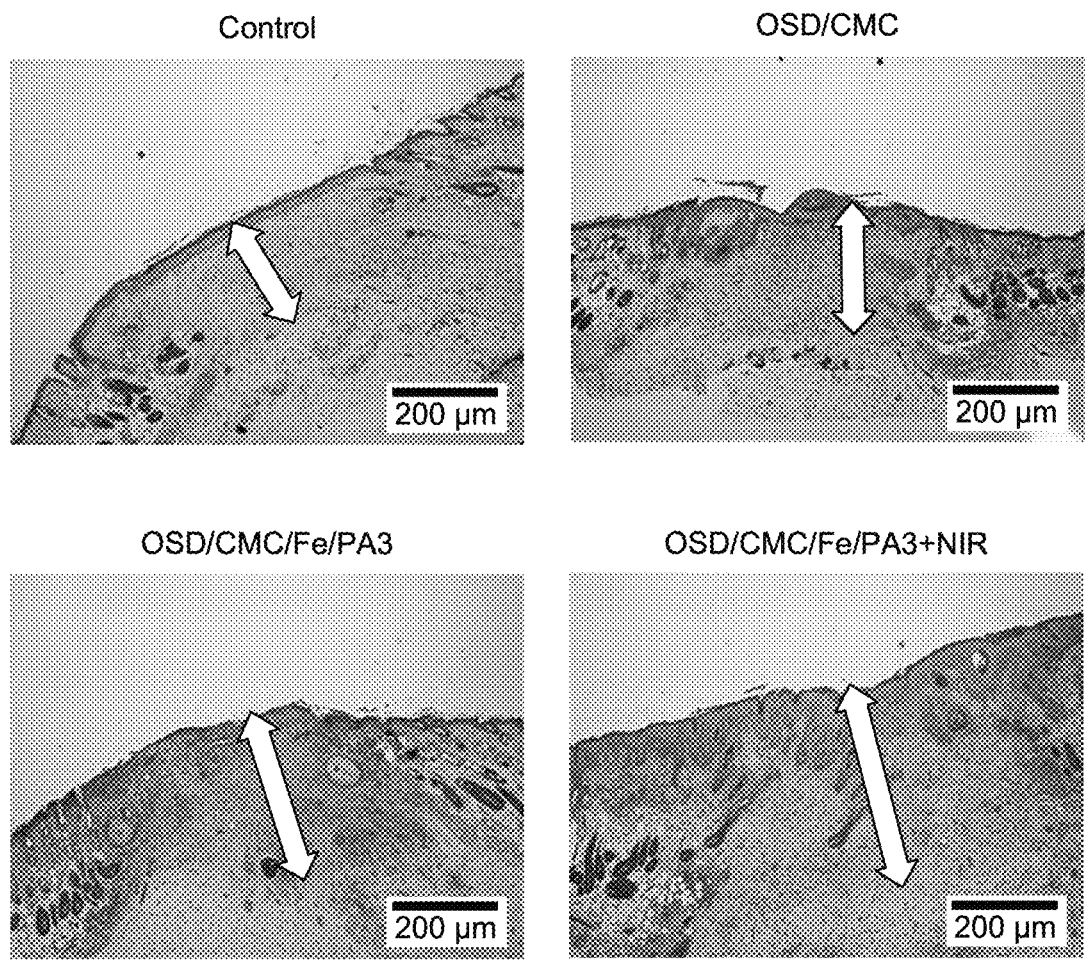
FIG. 11D are optical images depicting thickness of granulation tissue in different groups on day 14, according to certain embodiments.

In conclusion, these in-vivo experiments show that hydrogels with haemostatic, conductive, and adhesive properties show great potential for wound healing compared to the control. In the wound repair procedure of inflammation, parenchymal cells have difficulty completing the repair work. Granulation tissue is of vital importance in the repair process. Granulation tissue generally completes wound repair by proliferating to dissolve and absorb necrotic tissue and foreign bodies, filling the gaps, and finally transforming into scar tissue. Therefore, the thickness of granulation tissue during wound healing is an important index to assess the effectiveness of wound healing. The results, as shown in FIG. 11D depicts that the granulation tissue thickness in the control group was thinner than all hydrogel groups after 14 days of treatment. In the hydrogel group, the granulation tissue under OSD/CMC/Fe/PA3 hydrogel+NIR treatment was thicker than the OSD/CMC/Fe/PA3 hydrogel group and OSD/CMC hydrogel, whereas for the OSD/CMC/Fe/PA3 group the thickness of the granulation tissue was thicker than the OSD/CMC hydrogel group. The wound healing effect of all three hydrogel treatment groups was better than that of the control group, with the OSD/CMC/Fe/PA3 hydrogel+NIR group showing the best wound healing effect.

Figure 12A:
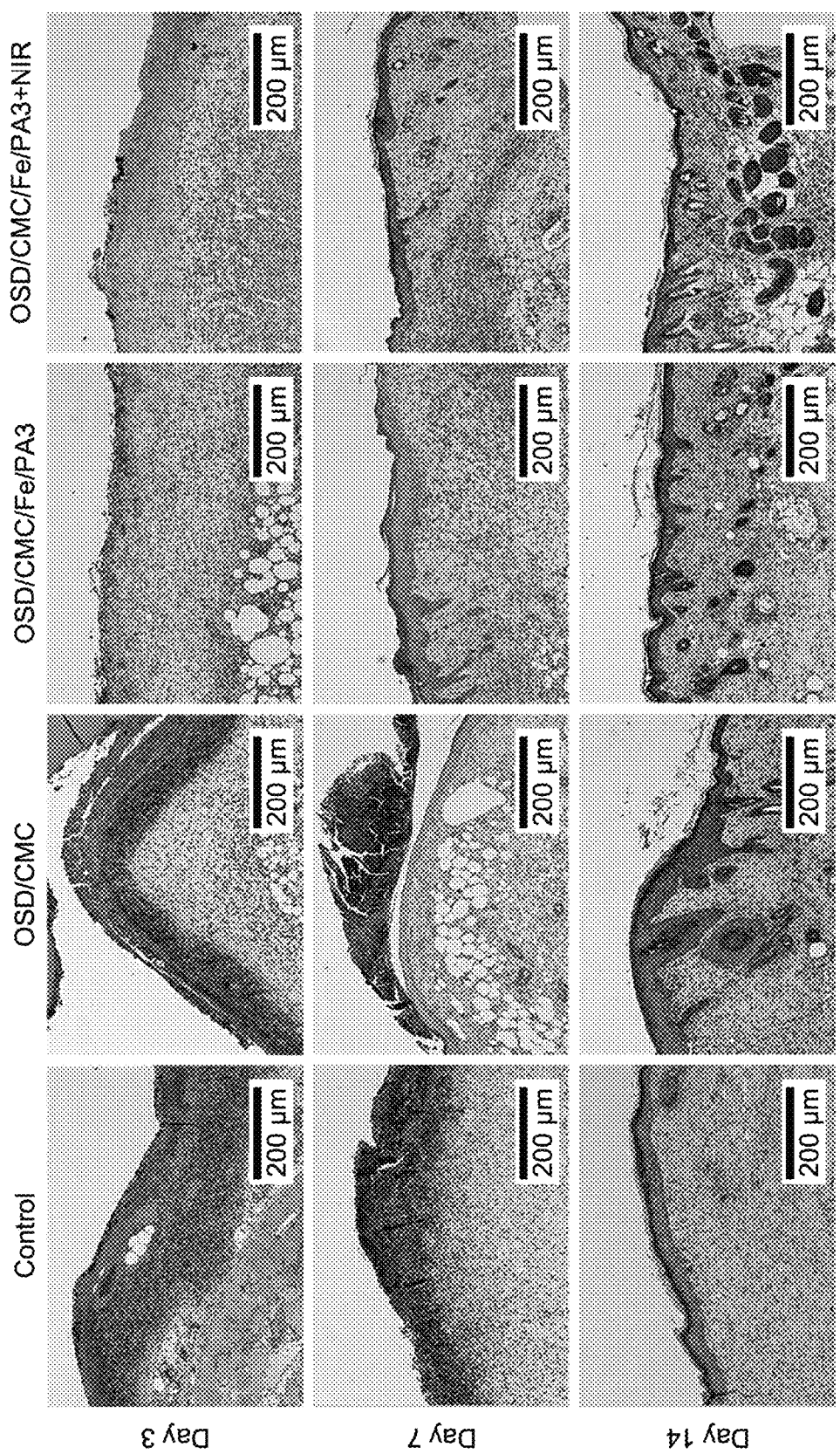
FIG. 12A shows optical images of histological analysis of wound regeneration on days 3, 7, and 14 of the control group Tegaderm™ film dressing, OSD/CMC hydrogel group, OSD/CMC/Fe/PA3 hydrogel group, and OSD/CMC/Fe/PA3 hydrogel+NIR group, according to certain embodiments.
Figure 12B:
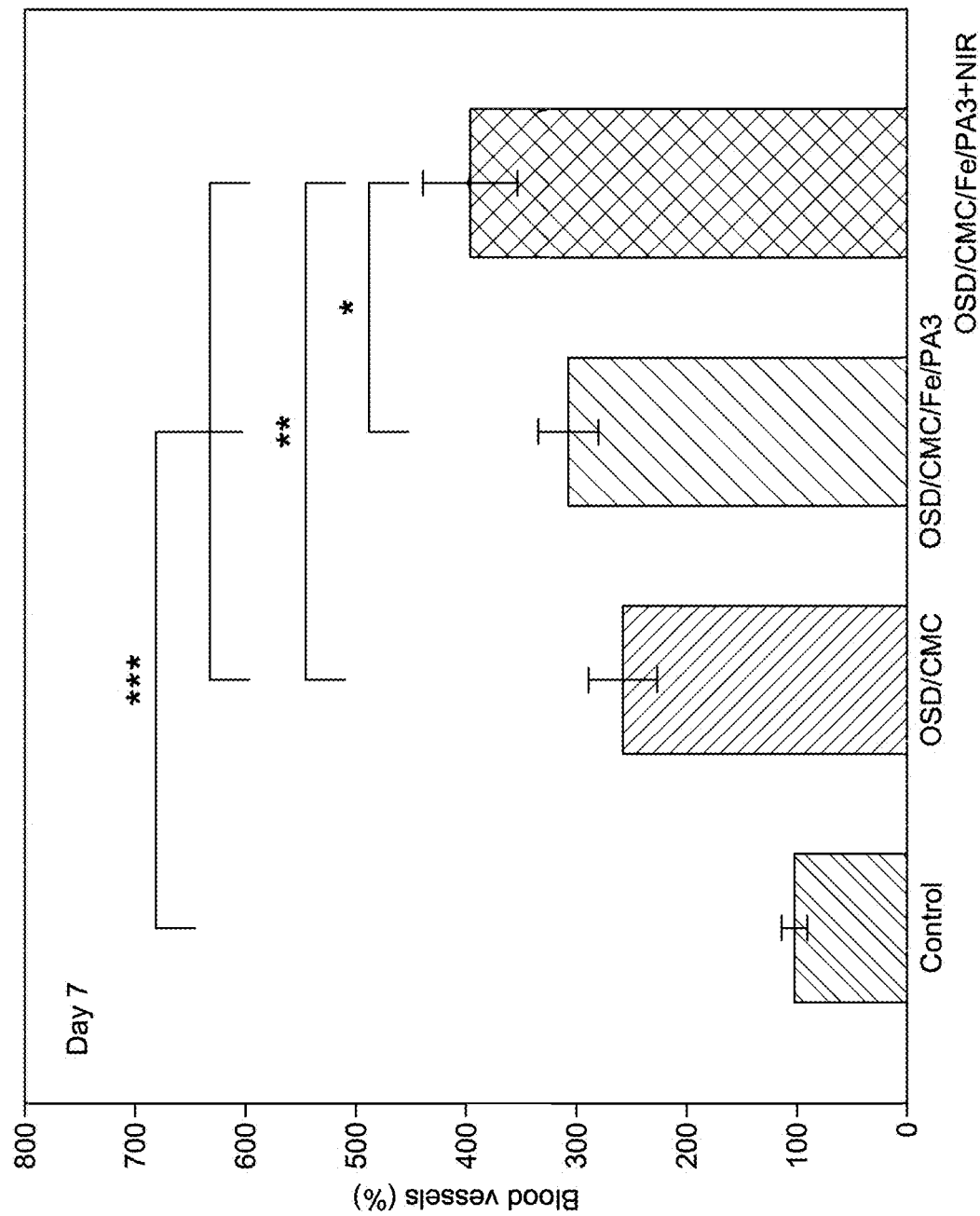
FIG. 12B is a statistical graph depicting angiogenesis on day 7 of treatment with the hydrogels, according to certain embodiments.
Figure 12C:
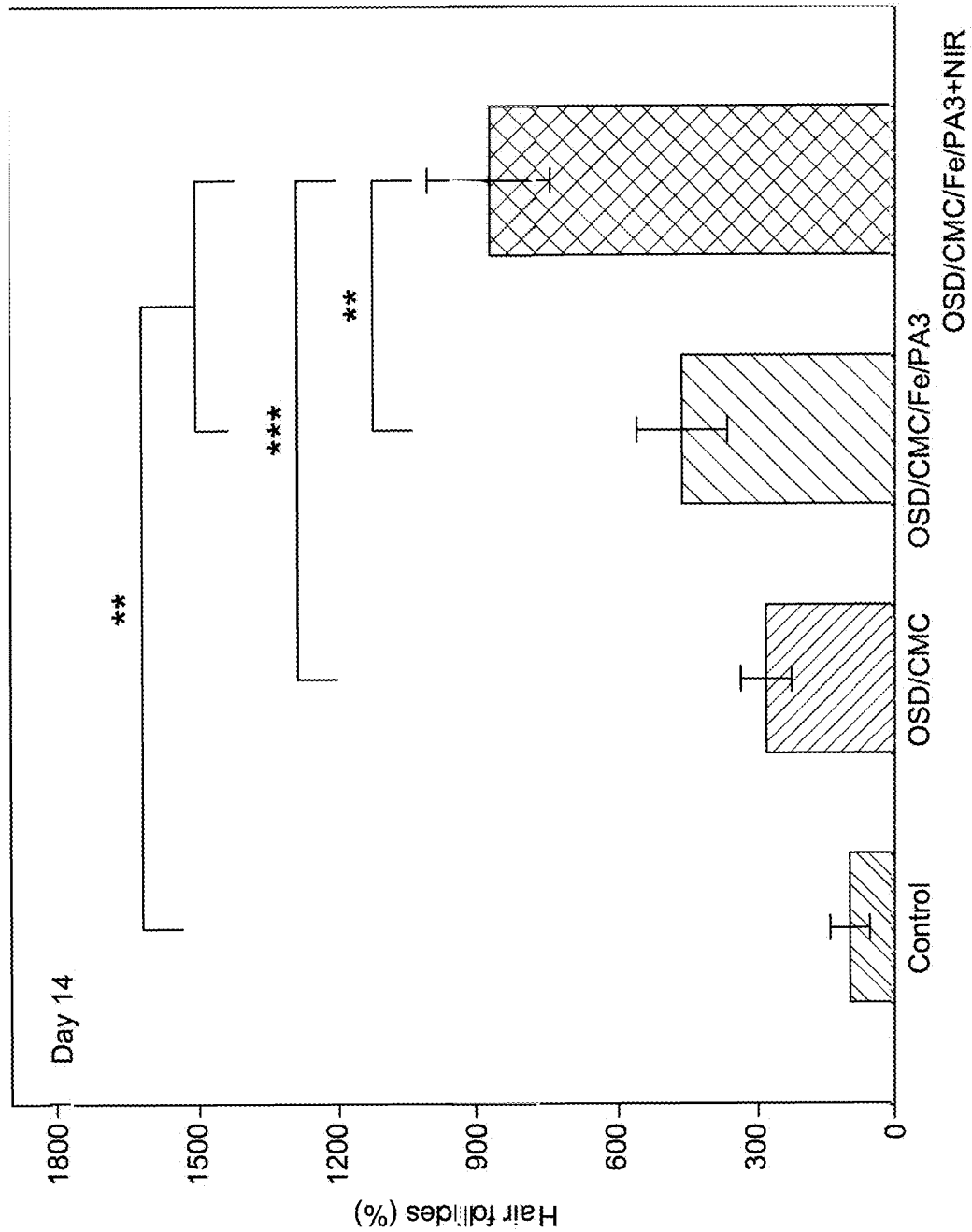
FIG. 12C is a statistical graph depicting the growth of hair follicles in different groups on the 14$^{th}$ day of treatment with the hydrogels, according to certain embodiments.

Histological analysis was performed on the four experimental groups to assess the repair effect of the regenerated skin at a deeper level, as shown in FIG. 12A. Skin of four groups of wounds was tested using hematoxylin and eosin (H&E) staining. By comparing the inflammation in the control and hydrogel groups in the initial phase of healing, it was found that the OSD/CMC/Fe/PA3 hydrogel group and the OSD/CMC/Fe/PA3 hydrogel+NIR group had lower levels of inflammation, while the wound site of the control group had a high level of inflammation, and there were more inflammatory cells than in the hydrogel group. The lower inflammation level in the OSD/CMC/Fe/PA3 hydrogel group and the OSD/CMC/Fe/PA3 hydrogel+NIR group may be due to better antibacterial properties. On day 7, the number of inflammatory cells decreased in all groups. For wound repair, new blood vessels are important for transporting nutrients, oxygen, enzymes, and bioactive factors to the wound tissue site. FIG. 12B depicts the statistical results of the number of vessels in each group derived from H&E staining on day 7. The results show that the OSD/CMC/Fe/PA3 group and the OSD/CMC/Fe/PA3 hydrogel+NIR group have more blood vessels than the control group, and the OSD/CMC/Fe/PA3 hydrogel+NIR group had the most hair follicles. For the day 14 repair results, it was observed that there were minimal skin appendages, although there was intact epithelial cell regeneration in the control group (FIG. 12C).

While the hydrogel-treated wounds, especially the OSD/CMC/Fe/PA3 group and OSD/CMC/Fe/PA3 hydrogel+NIR group hydrogels, had epithelial tissue close to normal skin, and more skin appendages were observed in the whole groups, and have significantly different (P<0.01) compared with the control group. These results suggest that hydrogels, especially those with PA, are beneficial for promoting extracellular matrix (ECM) remodeling and tissue regeneration, and photothermal enhanced antibacterial can effectively eliminate bacteria and accelerate the wound healing process. PA imparts conductivity to the hydrogel, which enhances the endogenous current at the wound site, thereby allowing neutrophils, macrophages, and keratinocytes to migrate to the wound site, promoting the regeneration of damaged skin tissue.

Figure 13C:
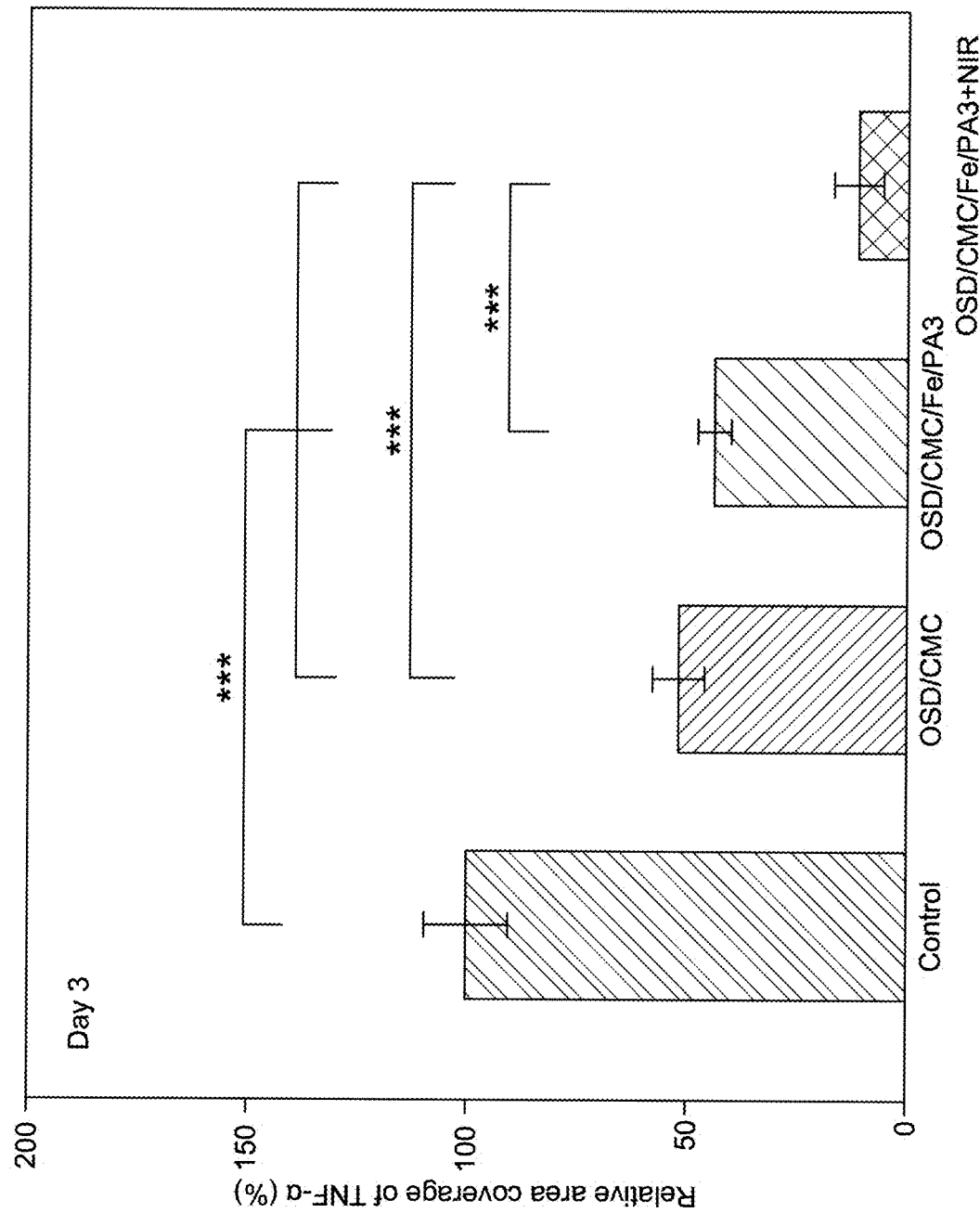
FIG. 13C is a graph depicting the relative area coverage percent of TNF-$\alpha$ for different hydrogels, according to certain embodiments.
Figure 13D:
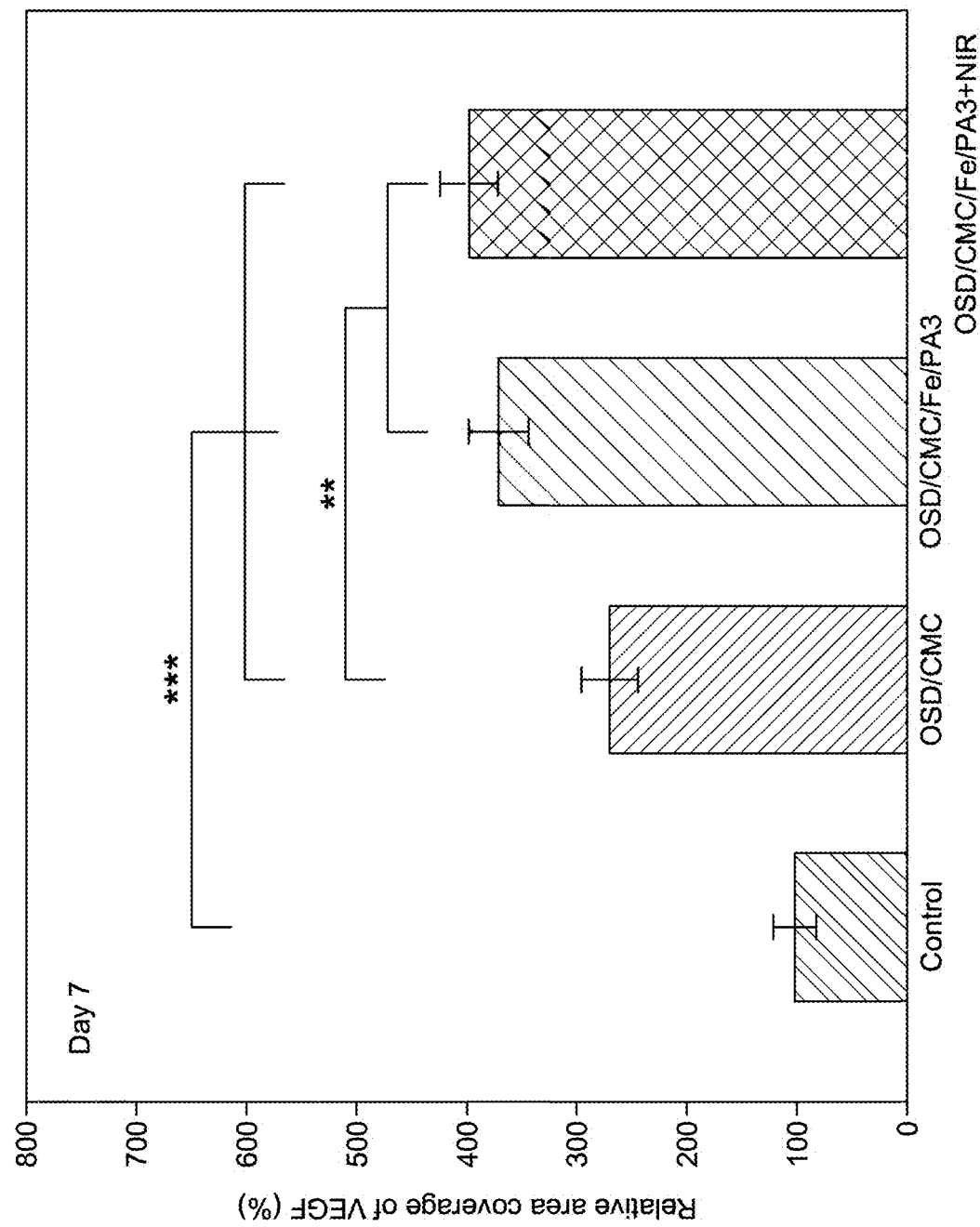
FIG. 13D is a graph depicting the relative area coverage percent of VEGF for different hydrogels, according to certain embodiments.

In general, cytokines are involved in activating and terminating many cellular activities related to repair during wound healing. The level of TNF-α at the wound site may reflect the level of tissue inflammation to some extent. Hence, TNF-α was chosen to assess the inflammation of wounds in different groups. As shown in FIG. 13A and FIG. 13C, the OSD/CMC/Fe/PA3 hydrogel +NIR group had the least amount of TNF-α compared with all other groups, proving the antibacterial properties of OSD/CMC/Fe/PA3 hydrogel+NIR can effectively reduce the inflammation caused by infection. The OSD/CMC hydrogel group and the OSD/CMC/Fe/PA3 hydrogel group were also significantly different from the control group ($p<0.001$), confirming that these hydrogels outperformed the control group. According to the present disclosure, the amount of angiogenesis at the wound site was assessed by immunohistochemical staining of the wound for VEGF on day 7 of wound healing. As shown in FIG. 13B and FIG. 13D, the wounds treated with OSD/CMC/Fe/PA3 hydrogel+NIR and OSD/CMC/Fe/PA3 hydrogel had significantly higher levels of VEGF on day 7 than the control group ($p<0.001$), indicating that the addition of conductive antibacterial component PA has advantages in promoting angiogenesis and accelerating wound closure. In conclusion, the hydrogel groups, especially the OSD/CMC/Fe/PA3 hydrogel+NIR and OSD/CMC/Fe/PA3 hydrogel groups, significantly reduced the production of pro-inflammatory factors (TNF-α) and promoted the production of VEGF, which in turn promoted wound healing, showing a higher repair effect than the control group.

To summarize, the present disclosure provides a self-healing hydrogel for wound repair. In other words, the present disclosure reveals the synthesis of a dual dynamic bond crosslinked hydrogel based on OSD and CMC with the catechol hydroxyl group in dopamine, carboxyl group in carboxymethyl chitosan and dynamic metal coordination bonds of $Fe^{3+}$. The synthesized hydrogels have excellent self-healing, adhesion, and antioxidant properties. Besides, adding PA also endows the hydrogel with efficient antibacterial properties and suitable conductivity. In addition, good tissue adhesion makes these hydrogels more competitive in wound dressing applications. Radical scavenging experiments demonstrated the excellent antioxidant properties of the hydrogels. Decreased blood loss in mouse liver injury proved that hydrogel has good haemostatic properties. The experimental results of infected full-thickness skin wound repair in mice showed that the application of OSD/CMC/Fe/PA3 hydrogel with conductive and photothermal PA showed better wound closure with blood vessels, hair follicles, and epidermis thickness closer to normal skin and less inflammation than commercial Tegaderm™ films and OSD/CMC hydrogel. Immunofluorescence staining for TNF-α and VEGF during wound healing showed that these multifunctional hydrogels can reduce inflammation and increase vascular regeneration during wound repair. All these results suggest that the multifunctional antibacterial conductive self-healing hydrogels with dual dynamic bonds are ideal candidates for infected wound dressings.

Numerous modifications and variations of the present disclosure are possible in light of the above teachings. It is therefore to be understood that within the scope of the appended claims, the invention may be practiced otherwise than as specifically described herein.

The invention claimed is:

1. A hydrogel, comprising:
a polysaccharide comprising aldehyde groups and carboxy groups;
a functionalized chitosan;
iron (III) ions; and
particles comprising a core comprising a carboxy-functionalized polythiophene and a shell comprising polydopamine.

2. The hydrogel of claim 1, wherein:
the polysaccharide is oxidized sodium alginate having grafted dopamine,
the functionalized chitosan is carboxymethyl chitosan, and
the carboxy-functionalized polythiophene is poly(thiophene-3-acetic acid).

3. The hydrogel of claim 2, wherein the hydrogel comprises, based on a total weight of the hydrogel:
3-10 wt. % of the oxidized sodium alginate;
1-5 wt. % of the carboxymethyl chitosan;
0.05-1 wt. % of the iron (III) ions; and
0.25 to 10 wt. % of the particles.

4. The hydrogel of claim 3, wherein the hydrogel comprises, based on a total weight of the hydrogel:
6 wt. % of the oxidized sodium alginate;
2.7 wt. % of the carboxymethyl chitosan;
0.2 wt. % of the iron (III) ions; and
1 to 5 wt. % of the particles.

5. The hydrogel of claim 4, wherein:
a storage modulus of the hydrogel is 22%-56% higher than that of a comparative hydrogel that is the same but does not include the particles,
a swelling ratio of the hydrogel is 8%-20% lower than that of the comparative hydrogel,
an electrical conductivity and an adhesive strength of the hydrogel is 46%-110% higher than that of the comparative hydrogel, and
an adhesive strength of the hydrogel to mammalian skin is 43%-143% higher than that of the comparative hydrogel.

6. The hydrogel of claim 2, wherein:
the hydrogel comprises a crosslinked network formed by Schiff bases between the oxidized sodium alginate and the carboxymethyl chitosan and coordination between the iron (III) ions and carboxy groups of the carboxymethyl chitosan and catechol groups of the grafted dopamine, and
the particles are dispersed in the crosslinked network.

7. The hydrogel of claim 6, wherein:
the crosslinked network is dynamic in that the hydrogel is configured to self-heal into one piece after being severed into two pieces.

8. The hydrogel of claim 2, wherein:
a number average molecular weight of the oxidized sodium alginate is 4,000-10,000 g/mol, and
a number average molecular weight of the carboxy-functionalized polythiophene is 600-2,000 g/mol.

9. The hydrogel of claim 1, wherein:
the hydrogel has a storage modulus of 50 to 200 Pa, a swelling ratio of 200% to 375%, an electrical conductivity of $1.5\times10^{-4}$ to $10\times10^{-4}$ $Sm^{-1}$, and an adhesive strength of 2 to 17.5 kPa to mammalian skin.

10. The hydrogel of claim 1, wherein:
the hydrogel has a storage modulus of 94.8 to 120.9 Pa, a swelling ratio of 240% to 266%, an electrical conductivity of $5.0\times10^{-4}$ to $7.2\times10^{-4}$ $Sm^{-1}$, and an adhesive strength of 5.0 to 8.5 kPa to mammalian skin.

11. The hydrogel of claim 1, wherein:
the hydrogel does not include D-(+)-glucono delta-lactone, polyvinylpyrrolidone, tannic acid, gallic acid or a nanofiber film comprising fibers of polycaprolactone and polylactic acid on which the hydrogel is disposed.

12. The hydrogel of claim 1, wherein:
the iron (III) ions are in the form of ferric chloride.

13. A method of treating a wound, the method comprising applying to the wound a dressing comprising the hydrogel of claim 1.

14. The method of claim 13, wherein:
the dressing further comprises a base layer selected from the group consisting of a gauze, lint, plaster, bandage and cotton wool, and
the hydrogel is attached or adhered to the base layer.

15. The method of claim 13, further comprising irradiating the dressing with near-infrared light having a wavelength of 780 to 2500 nm for 0.5-30 minutes.

16. The method of claim 13, further comprising irradiating the dressing with near-infrared light having a wavelength of 808 nm for 3-10 minutes.

17. A method of preparing a hydrogel, the method comprising:
adding a carboxymethyl chitosan solution, a ferric chloride solution, deionized water and a dispersion of particles to an oxidized sodium alginate solution to form a mixture, the particles comprising a core comprising a carboxy-functionalized polythiophene and a shell comprising polydopamine; and
stirring the mixture to form the hydrogel.

18. The method of claim 17, further comprising:
oxidizing sodium alginate by sodium periodate to form oxidized sodium alginate having aldehyde groups, and
grafting dopamine to the oxidized sodium alginate in the presence of 1-(3-dimethylaminopropyl)-3-ethylcarbodiimide hydrochloride (EDC) and N-hydroxysuccinyl imine (NHS).

19. The method of claim 17, further comprising:
polymerizing methyl thiophene-3-acetate in the presence of ferric chloride to form poly(methyl thiophene-3-acetate);
hydrolyzing the poly(methyl thiophene-3-acetate) to form poly(thiophene-3-acetic acid); and
stirring the poly(thiophene-3-acetic acid) and dopamine hydrochloride in an alkaline condition to form the particles.

20. The method of claim 17, further comprising:
dissolving oxidized sodium alginate in phosphate buffered saline (PBS) to form the oxidized sodium alginate solution having a pH of 7.4;
dissolving carboxymethyl chitosan in PBS to form the carboxymethyl chitosan solution having a pH of 7.4;
dissolving ferric chloride in deionized water to form the ferric chloride solution; and
dispersing the particles in PBS to form the dispersion of particles.

* * * * *